US008425427B2

(12) United States Patent
Kanai et al.

(10) Patent No.: US 8,425,427 B2
(45) Date of Patent: Apr. 23, 2013

(54) PULSE WAVE DETECTION DEVICE, DEVICE CONTROL DEVICE, AND PULSE WAVE DETECTION METHOD

(75) Inventors: Etsuko Kanai, Kyoto (JP); Masami Funakura, Osaka (JP); Yasutaka Maeda, Osaka (JP); Makiko Noda, Osaka (JP)

(73) Assignee: Panasonic Corporation, Osaka (JP)

( * ) Notice: Subject to any disclaimer, the term of this patent is extended or adjusted under 35 U.S.C. 154(b) by 581 days.

(21) Appl. No.: 12/663,388

(22) PCT Filed: Jun. 6, 2008

(86) PCT No.: PCT/JP2008/001448
§ 371 (c)(1),
(2), (4) Date: Dec. 7, 2009

(87) PCT Pub. No.: WO2008/149559
PCT Pub. Date: Dec. 11, 2008

(65) Prior Publication Data
US 2010/0217137 A1      Aug. 26, 2010

(30) Foreign Application Priority Data

Jun. 8, 2007   (JP) .................................. 2007-152308
Jun. 8, 2007   (JP) .................................. 2007-152309

(51) Int. Cl.
*A61B 5/02*   (2006.01)
(52) U.S. Cl.
USPC .......................................... 600/500; 600/481
(58) Field of Classification Search .................. 600/500, 600/502–504
See application file for complete search history.

(56) References Cited

U.S. PATENT DOCUMENTS

| 5,368,026 | A  | * | 11/1994 | Swedlow et al. ............. 600/323 |
| 6,496,723 | B1 |   | 12/2002 | Kawachi et al. |
| 2006/0281995 | A1 | * | 12/2006 | Muramatsu et al. .......... 600/504 |

FOREIGN PATENT DOCUMENTS

| JP | 9-308614 | 12/1997 |
| JP | 10-137228 | 5/1998 |
| JP | 10-146321 | 6/1998 |
| JP | 11-151230 | 6/1999 |
| JP | 11-151231 | 6/1999 |

(Continued)

OTHER PUBLICATIONS

English machine translation from JPO of WO2007/007632.*
English machine translation from WIPO patent scope of WO2007/007632.*
International Search Report issued Jul. 1, 2008 in International (PCT) Application No. PCT/JP2008/001448.
First Reply (with English translation) in International (PCT) Application No. PCT/JP2008/001448.

*Primary Examiner* — Navin Natnithithadha
*Assistant Examiner* — Meredith Weare
(74) *Attorney, Agent, or Firm* — Wenderoth, Lind & Ponack, L.L.P.

(57) ABSTRACT

A pulse wave detection device detects pulse wave data from a pulse wave obtained from a user. The pulse wave detection device includes: a pulse wave detection unit detecting the pulse wave data from the pulse wave; a pulse wave derivative unit calculating velocity plethysmogram data by temporally deriving the pulse wave data; a component extraction unit extracting maximum and minimum values in a current first time range of the velocity plethysmogram data, while shifting the current first time range in a time axis direction, the extraction being repeated in a next current first time range; a component ratio calculation unit calculating a component ratio the maximum and minimum values extracted for each current first time range; and a noise segment determination unit determining, as a noise segment, a segment in which component ratios calculated by the component ratio calculation unit are temporally inconstant.

5 Claims, 39 Drawing Sheets

FOREIGN PATENT DOCUMENTS

| | | |
|---|---|---|
| JP | 2001-204714 | 7/2001 |
| JP | 2003-61921 | 3/2003 |
| JP | 2005-21450 | 1/2005 |
| JP | 3835073 | 10/2006 |
| JP | 2007/97615 | 4/2007 |
| WO | 2007/007632 | 1/2007 |
| WO | 2007/066493 | 6/2007 |

\* cited by examiner

FIG. 13

|  | Influence of thermal sensation | Influence of health condition |
| --- | --- | --- |
| Determination on change amount from starting point | Greater than 0.1 | Greater than 0.1 |
| Determination on change time from starting point | 10 minutes or shorter | Longer than 10 minutes |
| Determination on previous change amount | 0.1 or more | Smaller than 0.1 |

Thermal sensation range

Fatigue level range

FIG. 16

| Threshold value for change time from starting point (minute) | Effect |
|---|---|
| 1 to 3 | Small |
| 3 to 6 | Medium |
| 6 to 12 | Large |

(○:Maximum value, □:Minimum value)

FIG. 26

|  | Influence of thermal sensation | Influence of health condition |
|---|---|---|
| Determination on change amount from starting point | Greater than 0.1 | Greater than 0.1 |
| Determination on temperature change amount from starting point | Greater than 3 degrees Celsius | 3 degrees Celsius or below |

FIG. 27

| Threshold (certain degrees Celsius) for temperature change amount from starting point | Effect |
|---|---|
| 0.5 to 1 | Medium |
| 1 to 3 | Large |
| 3 to 4 | Small |

FIG. 31

|  | Influence of thermal sensation | Influence of health condition |
|---|---|---|
| Determination on change amount from starting point | Greater than 0.1 | Greater than 0.1 |
| Determination on integration value of change amounts from previous point | 1 or less | Greater than 1 |

FIG. 36

|  | Thermal sensation | Fatigue level |
|---|---|---|
| Determination on change amount from starting point | Greater than 0.1 | Greater than 0.1 |
| Determination on handle operation data | 15% or below | Greater than 15% |

FIG. 37

| Threshold value (%) for handle operation data | Effect |
|---|---|
| 10 to 12 | Small |
| 12 to 15 | Medium |
| 15 or more | Large |

US 8,425,427 B2

PULSE WAVE DETECTION DEVICE, DEVICE CONTROL DEVICE, AND PULSE WAVE DETECTION METHOD

TECHNICAL FIELD

The present invention relates to a pulse wave detection device which detects noise included in a pulse wave.

BACKGROUND ART

Recently, various research groups have been studying techniques for evaluating the health conditions of people based on their vital signs. As the results, some researchers found the correlation between the health conditions of the people and their vital signs, and proposed methods for evaluating the health conditions of people based on their vital signs at academic meetings. However, such correlation analysis was performed based on changes in vital signs observed in segments where the health conditions surely changed, and thus these results are mere results obtained at laboratories far different from real environments. At present, there is no established technique for performing back calculation to evaluate the health condition of a person in the case where a change in a vital sign is observed. One technique proposed in view of these problems as a method for discriminating a specific health condition of a person in the case where the person has a stress from a specific health condition of a person in the case where the person is doing sports is a technique for measuring a pulse wave, calculating pulse wave values, the upper peak values of the pulse wave, and the pulse pressure values each of which is the difference between an upper peak value and a corresponding lower peak value of the pulse wave, and determining a current status from among stress, sleepiness, fatigue (muscle fatigue) (See Patent Reference 1, for example).

FIG. 1 is a block diagram showing the structure of a health condition discrimination device disclosed in Patent Reference 1. The health condition discrimination device includes a pulse wave measurement unit 1301, a calculation unit 1302, a discrimination unit 1303, and an alert output unit 1304.

The pulse wave measurement unit 1301 measures the flow amount of haemoglobin carried by oxygen and the flow amount of haemoglobin not carried by oxygen which are generated through blood circulation. The calculation unit 1302 calculates data of pulse values, blood pressure values, and pulse pressure values each of which is the difference between the upper and lower peaks of a corresponding one of the pulse waves, based on the pulse wave data measured by the pulse wave measurement unit 1301. The discrimination unit 1303 detects changes in the data calculated by the calculation unit 1302, and discriminates the health conditions into plural levels. The alert output unit 1304 outputs alerts according to the levels discriminated by the discrimination unit 1303.

As mentioned above, there are attempts to detect pulse waves from human bodies using optical or piezoelectric pressure sensors, and determine human health conditions. However, pulse waves are susceptible to body movements or the like, and thus there is a need to discriminate between pulse wave signs and noise. Exemplary conventional methods for detecting noise included in pulse waves include a method for discriminating noise based on the variance in the peak values of velocity plethysmogram (abbreviated as VPG) obtained by differentiating the detected pulse waves (See Patent Reference 2, for example).

Patent Reference 1: Japanese Unexamined Patent Application Publication No. 2003-61921 (page 8, FIG. 2)
Patent Reference 2: Japanese Patent Publication No. 3835073

DISCLOSURE OF INVENTION

Problems that Invention is to Solve

The health condition discrimination device structured according to Patent Reference 1 determines the health condition of a user using a pulse wave. However, even when the health condition discrimination device can determine the health condition such as fatigue, stress or sleepiness, it is not sure whether or not the change in the pulse wave is made due to the influence of the determined health condition considering that a pulse wave is a vital sign also susceptible to a thermal environment. Accordingly, the health condition is determined based on the pulse wave affected by the thermal environment, which causes a problem that an erroneous result is highly likely to be outputted.

In addition, a pulse wave is significantly susceptible to body movements, in addition to health conditions, and thermal sensations. FIG. 2 shows a pulse waveform affected by body movements. The pulse waveform is affected by body movements in Segments A and B, while the pulse waveform is not affected by body movements in the other segments. In this way, the pulse waveform is found to be changed significantly due to the influence of the body movements. In addition, FIG. 3 shows a pulse waveform affected by changes in thermal sensation. The pulse waveform is affected by changes in the thermal sensation in Segment C, while the pulse waveform is not affected by changes in the thermal sensation in the other segments. In this way, the pulse waveform is found to be changed significantly due to the influence of the thermal sensations. Accordingly, at the time of noise detection, there is a need to discriminate a case where the pulse waveform changes due to the influence of body movements from a case where the pulse waveform changes due to the influence of changes in the thermal sensation. Here, according to the conventional method disclosed in Patent Reference 2, FIG. 4 shows a solid-line graph representing the variance values of the peak values of velocity plethysmogram (FIG. 5) obtained by performing first-order derivative on the pulse waveform shown in FIG. 2, and shows a broken-line graph representing the variance values of the peak values of velocity plethysmogram (FIG. 6) obtained by performing first-order derivative on the pulse waveform shown in FIG. 3. As clear from FIG. 4, the variance in Segment C affected by a thermal sensation may be smaller than the variance in Segment A affected by body movements, and may be greater than the variance in Segment B affected by body movements. For this, the conventional method according to Patent Reference 2 entails a problem that it is impossible to determine whether a pulse wave change indicates either a pulse wave sign made due to a change in thermal sensation or noise caused due to the influence of body movements.

The present invention has been made in order to solve the above-described problems, such that a purpose of the present invention is provide a pulse wave detection device which can discriminate a change in a pulse wave made by a change in thermal sensation from noise caused due to the influence of body movements.

In addition, another purpose of the present invention is to provide a device control device intended to evaluate a user's health condition based on a pulse wave after discriminating a change in the pulse wave made by a change in thermal sensation or noise caused due to the influence of body movements, and perform device control. More specifically, the purpose of the present invention is to discriminate whether the change in the pulse wave is made due to the influence of either the thermal environment or the health condition by firstly determining whether or not the pulse wave has changed due to the influence of the thermal environment, and to perform device control for reliably making the user's health condition better.

Means to Solve the Problems

A pulse wave detection device according to an aspect of the present invention is for detecting pulse wave data indicating a pulse wave of a user, and the wave detection device includes: a pulse wave detection unit configured to detect, in time series, the pulse wave data indicating the pulse wave of the user; a pulse wave derivative unit configured to calculate time-series velocity plethysmogram data by temporally deriving the time-series pulse wave data detected by the pulse wave detection unit; a component extraction unit configured to extract a maximum value and a minimum value in a current first time range in the time-series velocity plethysmogram data calculated by the pulse wave derivative unit while shifting the current first time range of the time-series velocity plethysmogram data in a direction of a time axis of the time-series velocity plethysmogram data, the extraction being repeated in a next current first time range of the time-series velocity plethysmogram data; a component ratio calculation unit configured to calculate a component ratio which is a ratio of the maximum value and the minimum value extracted for each current first time range by the component extraction unit; and a noise segment determination unit configured to determine, as a noise segment, a segment in which component ratios calculated by the component ratio calculation unit are temporally inconstant.

The pulse wave detection device with this structure determines whether or not the pulse wave includes noise by extracting the maximum values and the minimum values in the first time ranges based on the velocity plethysmogram obtained by performing first-order derivative on the pulse wave, calculating the ratios (component ratios), and determining whether or not the component ratios are temporally inconstant. For this, it is possible to discriminate the change in a pulse wave made by a change in thermal sensation from noise caused due to the influence of body movements.

It is preferable that the noise segment determination unit includes: a variance value calculation unit configured to calculate a variance value of component ratios included in a second time range within the velocity plethysmogram data; and a determination unit configured to determine that the second time range includes noise of the pulse wave data when it is determined that the variance value calculated by the variance value calculation unit does not fall within a predetermined range.

The pulse wave detection device with this structure determines whether or not the pulse wave includes noise using the variance values of component ratios. For this, it is possible to discriminate the change in the pulse wave made by a change in thermal sensation from noise caused due to the influence of body movements.

It is further preferable that the noise segment determination unit includes a determination unit configured to determine whether or not the component ratio calculated by the component ratio calculation unit falls within the predetermined range, and determine that the first time range includes noise of the pulse wave data when it is determined that the component ratio of the first time range does not fall within the predetermined range.

The pulse wave detection device determines whether or not the pulse wave includes noise by determining whether or not the component ratios fall within a predetermined range. For this, it is possible to discriminate the change in the pulse wave made by a change in thermal sensation from noise caused due to the influence of body movements.

A device control device according to an aspect of the present invention is for controlling an on-vehicle device based on pulse wave data indicating a pulse wave of a user, and the device control device includes a vital sign measurement unit configured to measure, in time series, the pulse wave data indicating the pulse wave of the user; a parameter extraction unit configured to extract time-series parameter values for evaluating current statuses of the user based on the time-series pulse wave data measured by the vital sign measurement unit; a determination unit configured to determine whether a factor of a change (e.g., a change factor) in the pulse wave data is a change in a health condition of the user or a change in an environment temperature around the user, based on the parameter values extracted by the parameter extraction unit; and a control unit configured to control the on-vehicle device based on a result of the determination made by the determination unit, wherein the vital sign measurement unit includes: a pulse wave detection unit configured to detect, in time series, the pulse wave data indicating the pulse wave of the user; a pulse wave derivative unit configured to calculate time-series velocity plethysmogram data by temporally deriving the time-series pulse wave data detected by the pulse wave detection unit; a component extraction unit configured to extract a maximum value and a minimum value in a current first time range in the time-series velocity plethysmogram data calculated by the pulse wave derivative unit while shifting the current first time range of the time-series velocity plethysmogram data in a direction of a time axis of the time-series velocity plethysmogram data, the extraction being repeated in a next current first time range of the time-series velocity plethysmogram data; a component ratio calculation unit configured to calculate a component ratio which is a ratio of the maximum value and the minimum value extracted for each current first time range by the component extraction unit; a noise segment determination unit configured to determine, as a noise segment, a segment in which component ratios calculated by the component ratio calculation unit are temporally inconstant; and a noise segment removal unit configured to remove pulse wave data included in the noise segment, from the time-series pulse wave data detected by the pulse wave detection unit.

The pulse wave detection device with this structure determines whether or not the pulse wave includes noise by extracting the maximum values and the minimum values in the first time ranges based on the velocity plethysmogram obtained by performing first-order derivative on the pulse wave, calculating the ratios (component ratios), and determining whether or not the component ratios are temporally inconstant. For this, it is possible to discriminate the change in the pulse wave made by a change in thermal sensation from noise caused due to the influence of body movements.

The pulse wave detection device can determine whether or not the factor of the change (e.g., the change factor) in the pulse wave data is a change in user's health condition or a change in environment temperature around the user, using the parameter values extracted from the pulse wave data. For this, it is possible to control an on-vehicle device based on the determination result. Accordingly, it is possible to evaluate a user's health condition based on pulse wave data and perform device control, more specifically, to discriminate whether the change in the pulse wave is made due to the influence of either a change in thermal environment or a change in health condition, and to perform device control for reliably making the user's health condition better.

It is preferable that the determination unit includes: a parameter change amount calculation unit configured to calculate, for each of the parameter values extracted by the parameter extraction unit, a change amount from a starting point which is the change amount between the parameter value extracted by the parameter extraction unit at a predetermined starting time point and a current parameter value; a parameter change time calculation unit configured to calculate, for each of the parameter values extracted by the parameter extraction unit, change time from the starting time point to a current time point at which the current parameter value is extracted; and a change factor determination unit configured to: make a first determination that the factor of the change (e.g., the change factor) in the vital sign is the change in the health condition of the user when (i) the change amount from the starting point calculated by the parameter change amount calculation unit is greater than a threshold value for the change amount from the starting point and (ii) the time required for the change calculated by the parameter change time calculation unit is greater than a threshold value for the time required for the change; and make a second determination that the factor of the change (e.g., the change factor) in the vital sign is the change in the environment temperature around the user when (i) the change amount from the starting point calculated by the parameter change amount calculation unit is greater than the threshold value for the change amount from the starting point and (ii) the time required for the change calculated by the parameter change time calculation unit is not greater than the threshold value for the time required for the change, the first or second determination being made for each parameter value extracted by the parameter extraction unit.

With this structure, it is possible to determine the factor of the change (e.g., the change factor) in the pulse wave data with reference to time required for the change in the pulse data in addition to the amount of the change, and control the on-vehicle device based on the determined factor. Accordingly, it is possible to evaluate a user's health condition based on pulse wave data and perform device control, more specifically, to discriminate whether the change in the pulse wave is made due to the influence of either a change in thermal environment or a change in health condition, and to perform device control for reliably making the user's health condition better.

It is further preferable that the determination unit includes: a parameter change amount calculation unit configured to calculate, for each of the parameter values extracted by the parameter extraction unit, a change amount from a starting point which is a change amount between a parameter value extracted by the parameter extraction unit at a predetermined starting time point and a current parameter value; an environment temperature measurement unit configured to measure, in time series, a current environment temperature around the user; a unit for calculating a temperature change amount from a starting point which calculates, for each of the environment temperatures measured by the environment temperature measurement unit, a temperature change amount from a starting point which is a change amount between an environment temperature at the starting point measured by the environment temperature measurement unit and a current environment temperature; and a change factor determination unit configured to: determine that the factor of the change (e.g., the change factor) in the vital sign is the change in the health condition of the user when (i) the change amount from the starting point calculated by the parameter change amount calculation unit is greater than a predetermined threshold value for the change amount from the starting point and (ii) the temperature change amount from the starting point calculated by the temperature change amount from the starting point is not greater than the threshold value for the predetermined temperature change amount from the starting point; and determine that the factor of the change (e.g., the change factor) in the vital sign is the change in the environment temperature around the user when (i) the change amount from the starting point calculated by the parameter change amount calculation unit is greater than the threshold value for the change amount from the starting point and (ii) the temperature change amount from the starting point calculated by the temperature change amount from the starting point is greater than the threshold value for the predetermined temperature change amount from the starting point.

With this structure, it is possible to determine the factor of the change (e.g., the change factor) in the pulse wave data with reference to the amount of the change in the environment temperature in addition to the amount of the change, and control the on-vehicle device based on the determined factor. Accordingly, it is possible to evaluate a user's health condition based on pulse wave data and perform device control, more specifically, to discriminate whether the change in the pulse wave is made due to the influence of either a change in thermal environment or a change in health condition, and to perform device control for reliably making the user's health condition better.

It is further preferable that the determination unit includes: a parameter change amount calculation unit configured to calculate, for each of the parameter values extracted by the parameter extraction unit, a change amount from a starting point which is a change amount between a parameter value extracted by the parameter extraction unit at a predetermined starting time point and a current parameter value; a parameter change amount integration unit configured to calculate, for each of the parameter values extracted by the parameter extraction unit, an integration value of change amounts each from a previous point, the integration value being obtained by integrating the change amounts of the parameter values extracted by the parameter extraction unit in a period from the starting time point to a time point at which the current parameter value is extracted; and a change factor determination unit configured to: determine that the factor of the change (e.g., the change factor) in the vital sign is the change in the health condition of the user when (i) the change amount from the starting point calculated by the parameter change amount calculation unit is greater than a predetermined threshold value for the change amount from the starting point and (ii) the integration value of the parameter values up to the current parameter value extracted by the parameter extraction unit is greater than a predetermined threshold value for the integration value; and determine that the factor of the change (e.g., the change factor) in the vital sign is the change in the environment temperature around the user when (i) the change amount from the starting point calculated by the parameter change amount calculation unit is greater than the threshold value for the change amount from the starting point and (ii) the integration value of the parameter values up to the current parameter value extracted by the parameter extraction unit is not greater than the predetermined threshold value for the integration value.

With this structure, it is possible to determine the factor of the change (e.g., the change factor) in the pulse wave data with reference to the integration value of the change amounts in addition to the current change amount, and control the on-vehicle device based on the determined factor. Accordingly, it is possible to evaluate a user's health condition based on pulse wave data and perform device control, more specifically, to discriminate whether the change in the pulse wave is made due to the influence of either a change in thermal environment or a change in health condition, and to perform device control for reliably making the user's health condition better.

It is further preferable that the device control device further includes a vehicle information obtainment unit configured to obtain information about a status of a vehicle driven by the user, and that the determination unit includes: a parameter change amount calculation unit configured to calculate, for each of the parameter values extracted by the parameter extraction unit, a change amount from a starting point which is a change amount between a parameter value extracted by the parameter extraction unit at a predetermined starting time point and a current parameter value; and a determination unit configured to determine whether the factor of the change (e.g., the change factor) in the pulse wave data is the change in the health condition of the user or the change in the environment temperature around the user, based on the change amount from the starting point calculated by the parameter change amount calculation unit and the vehicle status obtained by the vehicle information obtainment unit.

With this structure, it is possible to determine the factor of the change (e.g., the change factor) in the pulse wave data with reference to the status of the vehicle in addition to the change amount in the pulse wave data, and control the on-vehicle device based on the determined factor. Accordingly, it is possible to evaluate a user's health condition based on pulse wave data and perform device control, more specifically, to discriminate whether the change in the pulse wave is made due to the influence of either a change in thermal environment or a change in health condition, and to perform device control for reliably making the user's health condition better.

It is further preferable that the device control device further includes a vehicle information obtainment unit configured to obtain information about a status of a vehicle driven by a user, and that the determination unit includes: a parameter change amount calculation unit configured to calculate, for each of the parameter values extracted by the parameter extraction unit, a change amount from a starting point which is a change amount between a parameter value extracted by the parameter extraction unit at a predetermined starting time point and a current parameter value; a parameter change time calculation unit configured to calculate, for each of the parameter values extracted by the parameter extraction unit, time required for a change which is time from the starting time point to a time point at which the current parameter value is extracted; and a change factor determination unit configured to determine whether the factor of the change (e.g., the change factor) in the pulse wave data is the change in the health condition of the user or the change in the environment temperature around the user, based on the change amount from the starting point calculated by the parameter change amount calculation unit, the time required for the change calculated by the parameter change time calculating unit, and the vehicle's running status obtained by the vehicle information obtainment unit.

With this structure, it is possible to determine the factor of the change (e.g., the change factor) in the pulse wave data with reference to time required for the change in addition to the amount of the change in the pulse wave data, and control the on-vehicle device based on the determined factor. Accordingly, it is possible to evaluate a user's health condition based on pulse wave data and perform device control, more specifically, to discriminate whether the change in the pulse wave is made due to the influence of either a change in thermal environment or a change in health condition, and to perform device control for reliably making the user's health condition better.

It is to be noted that the present invention can be implemented not only as a pulse wave detection device including these unique processing units, but also as a pulse wave detection method including the steps corresponding to the unique processing units included in the pulse wave detection device, and as a program causing a computer to execute the unique steps included in the pulse wave detection method. As a matter of course, such program can be distributed using recording media such as CD-ROMs (Compact Disc-Read Only Memory) and can also be distributed via communication networks such as the Internet.

Effects of the Invention

According to the present invention, it is possible to provide a pulse wave detection device which discriminates a change in a pulse wave made by a change in thermal sensation from noise caused due to the influence of body movements.

In addition, another purpose of the present invention is to provide a device control device intended to evaluate a user's health condition based on a pulse wave after discriminating whether a change in the pulse wave is made by a change in thermal sensation or noise caused due to the influence of body movements, and perform device control. More specifically, the purpose of the present invention is to discriminate a change made due to the influence of a thermal environment from a change made due to the influence of a health condition by firstly determining whether or not the pulse wave has changed due to the influence of the thermal environment, and to perform device control for reliably making the user's health condition better.

BRIEF DESCRIPTION OF DRAWINGS

FIG. 13 is a diagram showing a data table used for determining the factor of a change (e.g., the change factor) in the pulse wave amplitude stored by the change factor determination unit according to Embodiment 1 of the present invention.

FIG. 16 is a diagram for illustrating a threshold value for starting point change time used for discriminating between thermal sensations and fatigue levels.

FIG. 21(a) is a graph representing temporal changes in the amplitude value of Wave a that is a first wave of the velocity plethysmogram which has not yet been subjected to the noise removal. FIG. 21(b) is a graph representing temporal changes in the amplitude value of Wave a of the velocity plethysmogram which has been subjected to the noise removal.

FIG. 26 is a diagram showing a data table used for determining the factor of a change (e.g., the change factor) in the pulse wave amplitude stored by the change factor determination unit according to Embodiment 2 of the present invention.

FIG. 27 is a diagram for illustrating a threshold vale for the temperature change amount from a starting point for discriminating between thermal sensations and fatigue levels.

FIG. 31 is a diagram showing a data table used for determining the factor of a change (e.g., the change factor) in the pulse wave amplitude stored by the change factor determination unit according to Embodiment 3 of the present invention.

FIG. 36 is a diagram showing a data table used for determining the factor of a change (e.g., the change factor) in the pulse wave amplitude stored by the change factor determination unit according to Embodiment 4 of the present invention.

FIG. 37 is a diagram for illustrating a threshold vale for handle operation data used for discriminating between thermal sensations and fatigue levels.

| Numerical References | |
|---|---|
| 1 | Pulse wave sensor |
| 101, 1101, 3101 | Vital sign measurement unit |
| 102 | Parameter extraction unit |
| 103 | Parameter change amount calculation unit |
| 104 | Parameter change time calculation unit |
| 105, 506, 905, 1105, 1205 | Change factor determination unit |
| 106, 1116 | Status evaluation unit |
| 107, 1117 | Device control unit |
| 108 | Thermal sensation evaluation unit |

-continued

| Numerical References | |
|---|---|
| 109 | Health condition evaluation unit |
| 120, 520, 920, 1017, 1120, 1220, 3017 | Determination unit |
| 130, 1130 | Control unit |
| 504 | Environment temperature measurement unit |
| 505 | Unit for calculating a temperature change amount from a starting point |
| 904 | Parameter change amount integration unit |
| 1011, 1121 | Pulse wave detection unit |
| 1012 | Pulse wave derivative unit |
| 1013 | Component extraction unit |
| 1014 | Component ratio calculation unit |
| 1015 | Component ratio storage unit |
| 1016 | Variance value calculation unit |
| 1018 | Noise segment removal unit |
| 1019 | Accumulation unit |
| 1109 | Fatigue evaluation unit |
| 1111 | Superior control unit |
| 1112 | Vehicle information obtainment unit |
| 1113 | Fatigue related device control unit |
| 1114 | Thermal sensation related device control unit |

DETAILED DESCRIPTION OF THE INVENTION

Embodiments of the present invention will be described below with reference to the drawings.

Embodiment 1

Figure 7:
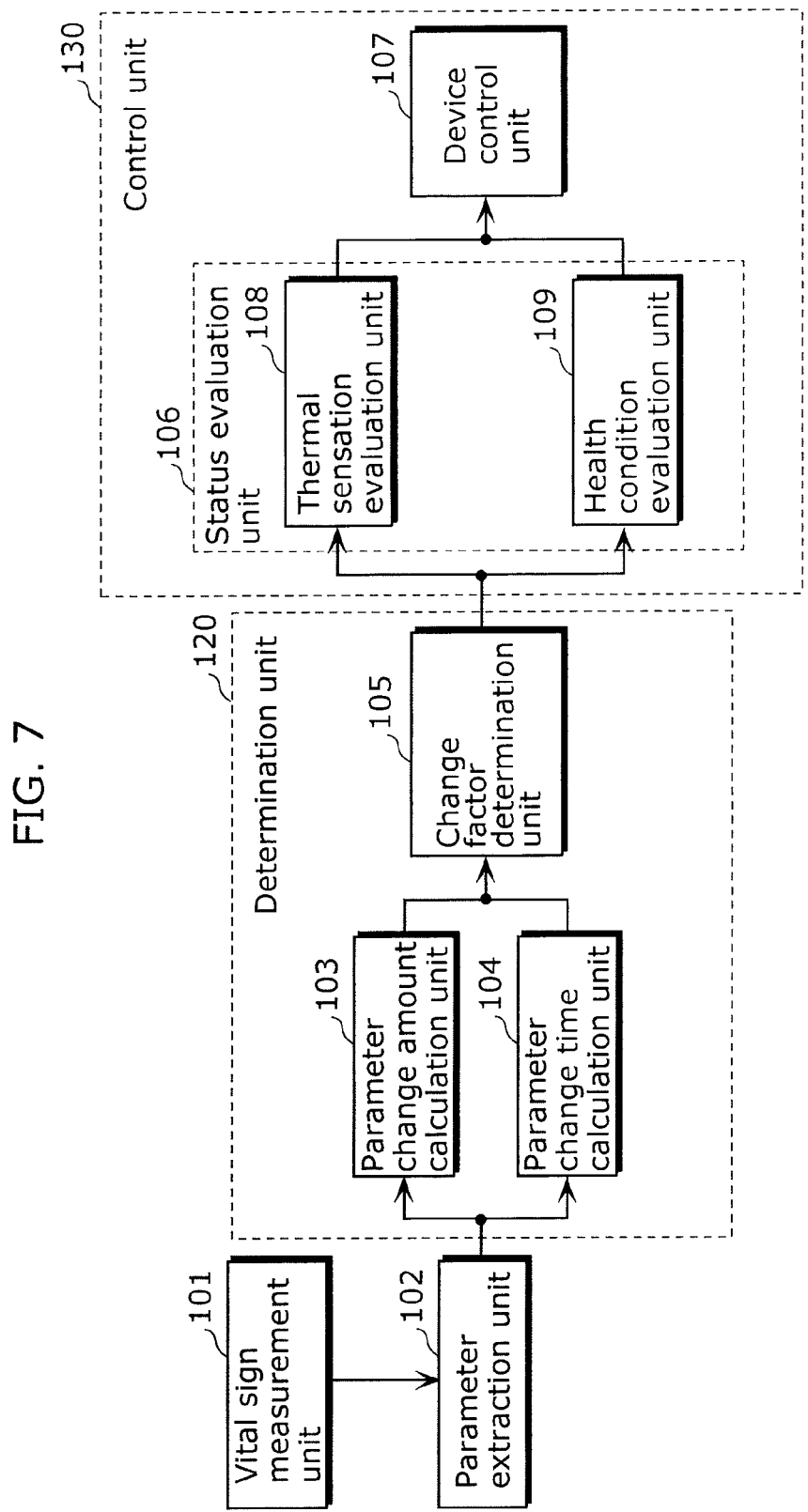
FIG. 7 is a block diagram showing the structure of a device control device according to Embodiment 1 of the present invention.

FIG. 7 is a block diagram showing the structure of a device control device according to Embodiment 1 of the present invention. The device control device shown in FIG. 7 is configured with known computers for example, and includes a vital sign measurement unit 101, a parameter extraction unit 102, a determination unit 120, and a control unit 130. These processing units function when the program is executed by a CPU of a computer storing an installed device control program designed according to this embodiment.

The vital sign measurement unit 101 samples a user's finger-tip pulse wave detected by a known transducer or the like at a predetermined sampling cycle, and obtains pulse wave data in time series. The parameter extraction unit 102 extracts the amplitude of the pulse waveform from the pulse wave data as parameter values for evaluating the pulse wave, and accumulates the parameter values.

The determination unit 120 is a processing unit for determining the factor of a change (e.g., a change factor) in the pulse wave data using the parameter values extracted by the parameter extraction unit 102. The determination unit 120 includes a parameter change amount calculation unit 103, a parameter change time calculation unit 104, and a change factor determination unit 105.

The parameter change amount calculation unit 103 (i) calculates, as a change amount from a starting point, the difference between the value at the predetermined starting time point and the value at a current time point in the time-series data of the pulse wave amplitude extracted by the parameter extraction unit 102, (ii) calculates, as a previous change amount, the difference between the value at the previous measurement time point and the value at the current time point, and (iii) outputs the change amount from the starting point and the previous change amount to the change factor determination unit 105.

The parameter change time calculation unit 104 calculates, as change time from the starting point, an elapsed time from the predetermined starting time point to the current time point in the pulse wave amplitude extracted by the parameter extraction unit 102, and outputs the change time from the starting point to the change factor determination unit 105.

The change factor determination unit 105 determines the factor of the change in the pulse wave amplitude (the factor is, for example, the influence of a thermal sensation or the influence of a health condition), based on (i) the change amount from the starting point and the previous change amount calculated by the parameter change amount calculation unit 103 and (ii) the change time from the starting point calculated by the parameter change time calculation unit 104. Based on the determined factor, the change factor determination unit 105 selects the best evaluation unit from among a thermal sensation evaluation unit 108 and a health condition evaluation unit 109 included in a later-described status evaluation unit 106, and outputs, to the selected evaluation unit, the current change amount from the starting point that is information to be used for evaluating the current status.

The control unit 130 is a processing unit for performing device control based on the result of the determination made by the change factor determination unit 105, and includes the status evaluation unit 106 and a device control unit 107.

The status evaluation unit 106 includes (i) the thermal sensation evaluation unit 108 for evaluating a user's thermal sensation based on the change amount from the starting point in the pulse wave amplitude and (ii) the health condition evaluation unit 109 for evaluating a user's health condition based on the same change amount from the starting point in the pulse wave amplitude. The thermal sensation evaluation unit 108 evaluates the user's thermal sensation based on the change amount from the starting point outputted by the change factor determination unit 105, and outputs the evaluation result to the device control unit 107. The health condition evaluation unit 109 evaluates the user's health condition based on the change amount from the starting point outputted by the change factor determination unit 105, and outputs the evaluation result to the device control unit 107.

Thermal sensations include not only a thermal sensation but also an omen of a change in a vital sign before the perception of the thermal sensation.

Here, the change factor determination unit 105 outputs the current change amount from the starting point as the information to be used for evaluating the thermal sensation, and the thermal sensation evaluation unit 108 evaluates the user's thermal sensation based on the change amount from the starting point. Alternatively, it is also good that the change factor determination unit 105 outputs the previous change amount as the information to be used for evaluating the thermal sensation, and the thermal sensation evaluation unit 108 evaluates the user's thermal sensation based on the previous change amount.

Based on either the thermal sensation evaluated by the thermal sensation evaluation unit 108 or the health condition evaluated by the health condition evaluation unit 109, the device control unit 107 performs either (i) device control for notifying the user of the evaluation result of the user's thermal sensation or the user's health condition, or (ii) device control for making better the user's thermal sensation or the user's health condition.

Figure 8:
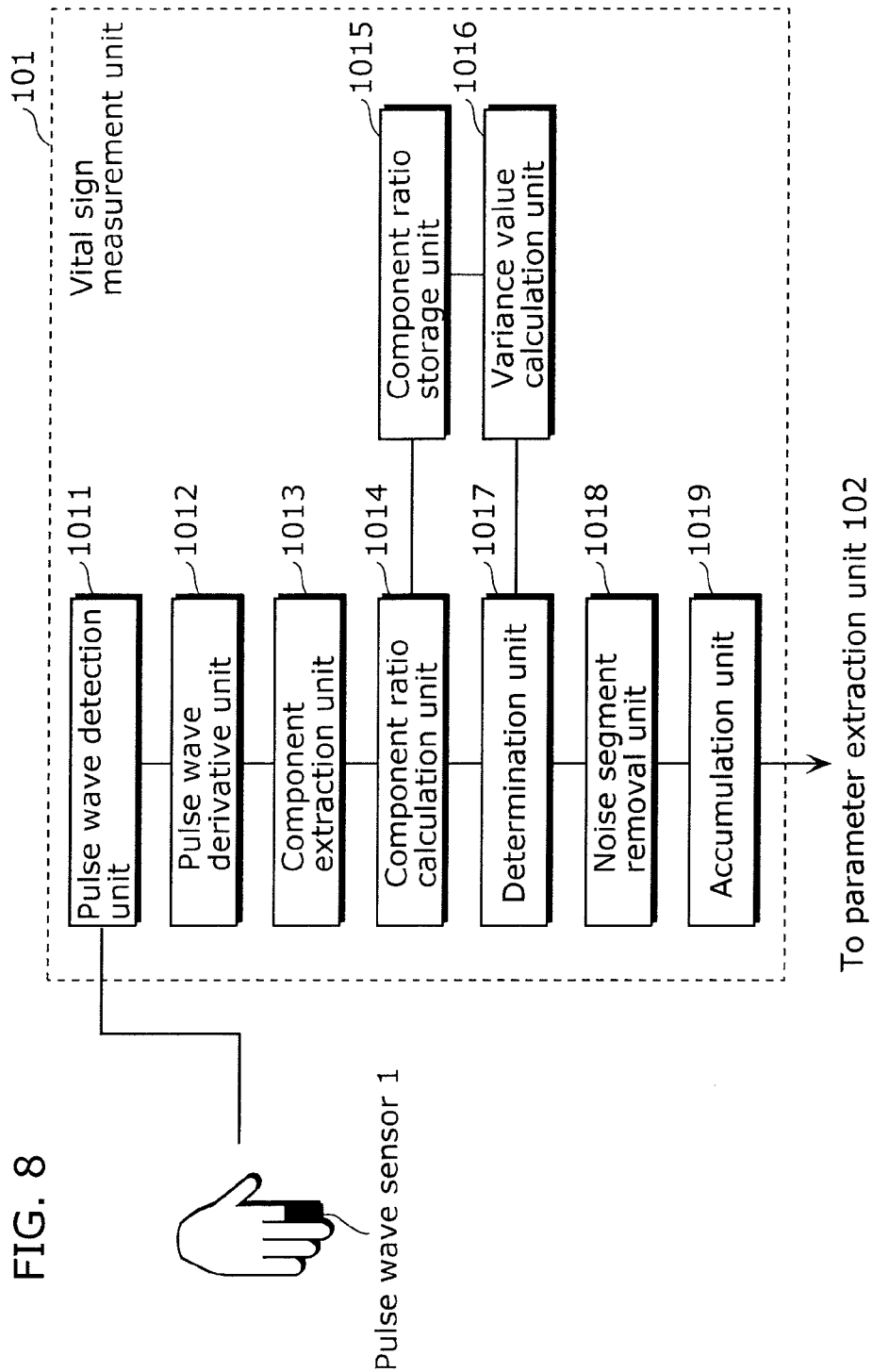
FIG. 8 is a block diagram showing the detailed structure of a vital sign measurement unit.

FIG. 8 is a block diagram showing the detailed structure of the vital sign measurement unit 101. It is assumed that the vital sign measurement unit 101 is connected to a pulse wave sensor 1.

The pulse wave sensor 1 is a known transparent optical sensor including light emitting elements and light receiving elements, and is intended to measure a pulse wave when mounted on a finger-tip portion.

The vital sign measurement unit 101 includes a pulse wave detection unit 1011, a pulse wave derivative unit 1012, a component extraction unit 1013, a component ratio calculation unit 1014, a component ratio storage unit 1015, a variance value calculation unit 1016, a determination unit 1017, a noise segment removal unit 1018, and an accumulation unit 1019.

The pulse wave detection unit 1011 detects, as a pulse wave, an output signal from the pulse wave sensor 1. The pulse wave derivative unit 1012 performs first-order derivative on the pulse wave detected by the pulse wave detection unit 1011 to obtain a velocity plethysmogram. The component extraction unit 1013 extracts the maximum value and the minimum value in each of predetermined time ranges of the velocity plethysmogram obtained by the pulse wave derivative unit 1012. The component ratio calculation unit 1014 calculates a component ratio by dividing the minimum value by the maximum value of the velocity plethysmogram extracted by the component extraction unit 1013.

The component ratio storage unit 1015 stores the component ratio calculated by the component ratio calculation unit 1014. The variance value calculation unit 1016 calculates component ratio variance values stored in the component ratio storage unit 1015. It is assumed here that the variance values are sample variance values, and are calculated using the following expression.

$$\sigma^2 = \frac{1}{n}\sum_{i=1}^{n}(\overline{x} - x_i)^2 \qquad \text{[Expression 1]}$$

It is also good that the variance values are calculated using the following expression when calculation can be continued to infinite order.

$$\sigma^2 = \frac{1}{n}\sum_{i=1}^{n}x_i^2 - (x)^2 = \overline{x^2} - (\overline{x})^2 \qquad \text{[Expression 2]}$$

The determination unit 1017 determines whether or not the pulse wave contains noise, based on the variance values of the plural component ratios calculated by the variance value calculation unit 1016.

The noise segment removal unit 1018 removes a pulse wave portion corresponding to the noise segment. The accumulation unit 1019 accumulates the data of the pulse wave without the portion corresponding to the noise segment.

Figure 1:
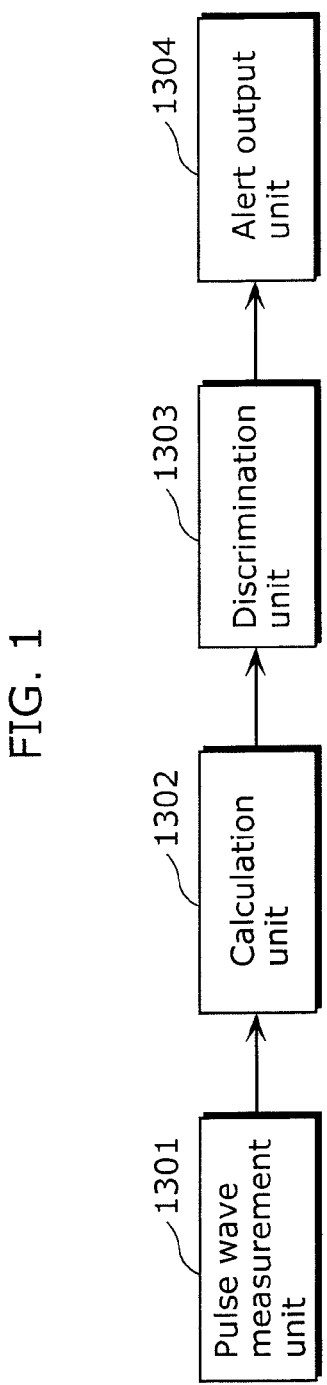
FIG. 1 is a block diagram showing the structure of a conventional health condition discrimination device.
Figure 2:
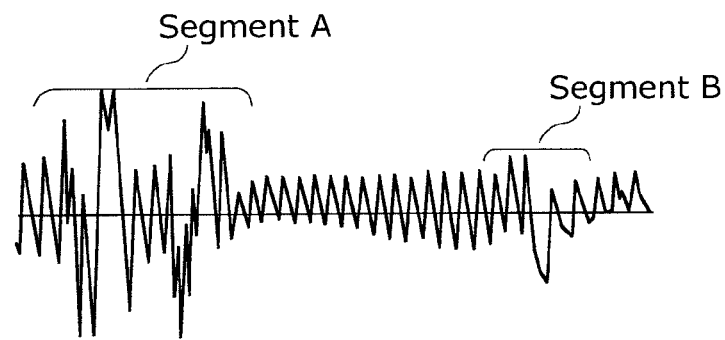
FIG. 2 is a diagram showing a pulse waveform affected by body movements.
Figure 3:
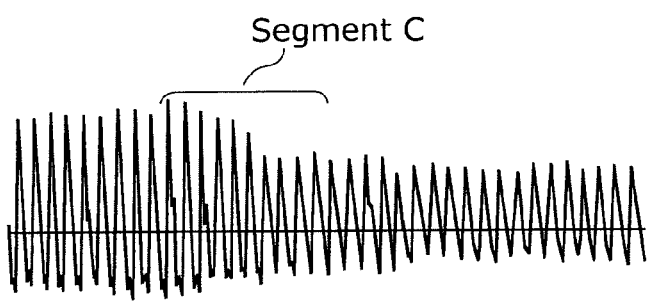
FIG. 3 is a diagram showing a pulse waveform affected by changes in the thermal sensation.
Figure 4:
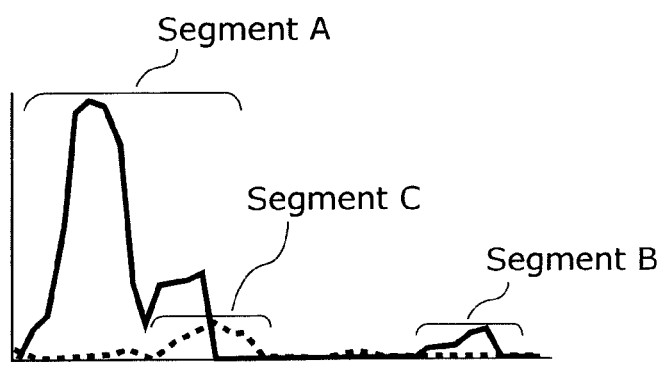
FIG. 4 is a diagram showing (i) a graph representing variance of the peak values of velocity plethysmogram obtained by performing first-order derivative on the pulse waveform shown in FIG. 2, and (ii) a graph representing the variance of the peak values of velocity plethysmogram obtained by performing first-order derivative on the pulse waveform shown in FIG. 3.
Figure 5:
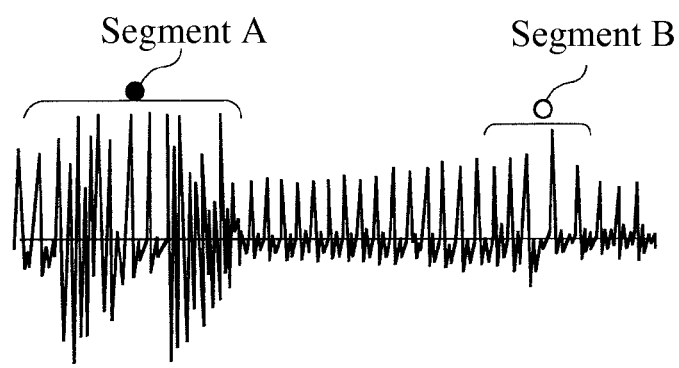
FIG. 5 is a diagram showing a velocity plethysmogram affected by body movements.
Figure 6:
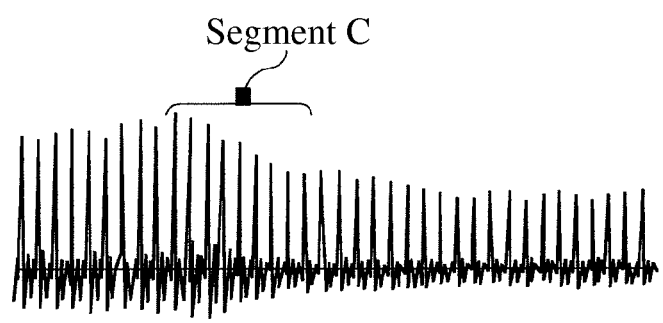
FIG. 6 is a diagram showing a velocity plethysmogram affected by changes in the thermal sensation.
Figure 9:
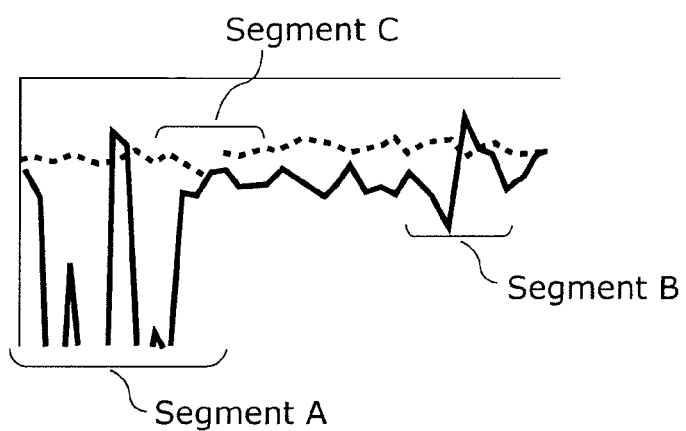
FIG. 9 is a graph showing the ratio of each of maximum values and the corresponding one of minimum values (the ratio is obtained by dividing the minimum value by the maximum value) of the velocity plethysmogram extracted, on a per predetermined time range basis, based on (i) the velocity plethysmogram data affected by the body movements shown in FIG. 5 and (ii) the velocity plethysmogram data affected by the changes in the thermal sensation shown in FIG. 6.

FIG. 9 shows (i) a solid-line graph representing the maximum value and the minimum value (the minimum value/the maximum value) of the velocity plethysmogram extracted, on a per predetermined time range basis, based on the velocity plethysmogram data affected by the body movements shown in FIG. 5 (Segments A and B are the segments affected by the body movements), and (ii) a broken-line graph representing the ratio of the maximum value and the minimum value (the minimum value/the maximum value) of the velocity plethysmogram extracted, on a per predetermined time range basis, based on the velocity plethysmogram data affected by the change in the thermal sensation shown in FIG. 6(Segment C is the segment affected by the thermal sensation). Here, as shown in FIG. 9, the Inventors of the present invention have found that the ratio of the maximum value and the minimum value in the velocity plethysmogram changes significantly in each of Segments A and B affected by the body movements, and that the ratio of the maximum value and the minimum value in the velocity plethysmogram changes slightly in Segment C affected by the change in the thermal sensation. Accordingly, the use of the ratio of the maximum value and the minimum value in the velocity plethysmogram makes it possible to discriminate the change in the pulse wave due to a change in the thermal sensation from noise caused due to the influence of body movements.

Figure 10:
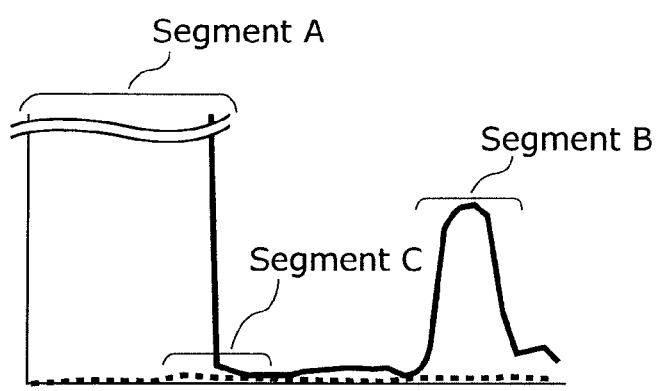
FIG. 10 is a graph showing the variance in the ratio of each of maximum values and a corresponding one of minimum value (the minimum value/the maximum value) of the velocity plethysmogram extracted, on a per predetermined time range basis, based on (i) the velocity plethysmogram data affected by the body movements shown in FIG. 5 and (ii) the velocity plethysmogram data affected by the changes in the thermal sensation shown in FIG. 6.

FIG. 10 shows (i) a solid-line graph representing the variance values of the ratio of the maximum value and the minimum value (the minimum value/the maximum value) of the velocity plethysmogram extracted, on a per predetermined time range basis, based on the velocity plethysmogram data affected by body movements shown in FIG. 5 (Segments A and B are the segments affected by the body movements), and (ii) a broken-line graph representing the variance value of the ratio of the maximum value and the minimum value (the minimum value/the maximum value) of the velocity plethysmogram extracted, on a per predetermined time range basis, based on the velocity plethysmogram data affected by change in the thermal sensation shown in FIG. 6 (Segment C is the segment affected by the thermal sensation). Here, as shown in FIG. 10, the Inventors of the present invention have found that the variance in the ratios of the maximum values and the minimum values in the velocity plethysmogram changes significantly in each of Segments A and B affected by the body movements, and that the variance of the ratios of the maximum values and the minimum values in the velocity plethysmogram changes slightly in Segment C affected by the change in the thermal sensation. Accordingly, the use of the variance of the ratios of the maximum values and the minimum values in the velocity plethysmogram makes it possible to discriminate the change in the pulse wave due to the change in the thermal sensation from noise caused due to the influence of the body movements.

Next, a description is given of processing performed by the device control device according to Embodiment 1.

Figure 11:
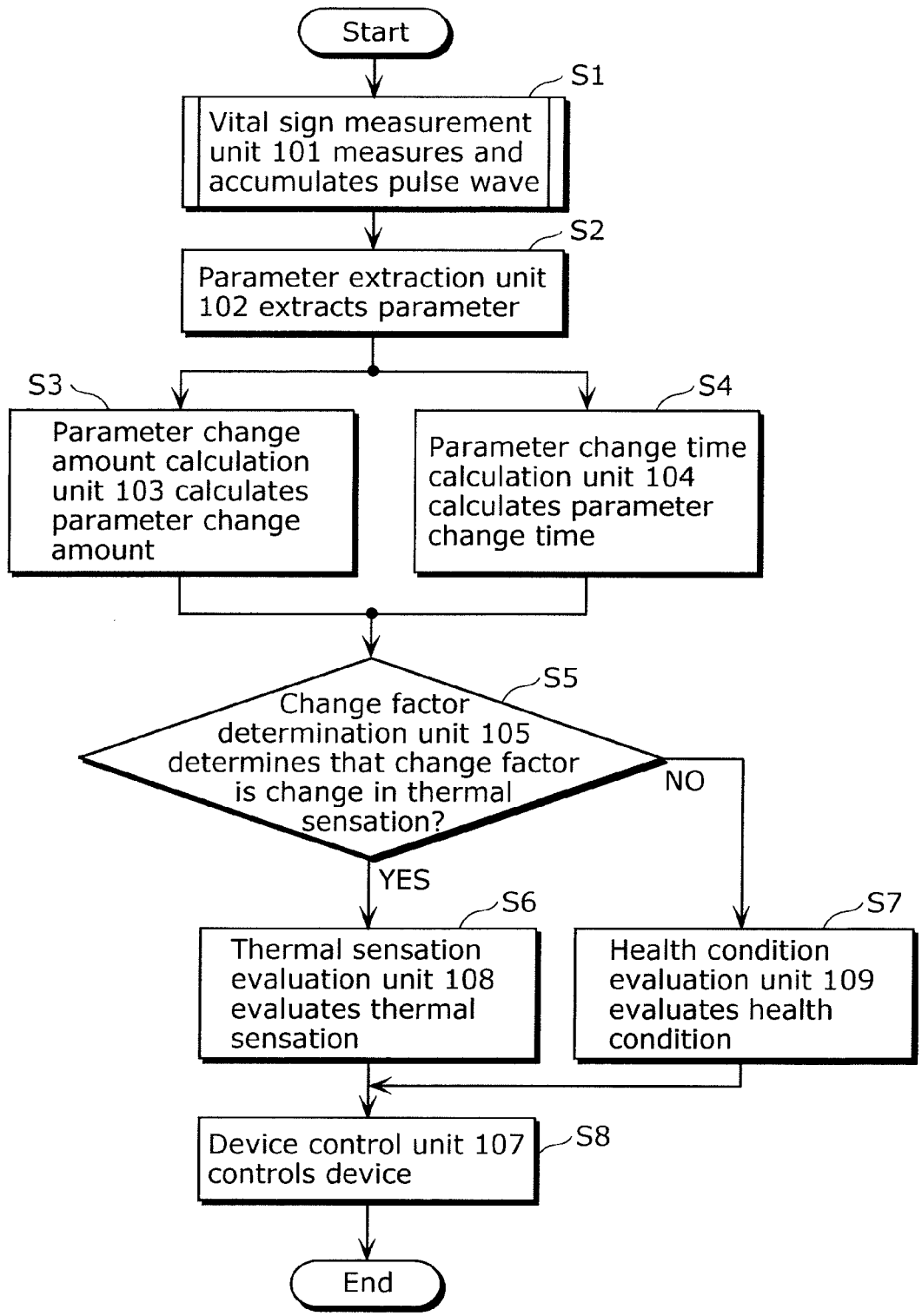
FIG. 11 is a flowchart of processing performed by the device control device according to Embodiment 1 of the present invention.

FIG. 11 is a flowchart of processing performed by the device control device according to Embodiment 1 of the present invention.

The vital sign measurement unit 101 measures and accumulates pulse wave data in time series (S1). This process (S1) is described later in detail.

The parameter extraction unit 102 extracts pulse wave amplitude from the time-series pulse wave data measured by the vital sign measurement unit 101 on a predetermined time range basis, and accumulates the pulse wave amplitude (S2).

The parameter change amount calculation unit 103 calculates, as a change amount from the starting point, the difference between the value at the predetermined starting time point and the value at a current time in the time-series pulse wave amplitude data extracted by the parameter extraction unit 102. In addition, the parameter change amount calculation unit 103 calculates, as the previous change amount, the difference between the value at the previous measurement time point and the value at the current time point. The parameter change amount calculation unit 103 outputs the calculated change amount from the starting point and the previous change amount to the change factor determination unit 105 (S3).

Meanwhile, the parameter change time calculation unit 104 calculates, as change time from the starting point, an elapsed time from the predetermined starting time point to the current time point in the time-series pulse wave amplitude data extracted by the parameter extraction unit 102, and outputs the change time from the starting point to the change factor determination unit 105 (S4).

The change factor determination unit 105 determines the factor of the change in the pulse wave amplitude, based on (i) the change amount from the starting point and the previous change amount outputted by the parameter change amount calculation unit 103 and (ii) the change time from the starting point outputted by the parameter change time calculation unit 104 (S5). When the change factor determination unit 105 determines that the factor of the change is the change in the thermal sensation (YES in S5), it outputs, to the thermal sensation evaluation unit 108, the current change amount from the starting point that is information to be used for evaluating the thermal sensation. When the change factor determination unit 105 determines that the factor of the change is the change in the health condition (NO in S5), it outputs, to the health condition evaluation unit 109, the current change amount from the starting point that is information to be used for evaluating the health condition. This determination process (S5) is described later in detail.

The thermal sensation evaluation unit 108 evaluates the user's thermal sensation based on the change amount from the starting point outputted by the change factor determination unit 105, and outputs the evaluation result to the device control unit 107 (S6). In other words, the thermal sensation evaluation unit 108 evaluates the user's thermal sensation based on a code representing the change amount from the starting point. For example, the thermal sensation evaluation unit 108 evaluates that the thermal sensation is shifted to "hot" when the value of the change amount is positive, and that the thermal sensation is shifted to "cold" when the value of the change amount is negative. In other words, the thermal sensation evaluation unit 108 evaluates that the thermal sensation is shifted to "hot" when the pulse wave amplitude of the pulse waveform increases, and that the thermal sensation is shifted to "cold" when the pulse wave amplitude of the pulse waveform decreases. It is also good to evaluate a thermal sensation based on not the pulse wave amplitude but (i) the maximum value of the pulse wave height, (ii) the waveform component ratio of the waveform of an accelerated plethysmogram (abbreviated as APG) obtained by performing second-order derivative on the pulse waveform, (iii) the amplitude of the accelerated plethysmogram or the pulse rate, and (iv) the change amount in parameters obtainable by performing frequency analysis on a pulse wave interval basis.

Here, in the case of using the parameter obtainable by performing frequency analysis on a pulse wave interval basis, it is also good to use a ratio of low frequency components (0.04 Hz to 0.15 Hz, for example) and high frequency components (0.15 Hz to 0.4 Hz, for example) obtained by dividing the low frequency components by the high frequency components (abbreviated as LF/HF), and evaluate that the thermal sensation is shifted to "discomfort" when the ratio increases and that the thermal sensation is shifted to "comfort" when the ratio decreases.

The health condition evaluation unit 109 evaluates the user's health condition based on the change amount from the starting point outputted by the change factor determination unit 105, and outputs the evaluation result to the device control unit 107 (S7). A description is given of an exemplary case where the health condition evaluation unit 109 evaluates a fatigue level. For example, the health condition evaluation unit 109 evaluates that the fatigue level decreases when the change amount from the starting point is positive, and that the fatigue level increases when the change amount from the starting point is negative. In other words, the health condition evaluation unit 109 evaluates that the fatigue level decreases when the pulse wave amplitude of the pulse waveform increases, and that the fatigue level increases when the pulse wave amplitude of the pulse waveform decreases. It is also good to evaluate a fatigue level based on not the pulse wave amplitude but (i) the maximum value of the pulse wave height, (ii) the waveform component ratio of the waveform of the accelerated plethysmogram obtained by performing second-order derivative on the pulse waveform, (iii) the amplitude of the accelerated plethysmogram or the pulse rate, and (iv) the change amount in parameters obtainable by performing frequency analysis on a pulse wave interval basis.

Here, the fatigue levels include not only a perceived fatigue level but also an unperceived fatigue level.

In addition, in the case of using the parameter obtainable by performing frequency analysis on a pulse wave interval basis, it is also good to use the ratio of low frequency components (0.04 Hz to 0.15 Hz, for example) and high frequency components (0.15 Hz to 0.4 Hz, for example) obtained using the LF/HF, and evaluate that the fatigue level increases when the ratio increases and that the fatigue level decreases when the ratio decreases.

The device control unit 107 controls a predetermined device based on the evaluation result outputted by either the thermal sensation evaluation unit 108 or the health condition evaluation unit 109 (S8). For example, it is also good to perform device control for notifying the user of the evaluation result. In addition, it is also good to perform device control for making better the thermal sensation or the health condition as the evaluation result.

Figure 12:
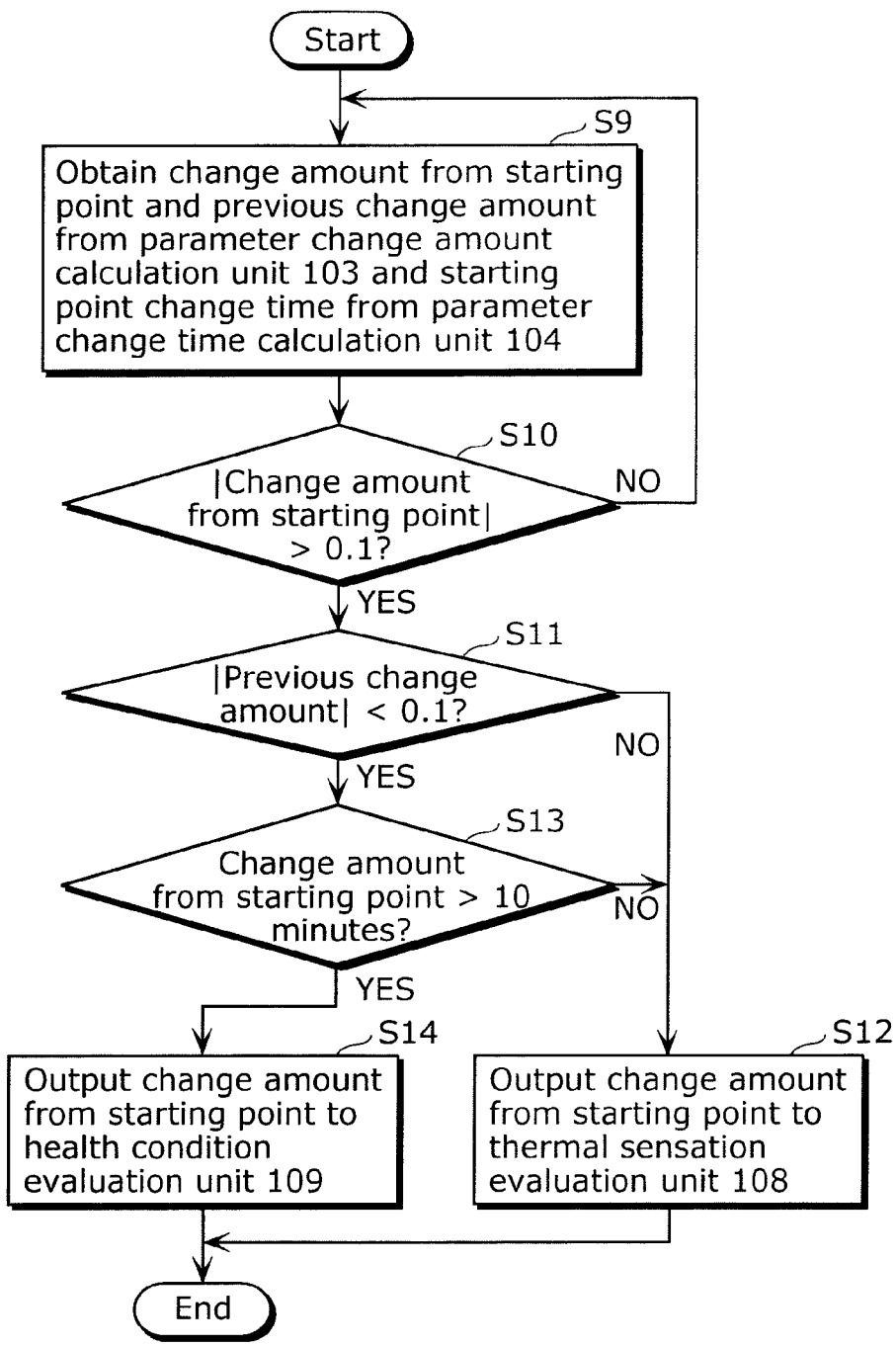
FIG. 12 is a flowchart of processing performed by the change factor determination unit according to Embodiment 1 of the present invention.

Next, a detailed description is given of a determination process (S5 in FIG. 11) for determining the factor of a change in the pulse wave amplitude made by the change factor determination unit 105. FIG. 12 is a flowchart of processing performed by the change factor determination unit 105 according to Embodiment 1 of the present invention. In addition, FIG. 13 is a diagram showing a data table used for determining the factor of a change in the amplitude of the pulse wave amplitude stored in the change factor determination unit 105. The processing shown in FIG. 12 is described below based on the contents of the data table shown in FIG. 13.

First, the change factor determination unit 105 obtains the change amount from the starting point and the previous change amount from the parameter change amount calculation unit 103, and obtains the change time from the starting point from the parameter change time calculation unit 104 (S9). The change factor determination unit 105 determines whether or not the absolute value of the change amount from the starting point is greater than a predetermined numerical value (0.1) (S10). When the absolute value of the change amount from the starting point is greater than 0.1 (YES in S10), the change factor determination unit 105 determines whether or not the absolute value of the previous change amount is smaller than the predetermined numerical value (0.1) (S11). When the absolute value of the change amount from the starting point is not greater than 0.1 (NO in S10), the change factor determination unit 105 waits until the next change amount from the starting point and the previous change amount are obtained, and repeats the processing from S9.

When the absolute value of the previous change amount is smaller than 0.1 (YES in S11), the change factor determination unit 105 determines whether or not the change time from the starting point is greater than a predetermined value (10 minutes) (S13). When the absolute value of the previous change amount is greater than 0.1 (NO in S11), the change factor determination unit 105 determines that the factor of the change in the pulse wave amplitude is a change in the thermal sensation as shown in FIG. 13, and outputs, to the thermal sensation evaluation unit 108, the current change amount from the starting point that is information to be used for evaluating the thermal sensation (S12). When the change time from the starting point is greater than 10 minutes (YES in S13), the change factor determination unit 105 determines that the factor of the change in the pulse wave amplitude is a change in the health condition as shown in FIG. 13, and outputs the current change amount from the starting point that is information to be used for evaluating the health condition to the health condition evaluation unit 109 (S14). When the change time from the starting point is not greater than 10 minutes (NO in S13), the change factor determination unit 105 determines that the factor of the change in the pulse wave amplitude is a change in the thermal sensation, and outputs, to the thermal sensation evaluation unit 108, the current change amount from the starting point that is information to be used for evaluating the thermal sensation (S12).

Next, a description is given of why 10 minutes is used as the threshold value for the change time from the starting point in the data table shown in FIG. 13.

Figure 14:
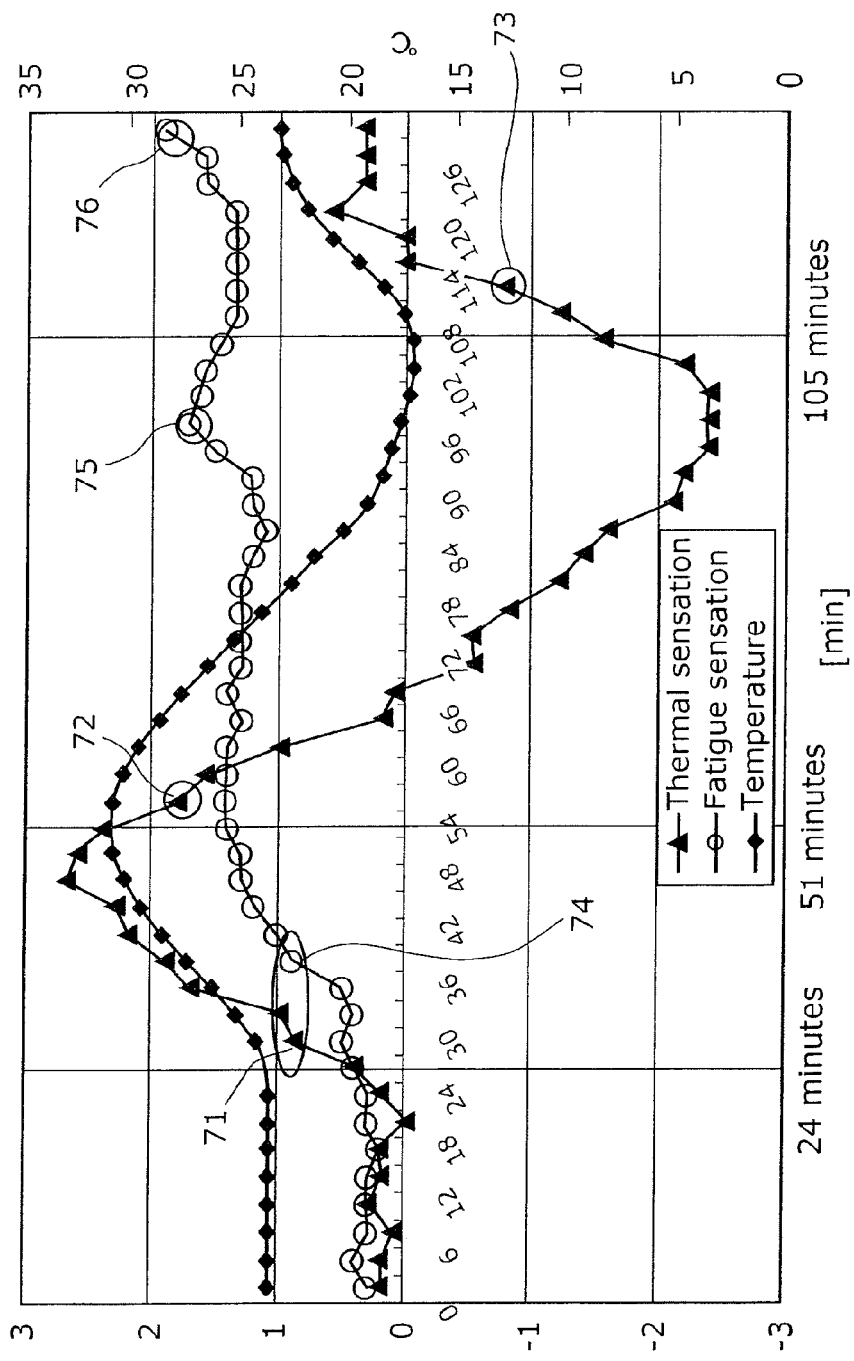
FIG. 14 shows graphs showing changes in the thermal sensation and fatigue level in the case where the environment temperature changes.

FIG. 14 shows graphs of changes in the thermal sensation and fatigue level in the case where the environment temperature changes. The horizontal axis shows time. Meanwhile, the vertical axis shows temperatures, thermal sensation levels, and fatigue levels. These graphs show the average values of the thermal sensation levels and the fatigue levels perceived by 10 subjects in the case where the environment temperature changes within a range of approximately 17 to 32 degrees Celsius. The thermal sensation levels are represented as values within a range between −3 to +3 inclusive. Here, "+3" denotes the hottest level, and "−3" denotes the coldest level. The numerical value increases toward the positive side as the level of hot sensation increases. In addition, the fatigue levels fall within the range between 0 and 3 inclusive. "0" indicates that the fatigue level is none, and "3" indicates that the fatigue level is the maximum level. The numerical value increases toward the positive side as the fatigue level increases.

Figure 15:
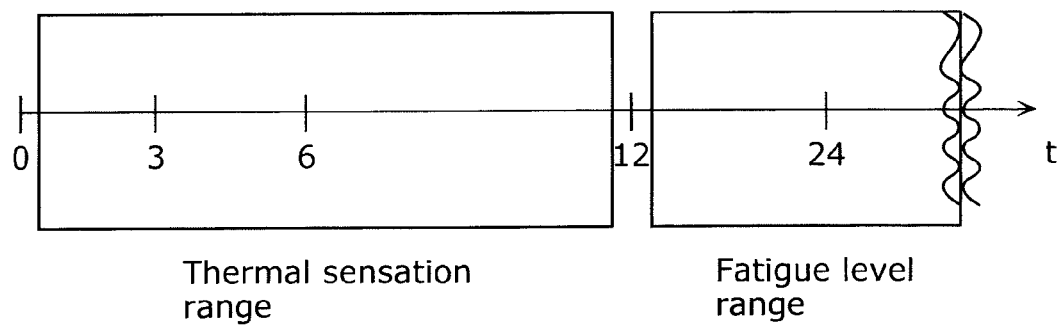
FIG. 15 is a diagram showing reaction time for thermal sensations and reaction time for fatigue levels.

The environment temperature is constant during a period from 0 to 24 minutes, starts to change at the 24-minute point, increases to the highest temperature at the 51-minute point, and decreases to the lowest temperature at the 105-minute point. Focusing on the thermal sensation, a change occurs approximately after 3 minutes from the 24-minute point (Point 71). In addition, a change occurs approximately after 3 minutes from the 51-minute point (Point 72). Further, a change occurs approximately after 6 minutes from the 105-minute point (Point 73). Likewise, focusing on the fatigue level, a change occurs approximately after 12 minutes from the 24-minute point (Point 74). In addition, a change occurs approximately after 45 minutes from the 51-minute point (Point 75). Further, a change occurs approximately after 24 minutes from the 105-minute point (Point 76). To sum up, the thermal sensation level responds to a temperature change in a shorter time than in the fatigue level. More specifically, as shown in FIG. 15, the thermal sensation level starts to change approximately within 12 minutes in response to the temperature change, whereas the fatigue level starts to change approximately after 12 minutes or more in response to the temperature change.

For this reason, setting a threshold value for the change time from the starting point within 6 to 12 minutes inclusive enables the most appropriate discrimination between the thermal sensation and fatigue level. Therefore, the threshold value for the change time from the starting point is determined to be 10 minutes in this embodiment.

Next, detailed descriptions are given of a measurement and accumulation process (S1 in FIG. 11) for the time-series pulse wave data performed by the vital sign measurement unit 101.

Figure 17:
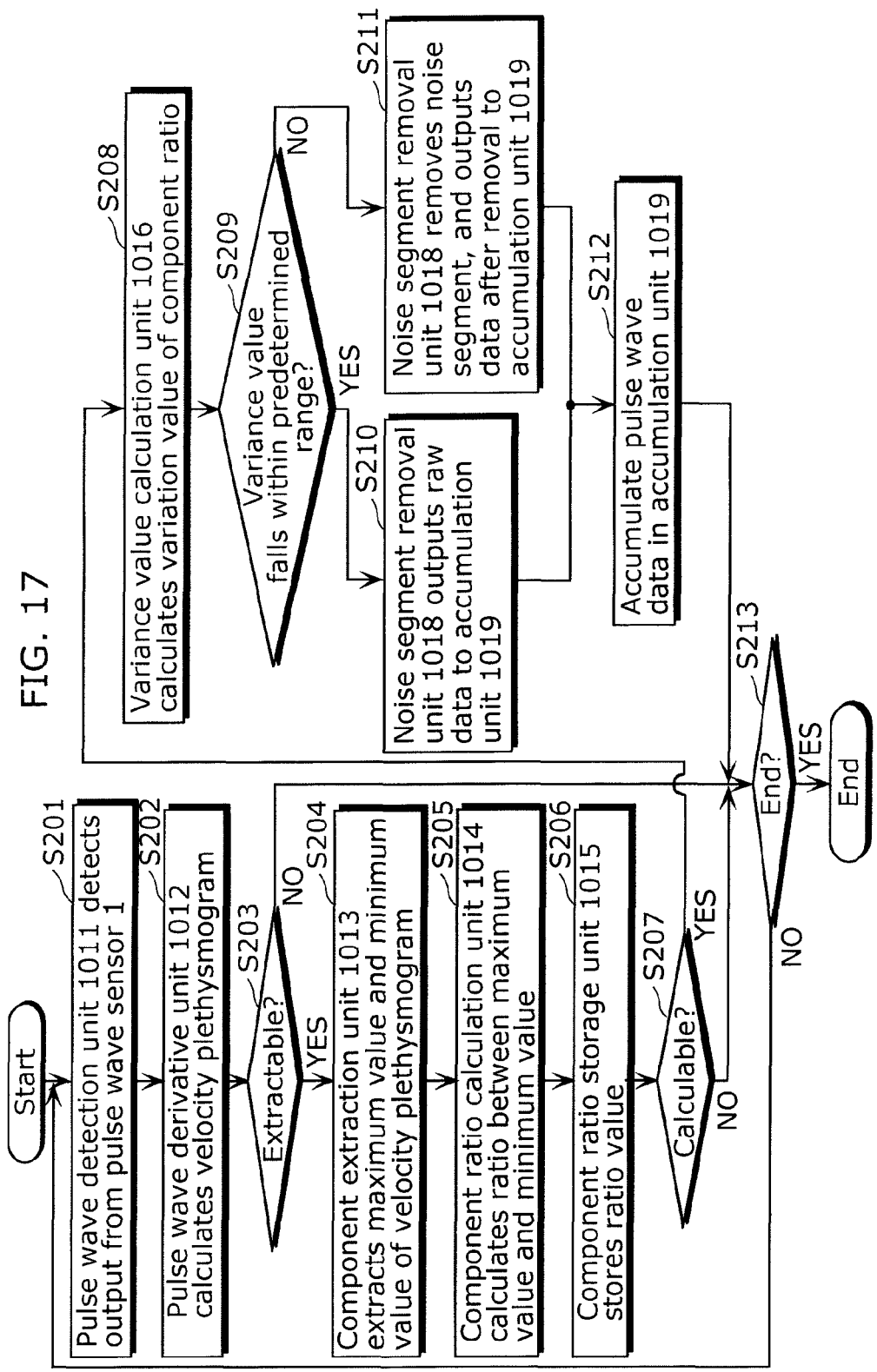
FIG. 17 is a flowchart of processing performed by the vital sign measurement unit.

FIG. 17 is a flowchart of processing performed by the vital sign measurement unit 101.

The pulse wave detection unit 1011 detects an output signal from the pulse wave sensor 1 as a pulse wave (S201). The pulse wave derivative unit 1012 calculates velocity plethysmogram by performing first-order derivative on the pulse wave detected by the pulse wave detection unit 1011, and stores the velocity plethysmogram in an external memory (S202).

Next, the component extraction unit 1013 checks whether or not the maximum value and the minimum value can be extracted from the velocity plethysmogram calculated by the pulse wave derivative unit 1012 (S203). When the maximum value and the minimum value cannot be extracted from the velocity plethysmogram (NO in S203), the vital sign measurement unit 101 checks whether or not the vital sign measurement unit 101 satisfies a condition for terminating the current processing (the condition is, for example, an elapse of a specified time and an End operation) (S213), and terminates the processing in the case where the termination condition is satisfied (YES in S213). In the case where the termination condition is not satisfied (NO in S213), the pulse wave detection unit 1011 continues the pulse wave detection process (S201). On the other hand, when the maximum value and the minimum value can be extracted from the velocity plethysmogram (YES in S203), the component extraction unit 1013 extracts the maximum value and the minimum value of the velocity plethysmogram within the predetermined time range (S204).

Figure 18:
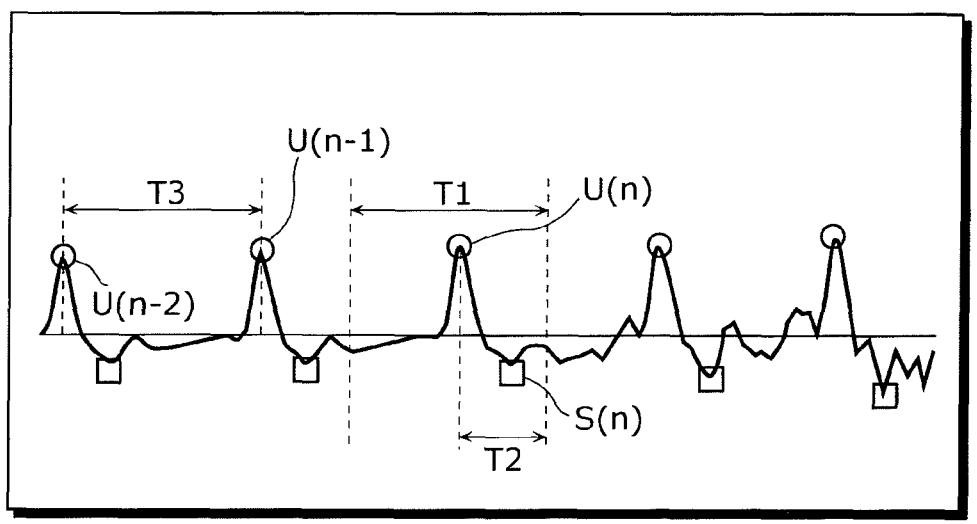
FIG. 18 is a diagram of a waveform representing temporal changes in a velocity plethysmogram.

Here, a description is given of the process (S204) for extracting the maximum value and the minimum value performed by the component extraction unit 1013 with reference to FIG. 18 that is a waveform diagram showing temporal changes in the velocity plethysmogram. In the waveform diagram of FIG. 18, the horizontal axis shows time, and the vertical axis shows the magnitude of the velocity plethysmogram.

The component extraction unit 1013 extracts, as the maximum value of the velocity plethysmogram, the maximum wave height value (U(n) in FIG. 18) in the predetermined time range (T1 in FIG. 18) of the velocity plethysmogram. In addition, the component extraction unit 1013 extracts, as the minimum value of the velocity plethysmogram, the minimum wave height value (S(n) in FIG. 18) in a time range temporally backward of the point (U(n) in FIG. 18) at which the maximum value has been extracted. It is also good to set the predetermined time range (T1 in FIG. 18) within a time range corresponding to a pulse in the case where the number of pulses per 1 minute is 60, or to dynamically change to the interval (T3 in FIG. 18) between two consecutive maximum values calculated immediately before. In addition, it is also good to calculate the average value of the intervals between plural maximum values, and dynamically change to the average value. In addition, the determination process (S203) for determining whether or not the maximum value and the minimum value of the velocity plethysmogram can be extracted is performed depending on whether or not the velocity plethysmogram which include all data items in the predetermined time range (T1 in FIG. 18) has already been calculated.

Next, the component ratio calculation unit 1014 calculates the component ratio by dividing the minimum value by the maximum value (S205). The minimum value and the maximum value are the values extracted by the component extraction unit 1013. The component ratio storage unit 1015 stores the component ratio calculated by the component ratio calculation unit 1014 (S206).

Next, the variance value calculation unit 1016 checks whether or not the variance values of the component ratios stored in the component ratio storage unit 1015 can be calculated (S207). In the case where the variance values of the component ratios cannot be calculated (NO in S207), the vital sign measurement unit 101 checks whether or not a condition for terminating the processing is satisfied (S213). In the case where the termination condition is satisfied (YES in S213), the vital sign measurement unit 101 terminates the processing. In the case where the termination condition is not satisfied (NO in S213), the pulse wave detection unit 1011 continues the pulse wave detection process (S201).

On the other hand, in the case where the variance values of the component ratios can be calculated (YES in S207), the variance value calculation unit 1016 calculates, as indicators, the variance values of the component ratios (S208). Here, it is assumed that the i-th calculated component ratio is F(i), and the number of components F to be used for calculating the variance values is k. The n-th variance value is calculated based on the component ratios from F(n) to F(n+k), and the n+1-th variance value is calculated based on the component ratios from F(n+1) to F(k+n+1) shifted by 1 from the respective components ratios used for the n-th variance value. It is also good to calculate the variance values based on the component ratios shifted by k instead of 1. In addition, the process (S207) for determining whether or not the variance values can be calculated is performed depending on whether or not the component ratios stored in the component ratio storage unit 1015 is sufficient in number in order to calculate the variance values.

Next, the determination unit 1017 determines whether or not the variance values calculated by the variance value calculation unit 1016 fall within the range predetermined for variance values (the range is 0.00 to 0.01, for example) (S209). Here, in the case where the variance values fall within the range predetermined for variance values (YES in S209), the determination unit 1017 determines that the detected pulse noise does not include noise, and the noise segment removal unit 1018 outputs the data indicating the pulse wave to the accumulation unit 1019 without performing noise removal (S210).

In contrast, in the case where the variance values do no fall within the range predetermined for variance values (NO in S209), the determination unit 1017 determines that the detected pulse wave includes noise, and the noise segment removal unit 1018 removes the pulse wave portion corresponding to the noise segment and outputs the data indicating the pulse wave which has been subjected to the noise removal to the accumulation unit 1019 (S211).

The accumulation unit 1019 accumulates the pulse wave data outputted by the noise segment removal unit 1018 (S212).

The vital sign measurement unit 101 checks whether or not a condition for terminating the current processing is satisfied (S213). In the case where the termination condition is satisfied (YES in S213), the processing is terminated. In the case where the termination condition is not satisfied (NO in S213), the pulse wave detection unit 1011 continues the pulse wave detection process (S201).

Figure 19:
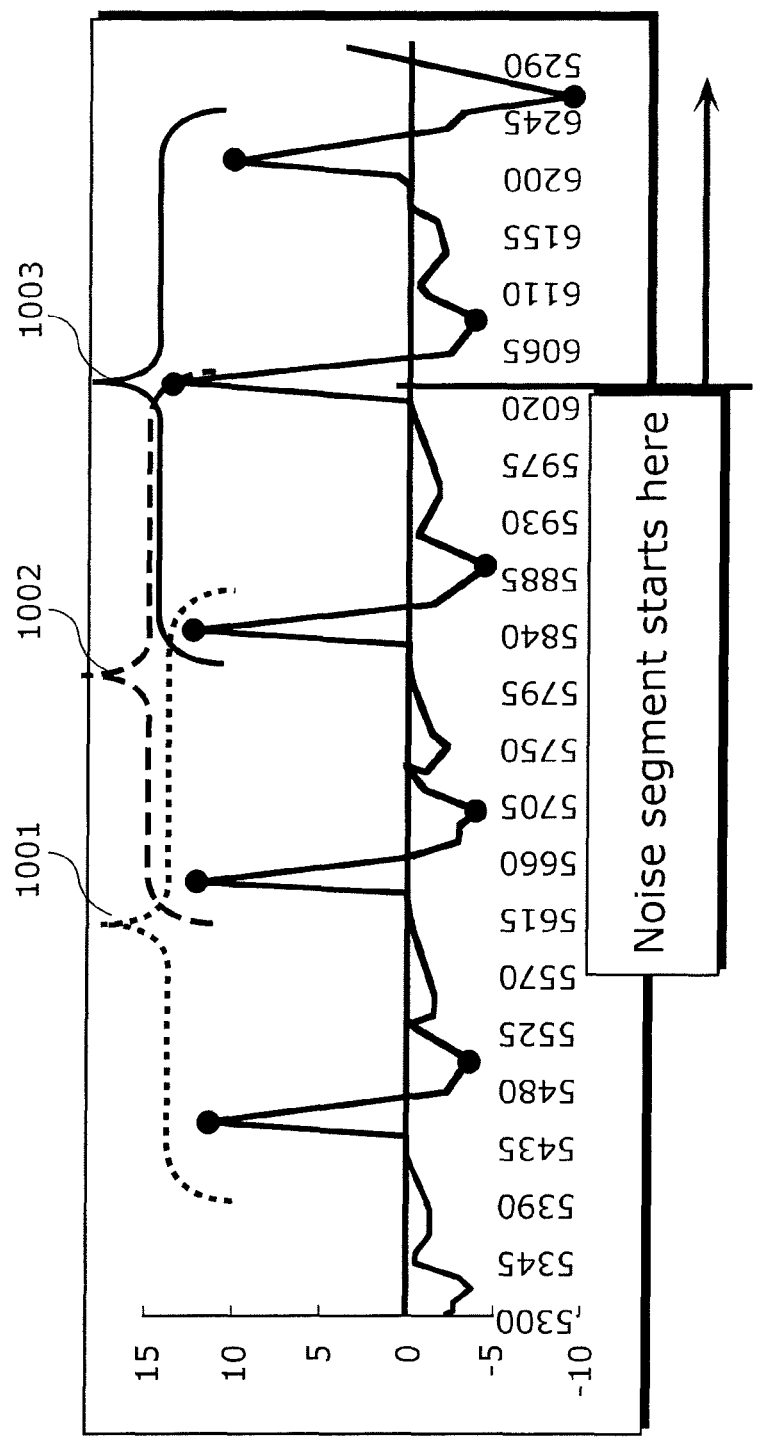
FIG. 19 is a diagram for illustrating the starting position of a noise segment.

Next, a description is given of a noise removal process (S211) performed by the noise segment removal unit 1018. FIG. 19 is a diagram for illustrating the starting position of the noise segment, and FIG. 20 shows a diagram for illustrating the ending position of the noise segment.

Figure 20:
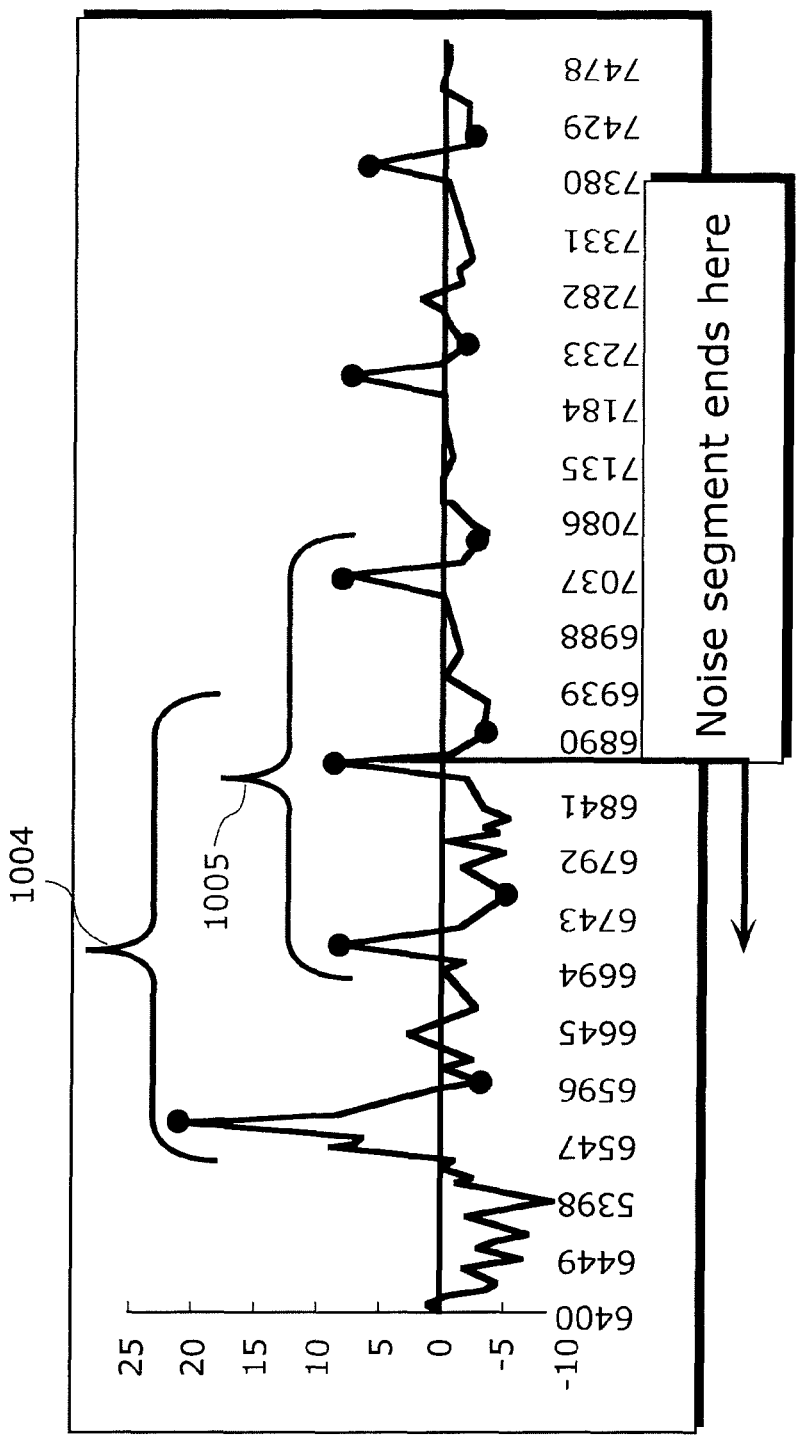
FIG. 20 is a diagram for illustrating the ending position of the noise segment.

Each of FIG. 19 and FIG. 20 is a graph representing the waveform of the velocity plethysmogram. The horizontal axis shows time, and the vertical axis shows the values of velocity plethysmogram. For example, as shown in FIG. 19, it is assumed that the variance value calculation unit 1016 calculates the variance value in each of the consecutive time segments 1001, 1002, and 1003. In addition, it is assumed that the variance value in each of the time segments is calculated based on three temporally consecutive component ratios. Here, it is assumed that the variance values in the respective time segments 1001 and 1002 fall within the range predetermined for variance values, and the variance value in the time segment 1003 does not fall within the range predetermined for variance values. In this case, for example, the noise segment removal unit 1018 determines, as the starting position of the noise segment, the position of the second component ratio (in the diagram, the position indicates the corresponding velocity plethysmogram) among the three component ratios included in the time segment 1003.

In addition, as shown in FIG. 20, it is assumed that the variance value calculation unit 1016 calculates the variance values in the consecutive time segments 1004 and 1005. In addition, it is assumed that the variance value in each of the time segments is calculated based on three temporally consecutive component ratios. Here, it is assumed that the variance value in the time segment 1004 does not fall within the range predetermined for variance values, and the variance value in the time segment 1005 falls within the range predetermined for variance values. In addition, it is assumed that the variance values in the time segments prior to the time segment 1004 do not fall within the range predetermined for the variance values. In this case, for example, the noise segment removal unit 1018 determines, as the ending position of the noise segment, the position of the second component ratio (in the diagram, the position indicates the corresponding velocity plethysmogram) among the three component ratios included in the time segment 1005.

It is to be noted that the method for determining the starting position and the ending position of the noise segment is not limited to this. For example, it is also good to determine, as the starting position of the noise segment, the position of the first component ratio or the position of the third component ratio in the time segment determined to be outside the range predetermined for variance values. Otherwise, it is also good to determine, as the ending position of the noise segment, the position of the first component ratio or the position of the third component ratio in the time segment determined to be within the range predetermined for variance values. Further, the number of component ratios used for calculating a variance value is not limited to three, any other number is possible.

Figure 21:
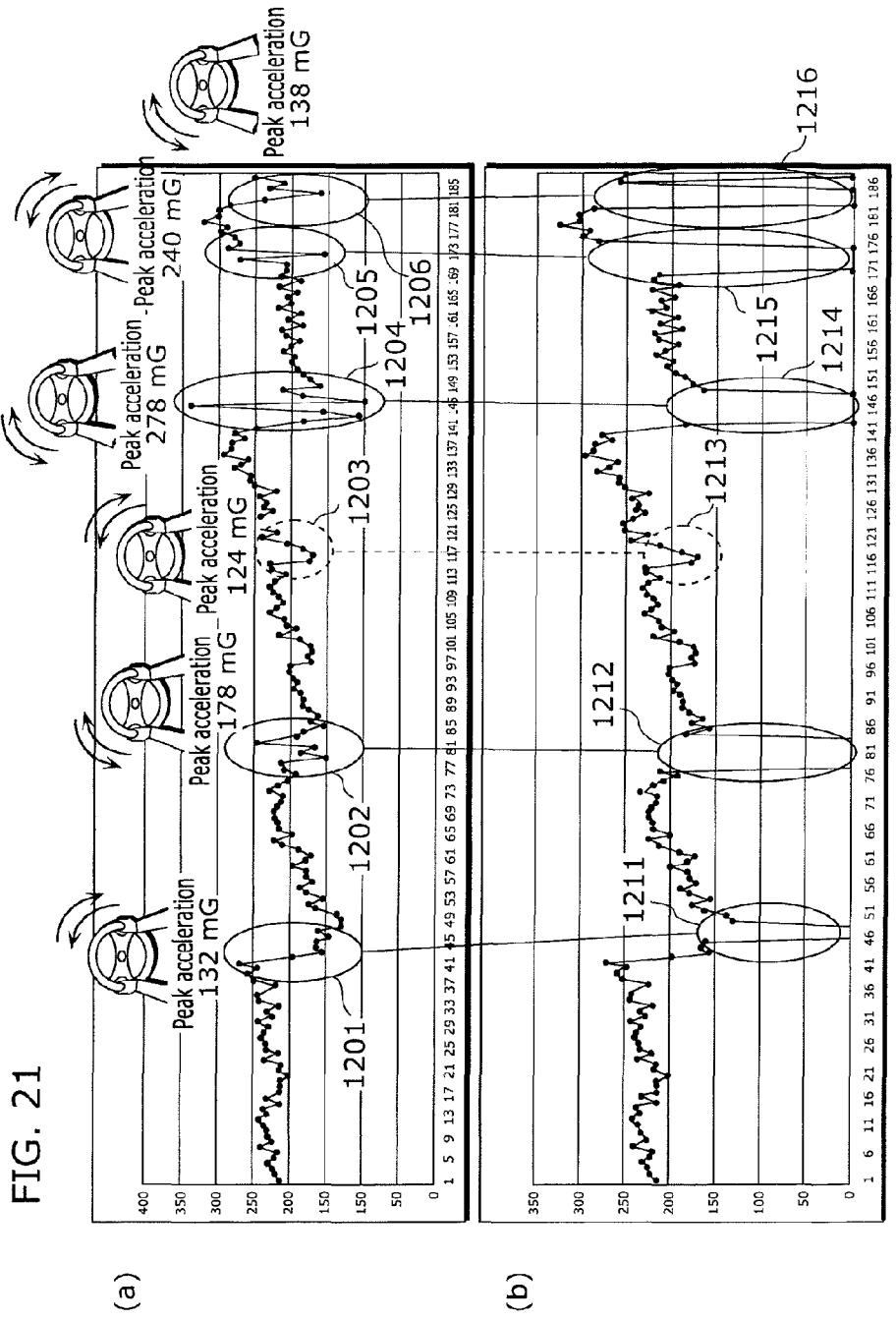
FIG. 21 is a diagram for illustrating removal of noise from pulse wave data.

FIG. 21 is a diagram for illustrating removal of noise from pulse wave data. FIG. 21(*a*) is a graph representing temporal changes in the amplitude value of Wave a (described later) that is a first wave of the accelerated plethysmogram which has not yet been subjected to noise removal. FIG. 21(*b*) is a graph representing temporal changes in the amplitude value of Wave a in the accelerated plethysmogram which has been subjected to the noise removal. In each graph, the horizontal axis shows time, and the vertical axis shows the amplitude values of Wave a in the accelerated plethysmogram.

Here, it is assumed that the pulse wave of a car driver is being measured. It is assumed that the handle has been operated in Segments 1201 to 1206 shown in FIG. 21(*a*), with body movements. The diagram shows the reached maximum acceleration (x-y two axis resultant force) at the time of the handle operation, and the reached maximum acceleration in Segment 1201 is 132 mG, for example. Due to such body movements, the amplitude values of Wave a vary. This results in variance in component ratios. Accordingly, as shown in FIG. 21(*b*), noise is removed from Segments 1211, 1212, and

1214 to 1216 respectively corresponding to Segments 1201, 1202, and 1204 to 1206. The variance value (variance value of component ratios) of the amplitude values of Wave a in Segment 1203 is smaller than those in the other segments. Thus, Segment 1213 corresponding to Segment 1203 is not regarded as a noise segment, and no noise removal is performed on Segment 1213. The example in FIG. 21 shows temporal changes in the amplitude values of Wave a in the accelerated plethysmogram. Likewise, noise removal is performed on the corresponding positions of the pulse wave data.

As shown in FIG. 21, it is also good to perform noise removal shifting the ending position of the noise segment by several to 10 seconds because it takes a certain time for the blood flow to return immediately after the noise segment.

Figure 22:
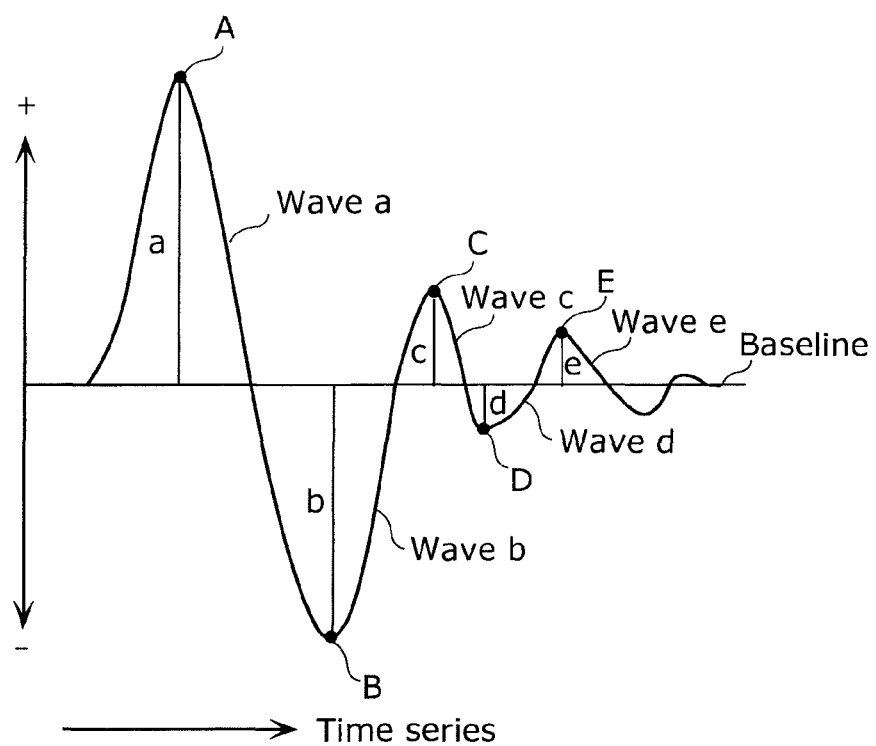
FIG. 22 is a diagram showing an exemplary waveform of the velocity plethysmogram.

Next, a description is given of Wave a of the accelerated plethysmogram. FIG. 22 is a diagram showing an example of the waveform of the velocity pulse wave. The accelerated plethysmogram includes Wave a, Wave b, Wave c, Wave d, and Wave e. The apex A of Wave a matches the starting point of the diastolic wave of the finger-tip plethysmogram (abbreviated as PTG), and thus the required time from Apex A to Apex E matches the length of systolic time axis of the user's heart. Wave a is a positive wave that is upwardly convex with respect to the baseline, and Wave b is a negative wave that is downwardly convex with respect to the baseline. Wave c, Wave d, and Wave e are element waves that change between positive and negative depending on user's physiological conditions, and are highly correlated with the user's age.

According to the method described above, the parameter extraction unit 102 extracts parameter vales which have been subjected to the noise removal. The parameter change amount calculation unit 103 calculates the change amount from the starting point and the previous change amount based on the parameter values which have been subjected to the noise removal. For example, it is also good to calculate the change amount from the starting point only when the parameter values at the starting time point and the current time point have been obtained, and to calculate the previous change amount only when the parameter values at the previous continuation time point and the parameter values at the current time point have been obtained. In addition, it is good to calculate the change amount from the starting point only when parameter values corresponding to a predetermined ratio (50%, for example) or more have been obtained at the measurement time points of the parameter values between the starting time point and the current time point, and to omit calculation of a change amount from the starting point in the other cases.

As described above, with the device control device according to Embodiment 1, when a user's pulse wave changes, it is possible to determine the factor of the change in the pulse wave taking into account the time required for the change in addition to the change amount in the pulse wave. In other words, it is possible to discriminate the factor of the change in the pulse wave, that is, determine whether the change is due to a change in the user's thermal sensation or a change in the user's health condition. In addition, it is also possible to evaluate the user's thermal sensation or health condition based on the factor of the change. This prevents device control based on an erroneous evaluation result in the system for obtaining the user's pulse wave and feeding back information about the pulse wave, and makes it possible to reliably present the user status and perform device control to make better the user status.

In addition, in this Embodiment, it is possible to discriminate a change in the pulse wave made due to a change in the user's thermal sensation from noise caused due to the influence of body movements by calculating the variance value of the component ratios based on the maximum value and minimum value in each predetermined time range of the accelerated plethysmogram and determining whether or not the variance value falls within a range predetermined for variance values.

Embodiment 2

The following description is given of a device control device according to Embodiment 2 of the present invention. The same elements as those of the device control device according to Embodiment 1 are assigned with the same numerical references. The functions and names are also the same, and thus no detailed descriptions are repeated here.

Figure 23:
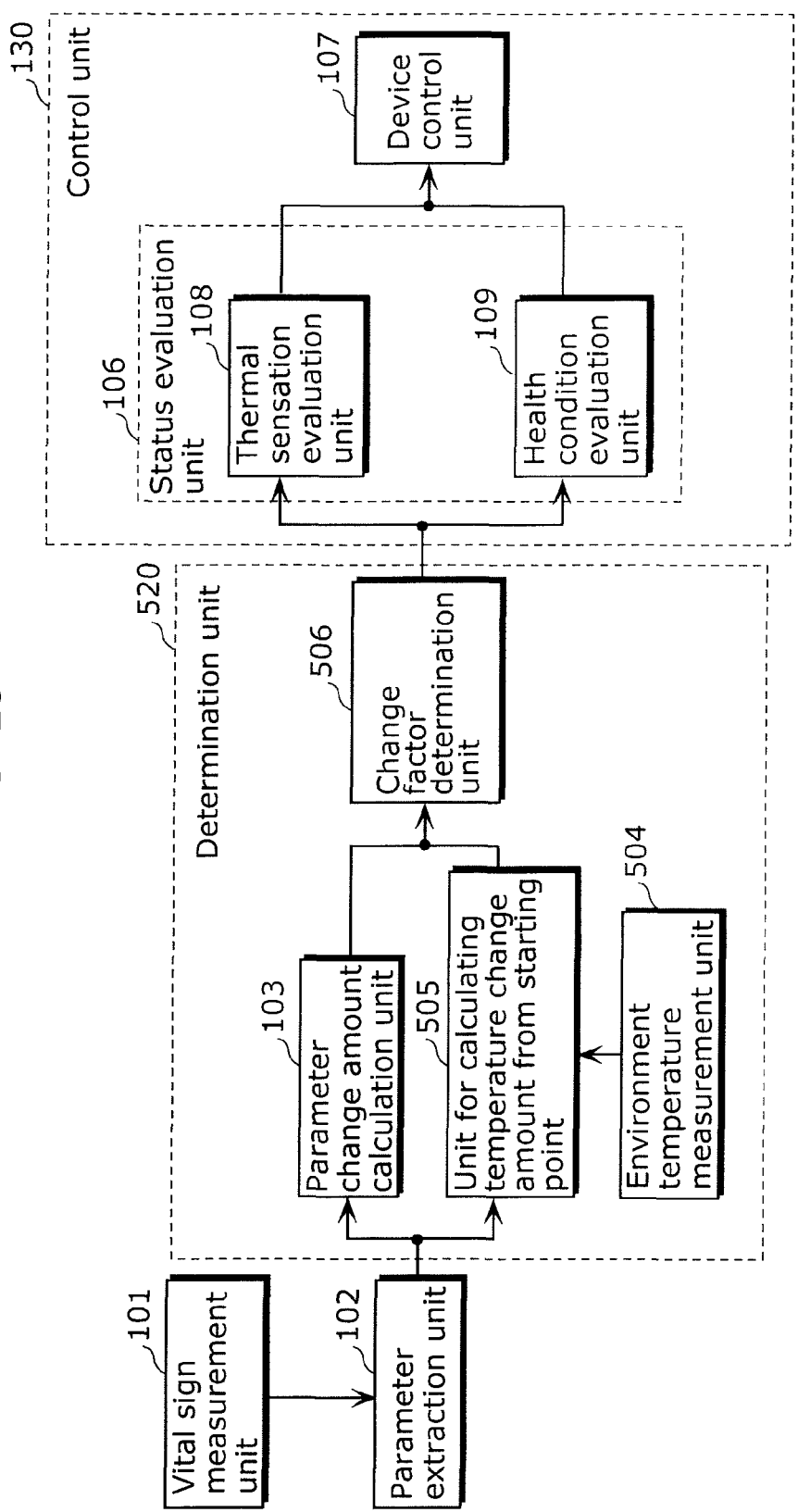
FIG. 23 is a block diagram showing the structure of a device control device according to Embodiment 2 of the present invention.

FIG. 23 is a block diagram showing the structure of a device control device according to Embodiment 2 of the present invention. The device control device shown in FIG. 23 is configured with known computers for example, and includes a vital sign measurement unit 101, a parameter extraction unit 102, a determination unit 520, and a control unit 130. These processing units function when the program is executed by a CPU of a computer storing an installed device control program designed according to this embodiment.

The determination unit 520 is a processing unit for determining the factor of a change in the pulse wave data using parameter values extracted by the parameter extraction unit 102. The determination unit 520 includes a parameter change amount calculation unit 103, an environment temperature measurement unit 504, a unit 505 for calculating a temperature change amount from a starting point, and a change factor determination unit 506.

The environment temperature measurement unit 504 measures and accumulates environment temperature data. The unit 505 for calculating a temperature change amount from a starting point calculates, as a change amount from a starting point, the difference between the value at a predetermined starting time point and the value at a current time point in the environment temperature data measured by the environment temperature measurement unit 504, and outputs the current change amount from the starting point to the change factor determination unit 506.

The change factor determination unit 506 determines the factor of the change in the pulse wave amplitude (the factor is, for example, the influence of a thermal sensation or the influence of a health condition), based on (i) the change amount from the starting point calculated by the parameter change amount calculation unit 103 and (ii) the temperature change amount from the starting point calculated by the unit 505 for calculating a temperature change amount from the starting point. Based on the determined factor, the change factor determination unit 506 selects the best evaluation unit from among the thermal sensation evaluation unit 108 and the health condition evaluation unit 109 included in the status evaluation unit 106, and outputs, to the selected evaluation unit, the current change amount from the starting point that is information to be used for evaluating the current status.

Next, a description is given of processing performed by the device control device according to Embodiment 2.

Figure 24:
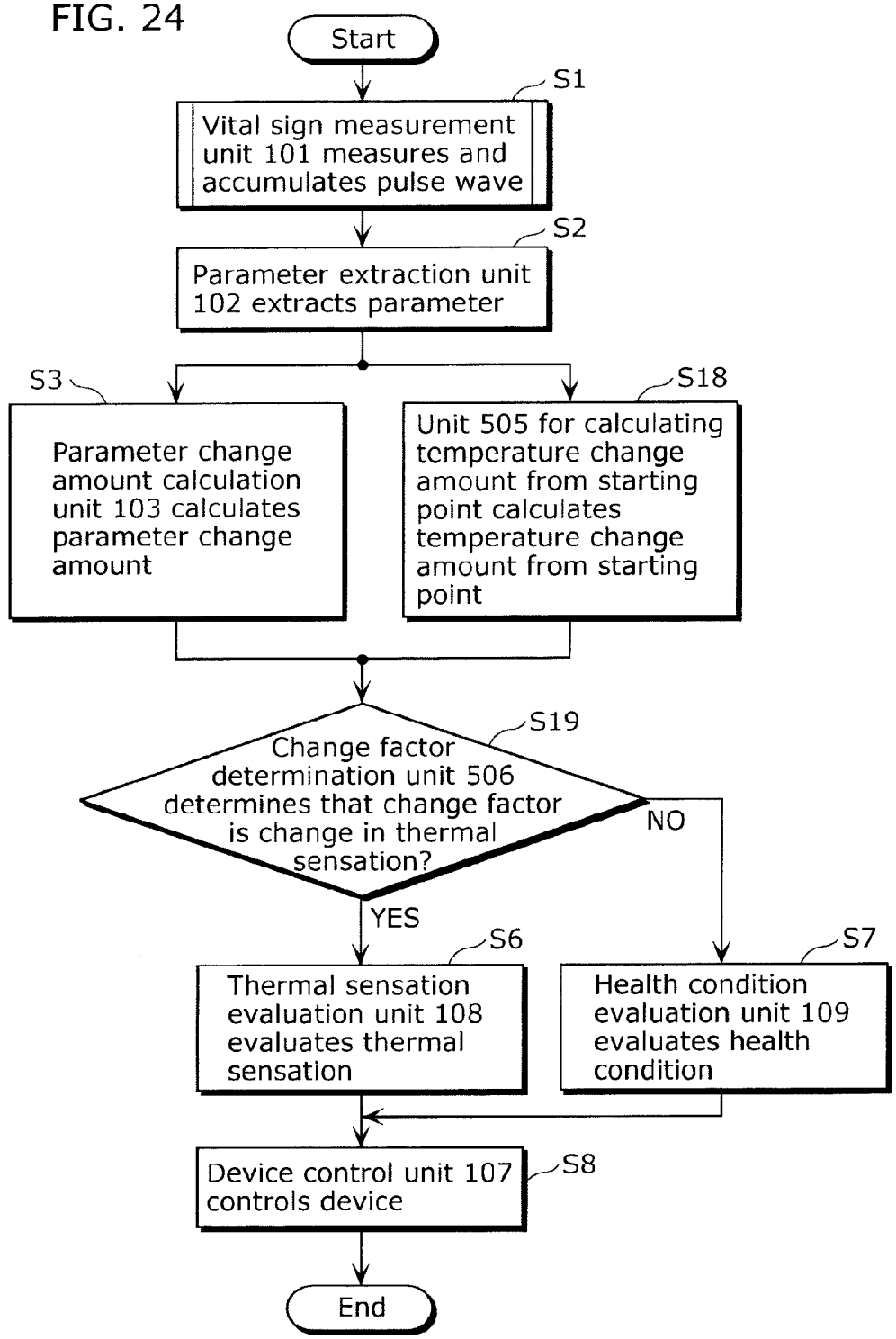
FIG. 24 is a flowchart of processing performed by the device control device according to Embodiment 2 of the present invention.

FIG. 24 is a flowchart of processing performed by the device control device according to Embodiment 2 of the present invention.

The device control device executes the processes from S1 to S3 as in Embodiment 1.

On the other hand, the unit 505 for calculating a temperature change amount from a starting point calculates, as the change amount from the starting point, the difference between the value at a predetermined starting time point and the value at a current time point in the environment temperature data measured by the environment temperature measurement unit 504, and outputs the current change amount from the starting point to the change factor determination unit 506 (S18).

The change factor determination unit 506 determines the factor of the change in the pulse wave amplitude based on the change amount from the starting point calculated by the parameter change amount calculation unit 103 and the temperature change amount from the starting point outputted by the unit 505 for calculating a temperature change amount from a starting point (S19). When the change factor determination unit 506 determines that the factor of the change is a change in the thermal sensation (YES in S19), it outputs, to the thermal sensation evaluation unit 108, the current change amount from the starting point that is information to be used for evaluating the thermal sensation. When the change factor determination unit 506 determines that the factor of the change is a change in the health condition (NO in S19), it outputs, to the health condition evaluation unit 109, the current change amount from the starting point that is information to be used for evaluating the health condition. This determination process (S19) is described later in detail.

Subsequently, the device control device performs device control by executing the processes from S6 to S8 as in Embodiment 1.

Figure 25:
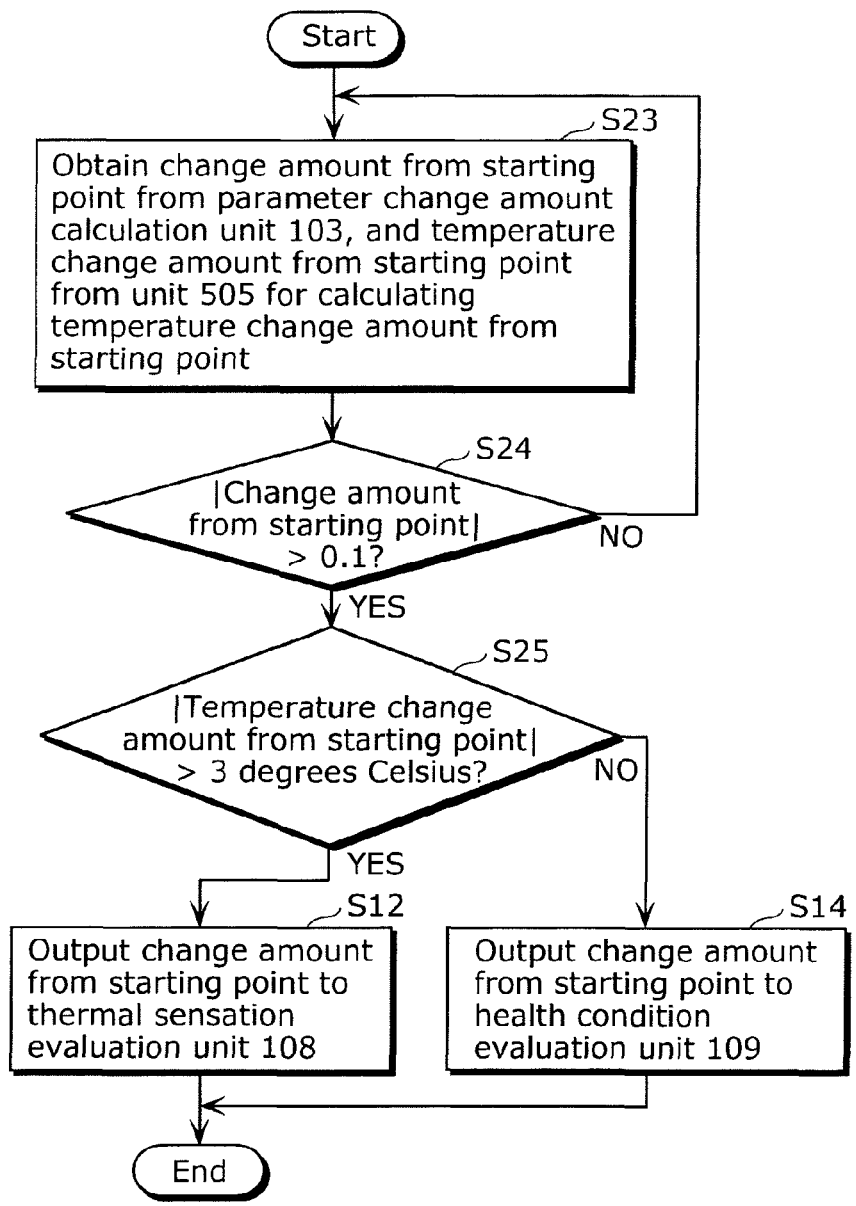
FIG. 25 is a flowchart of processing performed by a change factor determination unit according to Embodiment 2 of the present invention.

Next, a detailed description is given of a determination process (S19 in FIG. 24) for determining the factor of the change in the pulse wave amplitude made by the change factor determination unit 506. FIG. 25 is a flowchart of processing performed by the change factor determination unit 506 according to Embodiment 2 of the present invention. In addition, FIG. 26 is a diagram showing a data table used for determining the factor of the change in the amplitude of the pulse wave stored in the change factor determination unit 506. The processing shown in FIG. 25 is described below based on the contents of the data table shown in FIG. 26.

First, the change factor determination unit 506 obtains the change amount from the starting point from the parameter change amount calculation unit 103, and obtains the temperature change amount from the starting point from the unit 505 for calculating the temperature change amount from the starting point (S23). The change factor determination unit 506 determines whether or not the absolute value of the change amount from the starting point is greater than a predetermined numerical value (0.1) (S24). When the absolute value of the change amount from the starting point is greater than 0.1 (YES in S24), the change factor determination unit 506 determines whether or not the absolute value of the temperature change amount from the starting point is greater than the predetermined numerical value (3 degrees Celsius) (S25). When the absolute value of the change amount from the starting point is not greater than 0.1 (NO in S24), the change factor determination unit 506 waits until the next change amount from the starting point and the temperature change amount from the starting point are obtained, and repeats the processing from S23.

When the absolute value of the temperature change amount from the starting point is greater than 3 degrees Celsius (YES in S25), the change factor determination unit 506 determines that the factor of the change in the amplitude of the pulse wave as shown in FIG. 26 is a change in the thermal sensation, and outputs, to the thermal sensation evaluation unit 108, the current change amount from the starting point that is information to be used for evaluating the thermal sensation (S12). When the absolute value of the temperature change amount from the starting point is not greater than 3 degrees Celsius (NO in S25), the change factor determination unit 506 determines that the factor of the change in the amplitude of the pulse wave as shown in FIG. 26 is a change in the health condition, and outputs, to the health condition evaluation unit 109, the current change amount from the starting point that is information to be used for evaluating the health condition (S14).

Next, a description is given of why 3 degrees Celsius is determined as the threshold value for the temperature change time from the starting point in the data table shown in FIG. 26.

For example, compared to the thermal sensation at 24-minute time point, the thermal sensation changes significantly for the first time at Point 71. The change amount from the temperature at the 24-minute time point from the time point 71 is approximately 0.5 degrees Celsius. On the other hand, compared to the fatigue level at the 24-minute time point, the fatigue level changes significantly for the first time at Point 74. The change amount from the temperature at the 24-minute time point from the time point 74 is approximately 3.6 degrees Celsius. In other words, the thermal sensation is more susceptible to the temperature change than the fatigue level, and the border is determined to be a range between 0.5 degrees Celsius and 3.6 degrees Celsius inclusive.

For this reason, as shown in FIG. 27, setting a threshold value for the temperature change amount from the starting point within 1 to 3 degrees Celsius enables the most appropriate discrimination between the thermal sensation and the fatigue level. Therefore, the threshold value for the temperature change amount from the starting point is determined to be 3 degrees Celsius in this embodiment.

As described above, with the device control device according to Embodiment 2, when a user's pulse wave changes, it is possible to determine the factor of the change in the pulse wave taking into account the change amount in the environment temperature in addition to the change amount in the pulse wave. In other words, it is possible to discriminate the factor of the change in the pulse wave, that is, determine whether the change is due to a change in the thermal sensation or a change in the health condition. In addition, it is also possible to evaluate the user's thermal sensation or health condition based on the change factor. This prevents device control based on an erroneous evaluation result in the system for obtaining the user's pulse wave and feeding back information about the pulse wave, and makes it possible to reliably present the user status and perform device control to make better the user status.

Embodiment 3

The following description is given of a device control device according to Embodiment 3 of the present invention. The same elements as those of the device control device according to Embodiment 1 are assigned with the same numerical references. The functions and names are also the same, and thus no detailed descriptions are repeated here.

Figure 28:
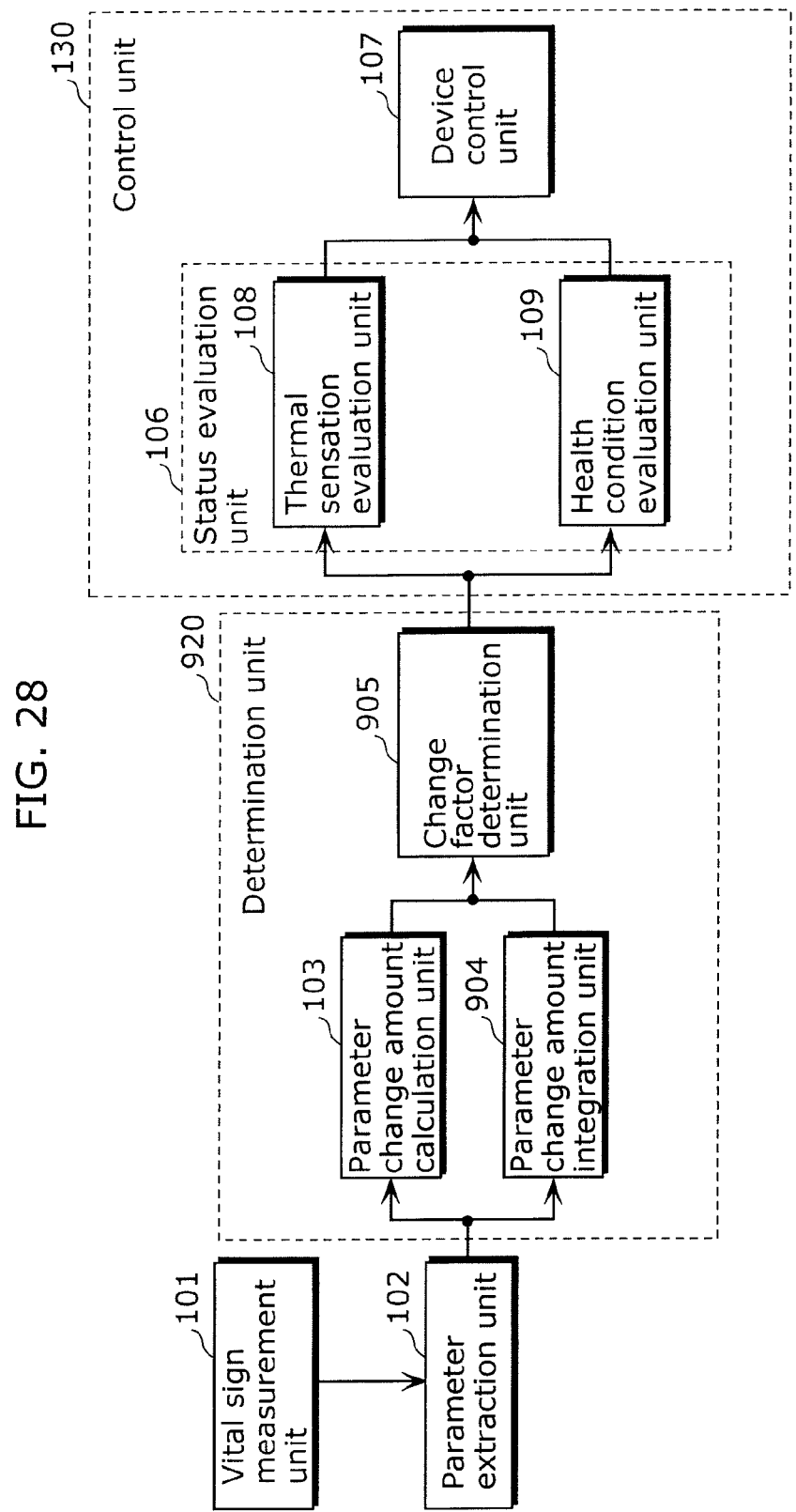
FIG. 28 is a block diagram showing the structure of a device control device according to Embodiment 3 of the present invention.

FIG. 28 is a block diagram showing the structure of a device control device according to Embodiment 3 of the present invention. The device control device shown in FIG. 28 is configured with known computers for example, and includes a vital sign measurement unit 101, a parameter extraction unit 102, a determination unit 920, and a control unit 130. These processing units function when the program is executed by a CPU of a computer storing an installed device control program designed according to this embodiment.

The determination unit 920 is a processing unit for determining the factor of a change in the pulse wave data using parameter values extracted by the parameter extraction unit 102. The determination unit 120 includes a parameter change amount calculation unit 103, a parameter change amount integration unit 904, and a change factor determination unit 905.

The parameter change amount integration unit 904 calculates, as an integration value of change amounts each from a point immediately before a current point (a previous point), an integration value of the change amounts from a predetermined starting time point to a current time point in the time-series data of the pulse wave amplitude extracted by the parameter extraction unit 102, and outputs, to the change factor determination unit 905, the integration value of the change amounts each from the previous point.

The change factor determination unit 905 determines the factor of the change in the pulse wave amplitude (the factor is, for example, the influence of a thermal sensation or the influence of a health condition), based on (i) the change amount from the starting point calculated by the parameter change amount calculation unit 103 and (ii) the integration value of the change amounts each from the previous point calculated by the parameter change amount integration unit 904. Based on the determined factor, the change factor determination unit 905 selects the best evaluation unit from among the thermal sensation evaluation unit 108 and the health condition evaluation unit 109 included in the status evaluation unit 106, and outputs, to the selected evaluation unit, the current change amount from the starting point that is information to be used for evaluating the current status.

Next, a description is given of processing performed by the device control device according to Embodiment 3.

Figure 29:
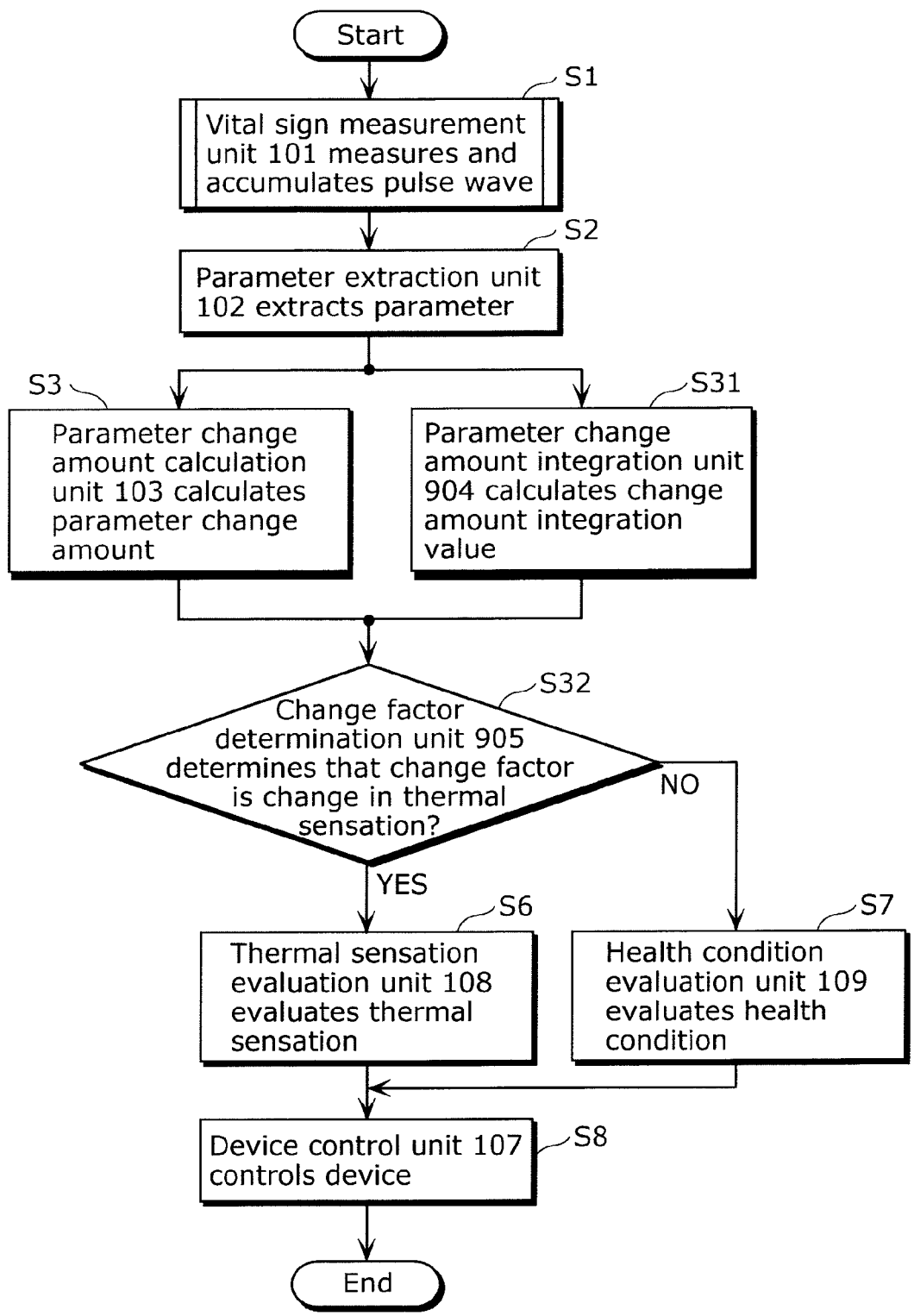
FIG. 29 is a flowchart of processing performed by the device control device according to Embodiment 3 of the present invention.

FIG. 29 is a flowchart of processing performed by the device control device according to Embodiment 3 of the present invention.

The device control device executes the processes from S1 to S3 as in Embodiment 1.

Meanwhile, the parameter change amount integration unit 904 calculates, as an integration value of change amounts each from the previous point, an integration value of the change amounts from a predetermined starting time point to a current time point in the time-series data of the pulse wave amplitude extracted by the parameter extraction unit 102, and output, to the change factor determination unit 905, the integration value of the change amounts each from the previous point (S31).

The change factor determination unit 905 determines the factor of the change in the pulse wave amplitude based on (i) the change amount from the starting point outputted by the parameter change amount calculation unit 103 and (ii) the integration value of the change amounts each from the previous point outputted by the parameter change amount integration unit 904 (S32). When the change factor determination unit 905 determines that the factor of the change is a change in the thermal sensation (YES in S32), it outputs, to the thermal sensation evaluation unit 108, the current change amount from the starting point that is information to be used for evaluating the thermal sensation. When the change factor determination unit 905 determines that the factor of the change is a change in the health condition (NO in S32), it outputs, to the health condition evaluation unit 109, the current change amount from the starting point that is information to be used for evaluating the health condition. This determination process (S32) is described later in detail.

Subsequently, the device control device performs device control by executing the processes from S6 to S8 as in Embodiment 1.

Figure 30:
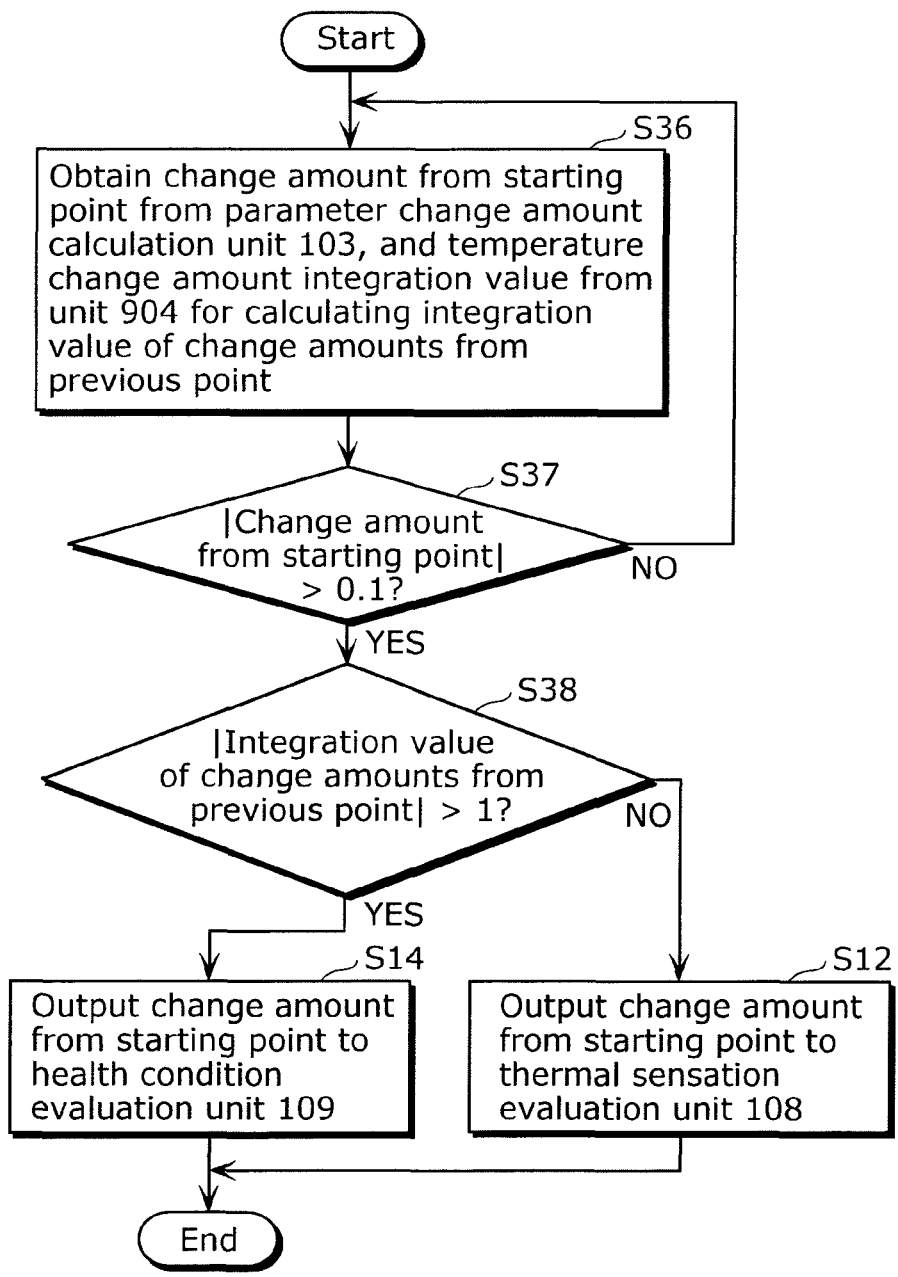
FIG. 30 is a flowchart of processing performed by the change factor determination unit according to Embodiment 3 of the present invention.

Next, a detailed description is given of a determination process (S32 in FIG. 29) that the change factor determination unit 905 performs to determine the factor of the change in the pulse wave amplitude. FIG. 30 is a flowchart of processing performed by the change factor determination unit 905 according to Embodiment 3 of the present invention. In addition, FIG. 31 is a diagram showing a data table used for determining the factor of the change in the amplitude of the pulse wave stored in the change factor determination unit 905. The processing shown in FIG. 30 is described below based on the contents of the data table shown in FIG. 31.

First, the change factor determination unit 905 obtains the change amount from the starting point from the parameter change amount calculation unit 103, and obtains the integration value of the change amounts each from the previous point from the parameter change amount integration unit 904 (S36). The change factor determination unit 905 determines whether or not the absolute value of the change amount from the starting point is greater than a predetermined numerical value (0.1) (S37). When the absolute value of the change amount from the starting point is greater than 0.1 (YES in S37), the change factor determination unit 905 determines whether or not the integration value of the change amounts each from the previous point is greater than a predetermined numerical value (1) (S38). When the absolute value of the change amount from the starting point is not greater than 0.1 (NO in S37), the change factor determination unit 905 waits until the next change amount from the starting point and the next integration value of the change amounts each from the previous point are obtained, and repeats the processing from S36.

When the integration value of the change amounts each from the previous point is greater than 1 (YES in S38), the change factor determination unit 905 determines that the factor of the change in the pulse wave amplitude is a change in the health condition as shown in FIG. 31, and outputs, to the health condition evaluation unit 109, the current change amount from the starting point that is information to be used for evaluating the health condition (S14). When the integration value of the change amounts each from the previous point is not greater than 1 (NO in S38), the change factor determination unit 905 determines that the factor of the change in the pulse wave amplitude is change in the thermal sensation as shown in FIG. 31, and outputs, to the thermal sensation evaluation unit 108, the current change amount from the starting point that is information to be used for evaluating the thermal sensation (S12).

As described above, with the device control device according to Embodiment 3, when a user's pulse wave changes, it is possible to determine the factor of the change in the pulse wave taking into account the integration value of the change amounts in addition to the change amount in the pulse wave. In other words, it is possible to discriminate the factor of the change in the pulse wave, that is, determine whether the change is due to a change in the thermal sensation or a change in the health condition. In addition, it is also possible to evaluate the user's thermal sensation or health condition based on the change factor. This prevents device control based on an erroneous evaluation result in the system for obtaining the user's pulse wave and feeding back information about the pulse wave, and makes it possible to reliably present the user status and perform device control to make the user status better.

Embodiment 4

The following description is given of a device control device according to Embodiment 4 of the present invention. The same elements as those of the device control device according to Embodiment 1 are assigned with the same numerical references. The functions and names are also the same, and thus no detailed descriptions are repeated here.

The device control device according to Embodiment 4 is intended to control an on-vehicle device.

Figure 32:
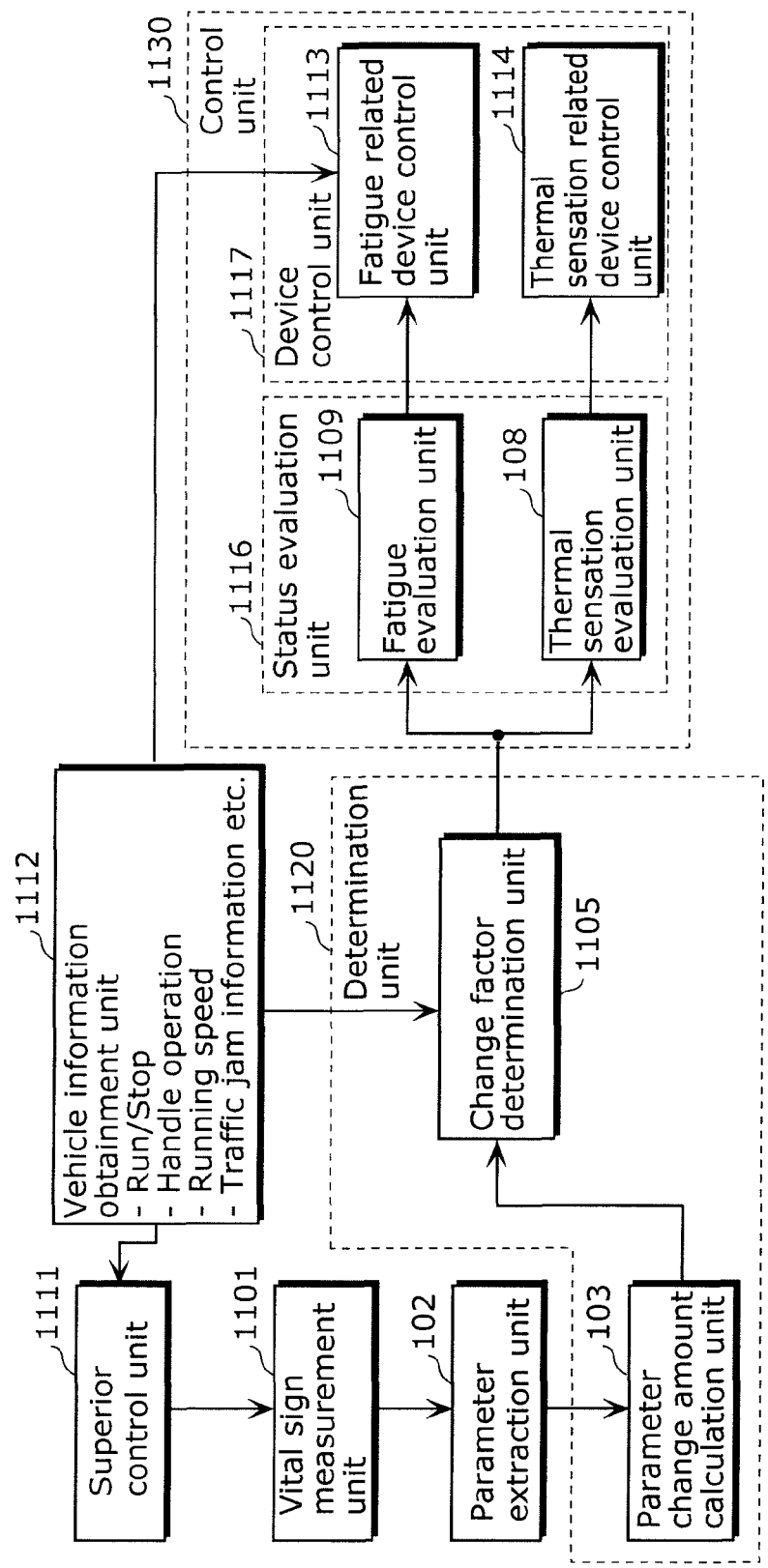
FIG. 32 is a block diagram showing the structure of a device control device according to Embodiment 4 of the present invention.

FIG. 32 is a block diagram showing the structure of the device control device according to Embodiment 4 of the present invention. The device control device shown in FIG. 32 is configured with known computers for example, and includes a superior control unit 1111, a vehicle information obtainment unit 1112, a vital sign measurement unit 1101, a parameter extraction unit 102, a determination unit 1120, and a control unit 1130. These processing units function when the program is executed by a CPU of a computer storing an installed device control program designed according to this embodiment.

The vehicle information obtainment unit 1112 obtains information about the status of a vehicle. The vehicle information obtainment unit 1112 obtains information such as information indicating whether the vehicle is running or stopped, information about handle operations such as handle operation acceleration, the running speed of the vehicle, and traffic jam information.

The superior control unit 1111 directs the vital sign measurement unit 1101 to start and end obtainment of pulse wave data, based on information about the statuses of the vehicle obtained by the vehicle information obtainment unit 1112. For example, the superior control unit 1111 may direct the vital sign measurement unit 1101 to start the obtainment of the pulse wave data when the engine of the vehicle is turned on, and to end the obtainment of the pulse wave data when the engine of the vehicle is turned off.

The vital sign measurement unit 1101 starts and ends the processing under control of the superior control unit 1111. Other than this, the vital sign measurement unit 1101 functions in the same manner as the vital sign measurement unit 101 described in Embodiment 1. In other words, the vital sign measurement unit 1101 obtains time-series pulse wave data of a finger-tip pulse wave of a driver.

The determination unit 1120 is a processing unit for determining the factor of a change in the pulse data using parameter values extracted by the parameter extraction unit 102, and includes the parameter change amount calculation unit 103 and a change factor determination unit 1105.

The change factor determination unit 1105 determines the factor of the change in the pulse wave amplitude (the factor is, for example, the influence of a thermal sensation or the influence of a health condition), based on (i) the change amount from the starting point calculated by the parameter change amount calculation unit 103 and (ii) the information about the status of the vehicle obtained by the vehicle information obtainment unit 1112. Based on the determined factor, the change factor determination unit 1105 selects the best evaluation unit from among a thermal sensation evaluation unit 108 and a fatigue evaluation unit 1109 included in a later-described status evaluation unit 1116, and outputs, to the selected evaluation unit, the current change amount from the starting point that is information to be used for evaluating the current status.

The control unit 1130 is a processing unit for performing device control based on the determination result made by the change factor determination unit 1105, and includes a status evaluation unit 1116 and a device control unit 1117.

The status evaluation unit 1116 is a processing unit for evaluating the status of the driver based on the change amount from the starting point in the pulse wave amplitude outputted by the change factor determination unit 1105, and includes a fatigue evaluation unit 1109 and the thermal sensation evaluation unit 108. The fatigue evaluation unit 1109 evaluates the fatigue level of the user based on the change amount from the starting point in the pulse wave amplitude outputted by the change factor determination unit 1105, and outputs the evaluation result to a later-described fatigue related device control unit 1113 of the control unit 1130. The thermal sensation evaluation unit 108 evaluates the user's thermal sensation based on the change amount from the starting point in the pulse wave amplitude outputted by the change factor determination unit 1105, and outputs the evaluation result to a later-described thermal sensation related device control unit 1114 included in the control unit 1130.

The device control unit 1117 is a processing unit for controlling an on-vehicle device based on the evaluation result made by the fatigue evaluation unit 1109 or the thermal sensation evaluation unit 108, and includes the fatigue related device control unit 1113 and the thermal sensation related device control unit 1114. The fatigue related device control unit 1113 performs device control for lowering the fatigue level of the driver based on the driver's fatigue level evaluated by the fatigue evaluation unit 1109. Based on the driver's thermal sensation evaluated by the thermal sensation evaluation unit 108, the thermal sensation related device control unit 1114 performs device control for making better the driver's thermal sensation.

Figure 33:
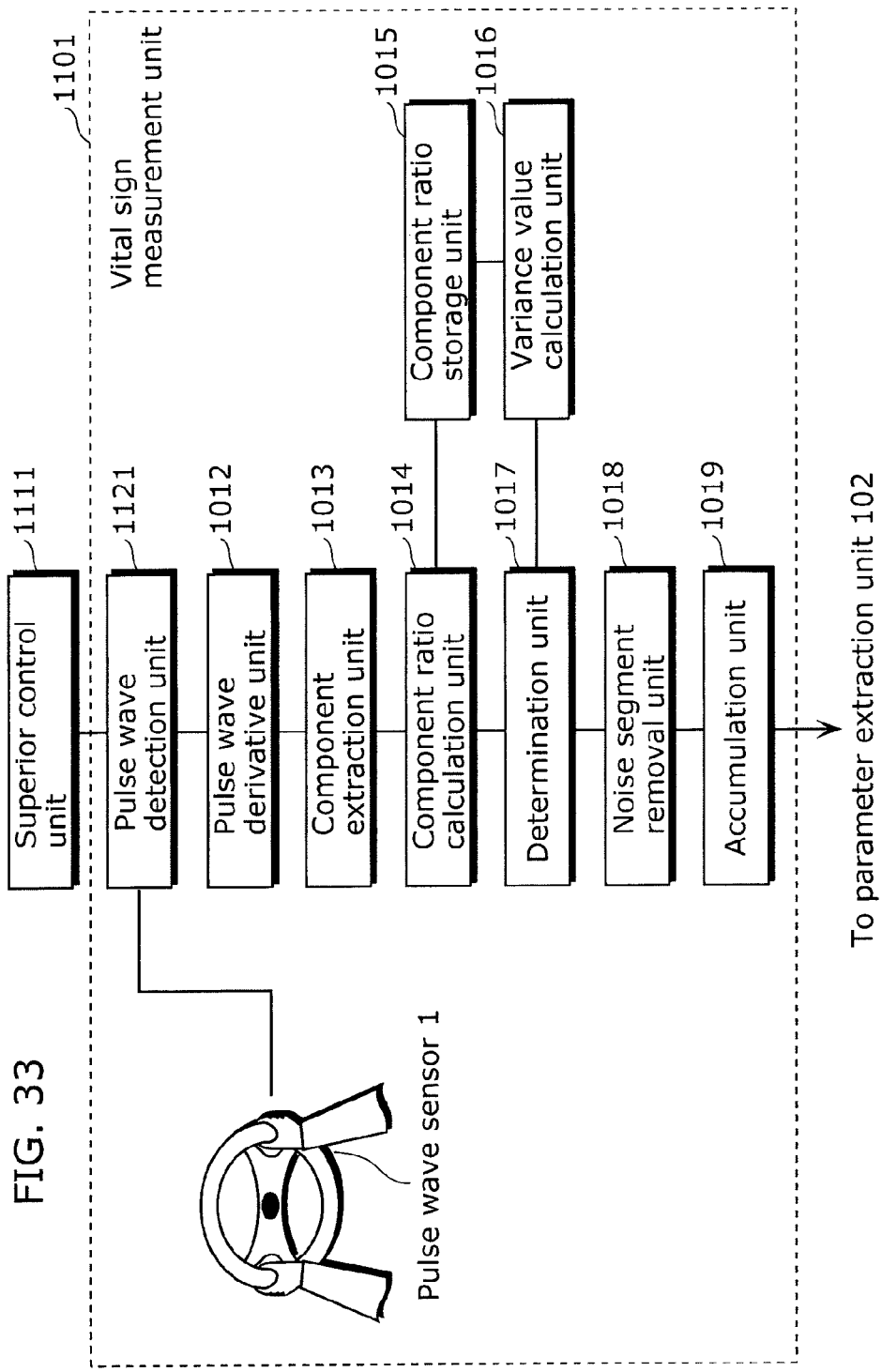
FIG. 33 is a block diagram showing the detailed structure of a vital sign measurement unit according to Embodiment 4 of the present invention.

FIG. 33 is a block diagram showing the detailed structure of the vital sign measurement unit 1101. It is assumed that the vital sign measurement unit 1101 is connected to the pulse wave sensor 1. It is assumed that the pulse wave sensor 1 is provided on the handle of the vehicle, and measures the pulse wave of the driver while the driver is grasping the handle.

The vital sign measurement unit 1101 is basically the same as the vital sign measurement unit 101 shown in FIG. 8, but is different in including a pulse wave detection unit 1121 instead of the pulse wave detection unit 1011. The pulse wave detection unit 1121 is connected to the superior control unit 1111 and the pulse wave sensor 1. The pulse wave detection unit 1121 keeps detection of output signals as a pulse wave from the pulse wave sensor 1 during a period from when the superior control unit 1111 directs the start of obtainment of the pulse data to when the superior control unit 1111 directs the end of the obtainment of the pulse data.

Next, a description is given of processing performed by the device control device according to Embodiment 4.

Figure 34:
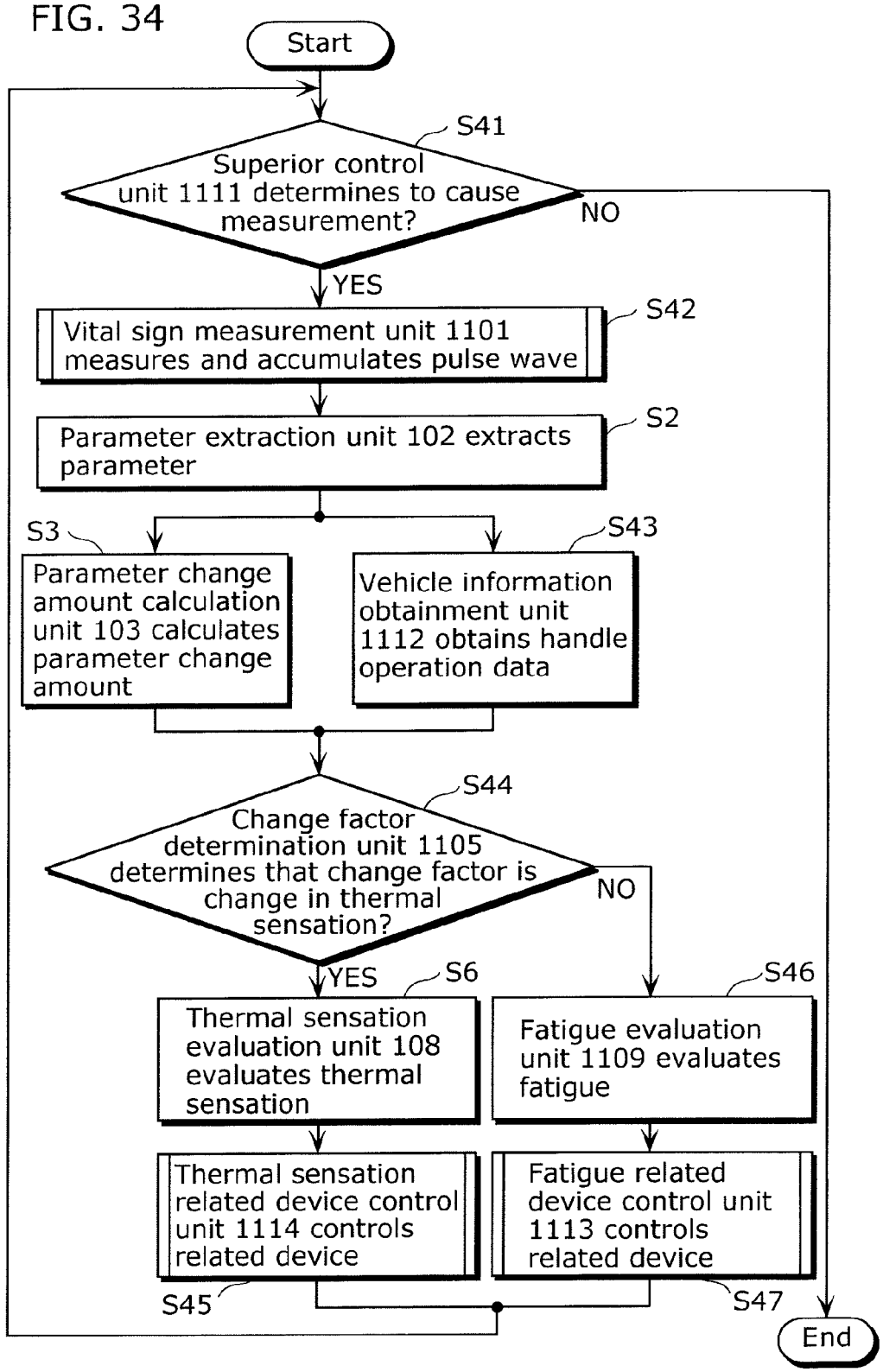
FIG. 34 is a flowchart of processing performed by the device control device according to Embodiment 4 of the present invention.

FIG. 34 is a flowchart of processing performed by the device control device according to Embodiment 4 of the present invention.

The superior control unit 1111 determines whether or not to measure the pulse wave data based on the information about the status of the vehicle obtained by the vehicle information obtainment unit 1112 (S41). For example, when the superior control unit 1111 obtains, from the vehicle information obtainment unit 1112, information indicating that the engine of the vehicle is turned on, the superior control unit 1111 determines to start measurement of the pulse wave data. In contrast, when the superior control unit 1111 obtains, from the vehicle information obtainment unit 1112, information indicating that the engine of the vehicle is turned off, the superior control unit 1111 determines to end the measurement of the pulse wave data. When the superior control unit 1111 determines to start measurement of the pulse wave data (YES in S41), the superior control unit 1111 directs the vital sign measurement unit 1101 to start obtainment of the pulse wave data. When the superior control unit 1111 determines to end the measurement of the pulse wave data (NO in S41), the superior control unit 1111 directs the vital sign measurement unit 1101 to end the obtainment of the pulse wave data. When the superior control unit 1111 directs the vital sign measurement unit 1101 to end the obtainment of the pulse wave data (NO in S41), the processing is terminated.

The superior control unit 1111 directs the vital sign measurement unit 1101 to start obtainment of the pulse wave data (YES in S41), the vital sign measurement unit 1101 that received the direction measures and accumulates pulse wave data of the driver in time series (S42). This process (S42) is the same as the measurement and accumulation process (S1) of the time-series pulse wave data described in Embodiment 1. Therefore, no detailed description is repeated here.

The parameter extraction unit 102 extracts the pulse wave amplitude, on a certain time range basis, from the time-series pulse wave data measured by the vital sign measurement unit 1101 (S2).

The parameter change amount calculation unit 103 calculates, as a change amount from the starting point, the difference between a value at the predetermined starting time point and the value at a current time point in the time-series pulse wave amplitude data extracted by the parameter extraction unit 102. In addition, the parameter change amount calculation unit 103 calculates, as a previous change amount, the difference between the value at a previous measurement time point and the value at the current time point. The parameter change amount calculation unit 103 outputs the calculated change amount from the starting point and the calculated previous change amount to the change factor determination unit 1105 (S3).

On the other hand, the vehicle information obtainment unit 1112 obtains the data of handle operation performed by the driver, and outputs the obtained handle operation data to the change factor determination unit 1105 (S43). More specifically, the vehicle information obtainment unit 1112 obtains, as the handle operation data, the ratio of time during which the handle operation acceleration (x-y two axis resultant force) exceeds a predetermined value (120 mG, for example) in a period from the predetermined starting time point to a current time point, and outputs the obtained ratio to the change factor determination unit 1105.

The change factor determination unit 1105 determines the factor of the change in the pulse wave amplitude based on the change amount from the starting point outputted by the parameter change amount calculation unit 103 and the handle operation data outputted by the vehicle information obtainment unit 1112 (S44). When the change factor determination unit 1105 determines that the factor of the change is a change in the thermal sensation (YES in S44), it outputs, to the thermal sensation evaluation unit 108, the current change amount from the starting point that is information to be used for evaluating the thermal sensation. When the change factor determination unit 1105 determines that the factor of the change is a change in the fatigue level (NO in S44), it outputs, to the fatigue evaluation unit 1109, the current change amount from the starting point that is information to be used for evaluating the fatigue level. This determination process (S44) is described later in detail.

The thermal sensation evaluation unit 108 evaluates the user's thermal sensation based on the change amount from the starting point outputted by the change factor determination unit 1105, and outputs the evaluation result to the thermal sensation related device control unit 1114 (S6). The method for evaluating thermal sensation is the same as in Embodiment 1, and thus no detailed description is repeated here.

The thermal sensation related device control unit 1114 performs device control for making better the thermal sensation based on the thermal sensation evaluation result outputted by the thermal sensation evaluation unit 108 (S45).

The fatigue evaluation unit 1109 evaluates the user's fatigue level based on the change amount from the starting point outputted by the change factor determination unit 1105, and outputs the evaluation result to the fatigue related device control unit 1113 (S46). The method for evaluating a fatigue level is the same as in Embodiment 1, and thus no detailed description is repeated here.

Based on the evaluation result of the fatigue level outputted by the fatigue evaluation unit 1109 (S47), the fatigue related device control unit 1113 performs device control for reducing the fatigue level.

Figure 35:
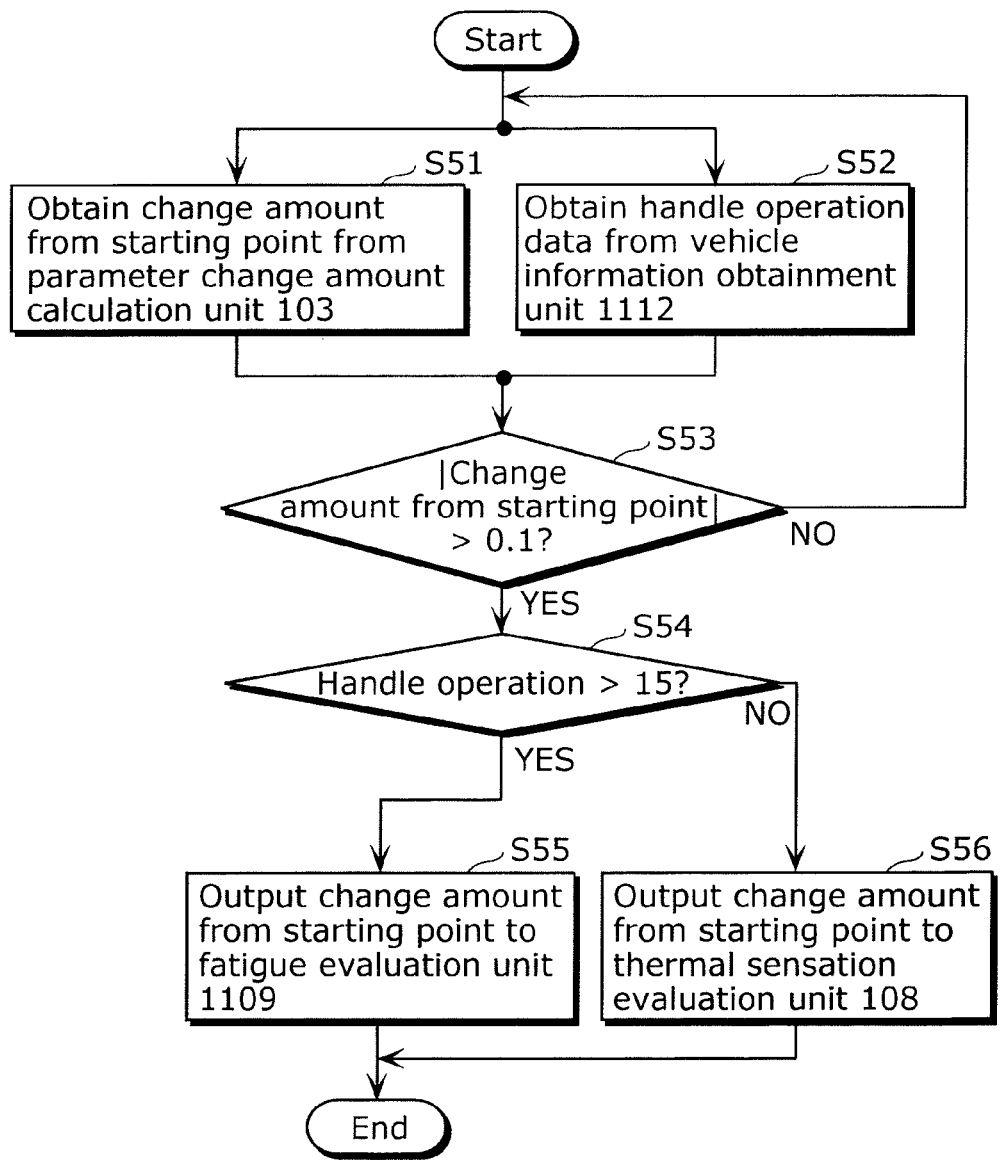
FIG. 35 is a flowchart of processing performed by the change factor determination unit according to Embodiment 4 of the present invention.

Next, a detailed description is given of the processing (S44 in FIG. 34) for determining the factor of the change in the pulse wave amplitude performed by the change factor determination unit 1105. FIG. 35 is a flowchart of the processing performed by the change factor determination unit 1105 according to Embodiment 4 of the present invention. In addition, FIG. 36 is a diagram showing a data table used for determining the factor of the change in the amplitude of the pulse wave stored in the change factor determination unit 1105. The processing shown in FIG. 35 is described below based on the contents of the data table shown in FIG. 36.

The change factor determination unit 1105 obtains the change amount from the starting point from the parameter change amount calculation unit 103 (S51). In addition, the change factor determination unit 1105 obtains the handle operation data from the vehicle information obtainment unit 1112 (S52). The change factor determination unit 1105 determines whether or not the absolute value of the change amount from the starting point is greater than a predetermined numerical value (0.1) (S53). When the absolute value of the change amount from the starting point is not greater than 0.1 (NO in S53), the change factor determination unit 1105 waits until the next change amount from the starting point and the next handle operation data are obtained, and repeats the process S51 and the following processes from S52.

When the absolute value of the change amount from the starting point is greater than 0.1 (YES in S53), the change factor determination unit 1105 determines whether or not the handle operation data is greater than a predetermined numerical value (15%) (S54). When the absolute value of the handle operation data is greater than 15% (YES in S54), the change factor determination unit 1105 determines that the factor of the change in the pulse wave amplitude is a change in the driver's fatigue level as shown in FIG. 36, and outputs, to the fatigue evaluation unit 1109, the current change amount from the starting point that is information to be used for evaluating the fatigue level (S55). When the absolute value of the handle operation data is not greater than 15% (NO in S54), the change factor determination unit 1105 determines that the factor of the change in the pulse wave amplitude is a change in the driver's thermal sensation as shown in FIG. 36, and outputs, to the thermal sensation evaluation unit 108, the current change amount from the starting point that is information to be used for evaluating the thermal sensation (S56).

It can be said that driving with handle operations corresponding to handle operation data of 15% or more is burdensome for the driver, and imposes a considerable load on the driver. This makes the driver tired. Thus, setting "15% or more" as the threshold value for the handle operation data enables the most appropriate discrimination between the thermal sensation and the fatigue level. Therefore, in this embodiment, the threshold value for the handle operation data is determined to be 15%.

Figure 38:
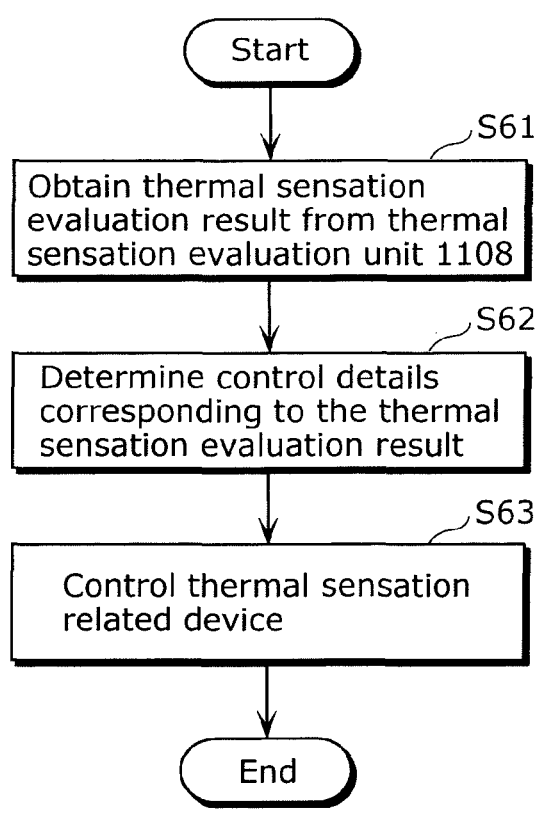
FIG. 38 is a flowchart of processing performed by a thermal sensation related device control unit according to Embodiment 4 of the present invention.

Next, a detailed description is given of the device control processing (S45 in FIG. 34) performed by the thermal sensation related device control unit 1114. FIG. 38 is a flowchart of processing executed by the thermal sensation related device control unit 1114.

The thermal sensation related device control unit 1114 obtains the evaluation result of the thermal sensation from the thermal sensation evaluation unit 108 (S61). The thermal sensation related device control unit 1114 determines the control details corresponding to the obtained thermal sensation evaluation result (S62). For example, the control details determined in the case where it is evaluated that the thermal sensation is shifted to "hot" include to lower the temperature of a warm or cool heat output device such as an air conditioner, to lower the temperature of a device for outputting air flow such as cool wind or warm wind, and to increase the air flow. In addition, the control details determined in the case where it is evaluated that the thermal sensation is shifted to "cold" include to raise the temperature of the warm or cool heat output device such as the air conditioner, to raise the temperature of the device for outputting air flow such as cool wind or warm wind, and to decrease the air flow. The thermal sensation related device control unit 1114 performs device control according to the determined control details (S63).

Figure 39:
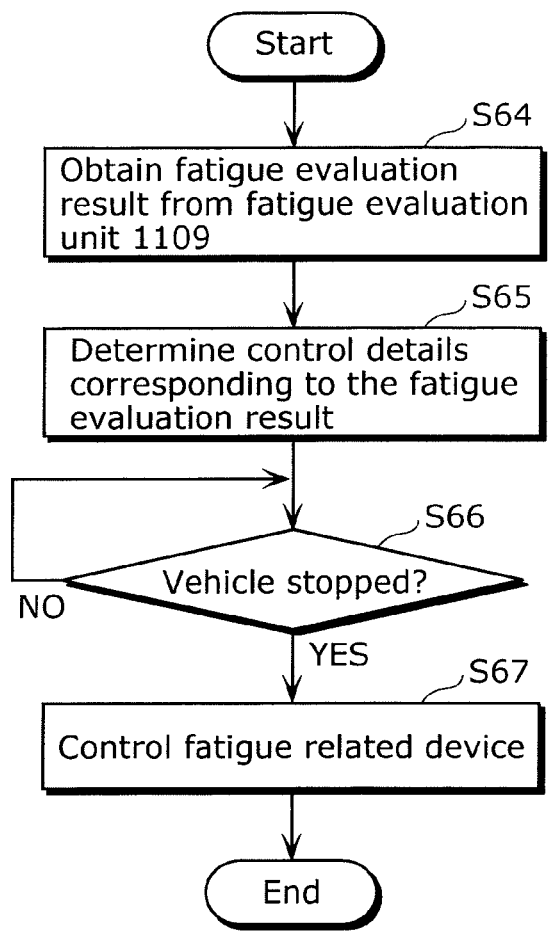
FIG. 39 is a flowchart of processing performed by a fatigue related device control unit according to Embodiment 4 of the present invention.

Next, a description is given of device control process (S47 in FIG. 34) performed by the fatigue related device control unit 1113. FIG. 39 is a flowchart of the processing executed by the fatigue related device control unit 1113.

The fatigue related device control unit 1113 obtains the evaluation result of the fatigue level from the fatigue evaluation unit 1109 (S64). The fatigue related device control unit 1113 determines the control details corresponding to the obtained fatigue level evaluation result (S65). For example, the control details in the case where it is evaluated that the fatigue level is on the increase include causing a massage device to operate, causing a device for outputting oxygen or negative ions to operate, causing a navigation system to lead the vehicle to nearby woods. When the vehicle information obtainment unit 1112 obtains information indicating that the vehicle is stopped (YES in S66), the fatigue related device control unit 1113 performs device control according to the determined control details (S67). Performing device control when the vehicle is stopped and not performing device control while the vehicle is running makes it possible, for example, to prevent the massage device from operating during the driving and triggering a handle operation error and prevent a navigation system from misleading the vehicle to a place different from a destination. This allows the driver to continue safety driving to the destination.

As described above, with the device control device according to Embodiment 4, when a user's pulse wave changes, it is possible to determine the factor of the change in the pulse wave taking into account the handle operation data in addition to the change amount in the pulse wave. In other words, it is possible to discriminate the factor of the change in the pulse wave, that is, determine whether the change is due to a change in the thermal sensation or a change in the fatigue level. In addition, it is also possible to evaluate the user's thermal sensation or fatigue level based on the change factor. This prevents device control based on an erroneous evaluation result in the system for obtaining the user's pulse wave and feeding back information about the pulse wave, and makes it possible to reliably present the user status and perform device control to make the user status better. In a particular situation where the user drives the vehicle, the most appropriate device control can be performed. This allows the user to drive the vehicle more comfortably and safely.

Embodiment 5

The following description is given of an device control device according to Embodiment 5 of the present invention. The same elements as those of the device control device according to Embodiments 1 to 4 are assigned with the same numerical references. The functions and names are also the same, and thus no detailed descriptions are repeated here.

The device control device according to Embodiment 5 is intended to control an on-vehicle device.

Figure 40:
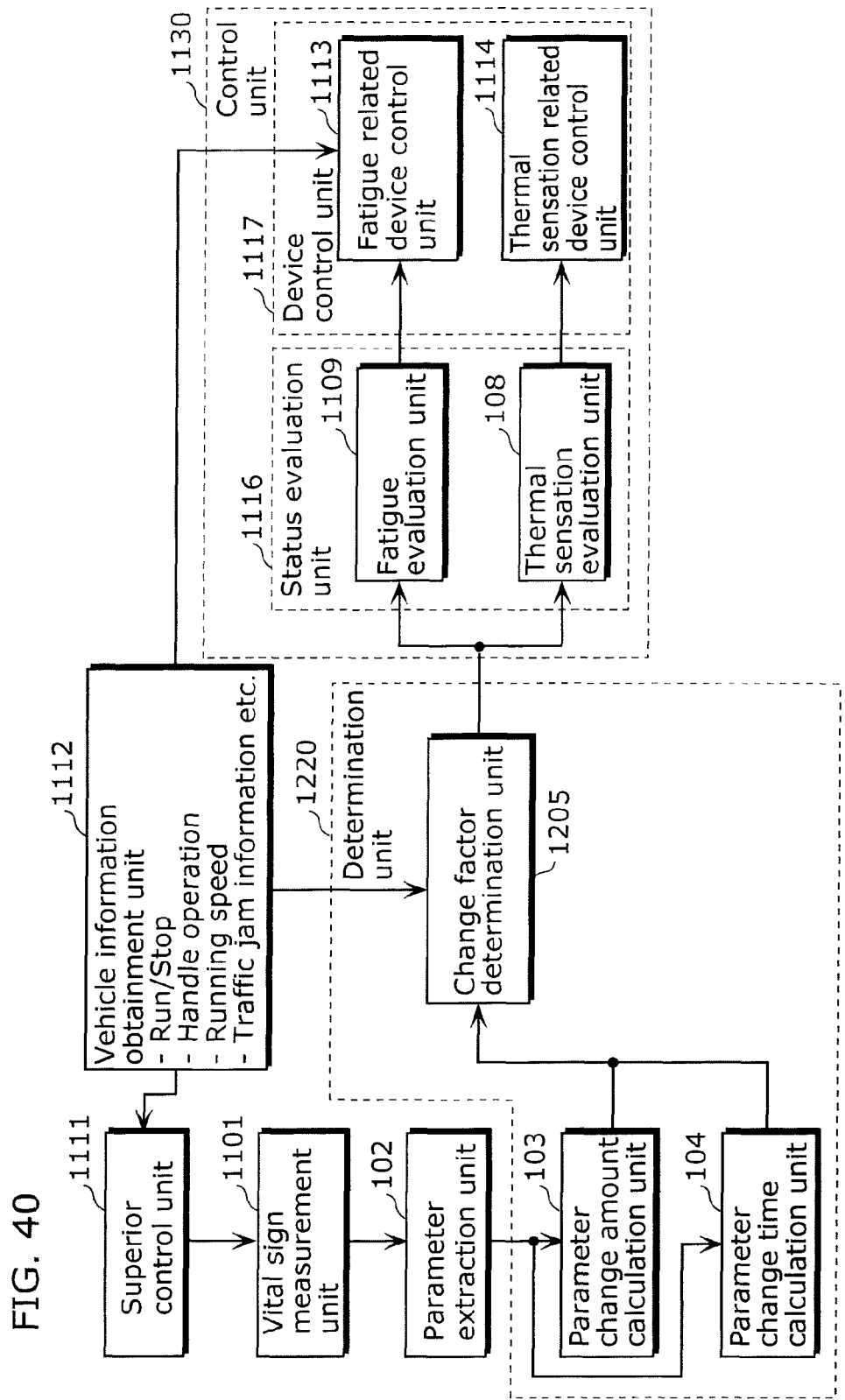
FIG. 40 is a block diagram showing the structure of a device control device according to Embodiment 5 of the present invention.

FIG. 40 is a block diagram showing the structure of the device control device according to Embodiment 5 of the present invention. The device control device shown in FIG. 40 is configured with known computers for example, and includes a superior control unit 1111, a vehicle information obtainment unit 1112, a vital sign measurement unit 1101, a parameter extraction unit 102, a determination unit 1220, and a control unit 1130. These processing units function when the program is executed by a CPU of a computer storing an installed device control program designed according to this embodiment. The device control device according to Embodiment 5 includes a determination unit 1220 instead of the determination unit 1120 in the same structure as in the device control device according to Embodiment 4 shown in FIG. 32. As for the other elements, the device control device according to Embodiment 5 is the same as the device shown in FIG. 32.

The determination unit 1220 includes the parameter change amount calculation unit 103, the parameter change time calculation unit 104, and a change factor determination unit 1205. The change factor determination unit 1205 determines the factor of the change in the pulse wave amplitude (the factor is, for example, the influence of a thermal sensation or the influence of a health condition), based on (i) the change amount from the starting point and the previous change amount calculated by the parameter change amount calculation unit 103 and (ii) the change time from the starting point calculated by the parameter change time calculation unit 104, and (iii) the information about the status of the vehicle obtained by the vehicle information obtainment unit 1112. Based on the determined factor, the change factor determination unit 1205 selects the best evaluation unit from among a thermal sensation evaluation unit 108 and a fatigue evaluation unit 1109 included in the status evaluation unit 1116, and outputs, to the selected evaluation unit, the current change amount from the starting point that is information to be used for evaluating the current user status.

Next, a description is given of processing performed by the device control device according to Embodiment 5.

Figure 41:
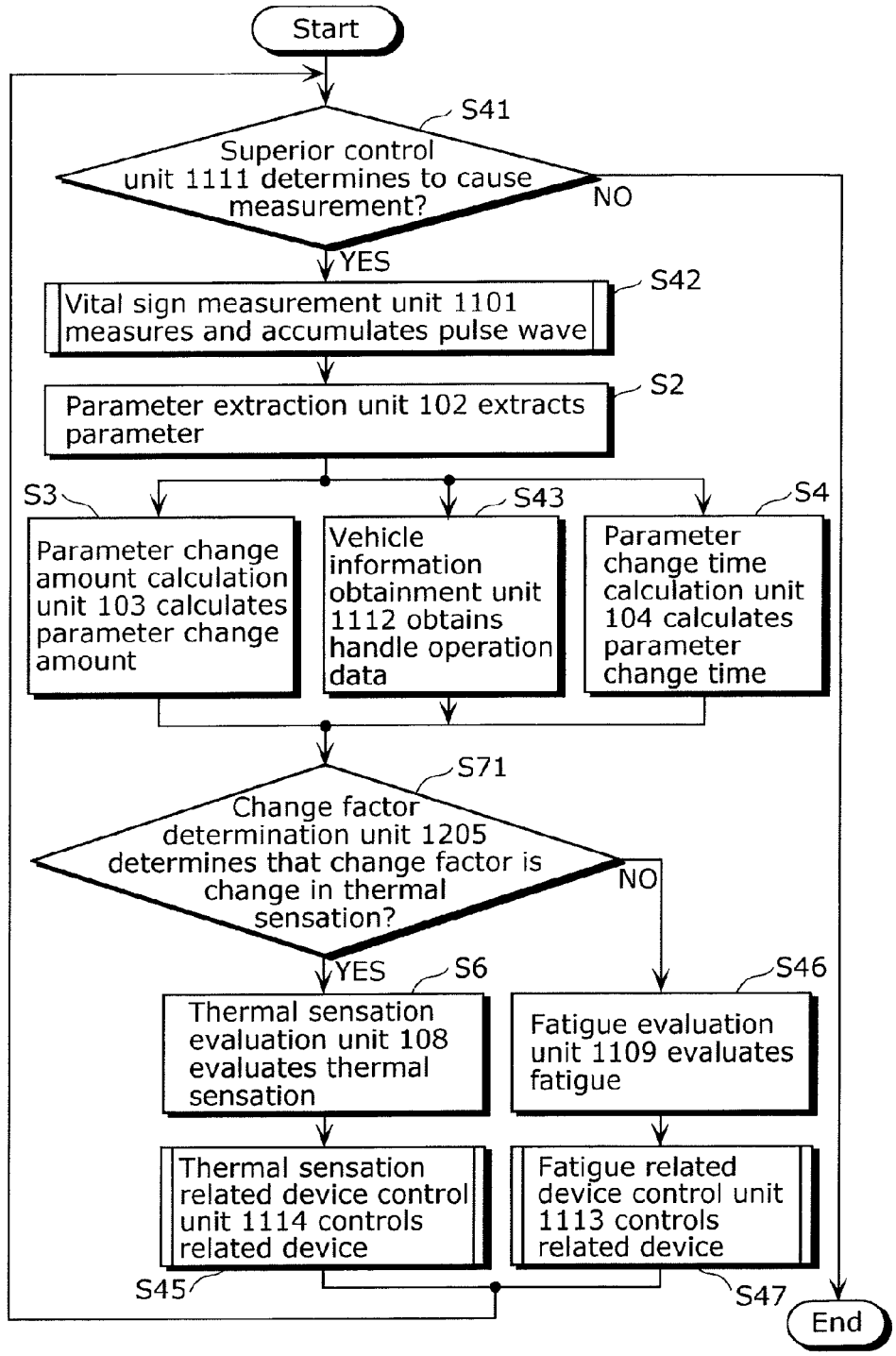
FIG. 41 is a flowchart of processing performed by the device control device according to Embodiment 5 of the present invention.

FIG. 41 is a flowchart of processing performed by the device control device according to Embodiment 5 of the present invention.

The device control device executes the same processes S41, S42, S2, S3, and S43 as in Embodiment 4. Meanwhile, the parameter change time calculation unit 104 calculates, as the change time from the starting point, an elapsed time from the predetermined starting time point to the current time point in the time-series pulse wave amplitude data extracted by the parameter extraction unit 102, and outputs the current change time from the starting point to the change factor determination unit 1205 (S4).

The change factor determination unit 1205 determines the factor of the change in the pulse wave amplitude, based on (i) the change amount from the starting point and the previous change amount outputted by the parameter change amount calculation unit 103, (ii) the change time from the starting point outputted by the parameter change time calculation unit 104, and (iii) the handle operation data outputted by the vehicle information obtainment unit 1112 (S71). When the change factor determination unit 1205 determines that the factor of the change is a change in the thermal sensation (YES in S71), it outputs, to the thermal sensation evaluation unit 108, the current change amount from the starting point that is information to be used for evaluating the thermal sensation. When the change factor determination unit 1205 determines that the factor of the change is a change in the fatigue level (NO in S71), it outputs, to the fatigue evaluation unit 1109, the current change amount from the starting point that is information to be used for evaluating the fatigue. This determination process (S71) is described later in detail.

Subsequently, the device control device executes the same processes of S6 and S45 to S47 as in Embodiment 4.

Figure 42:
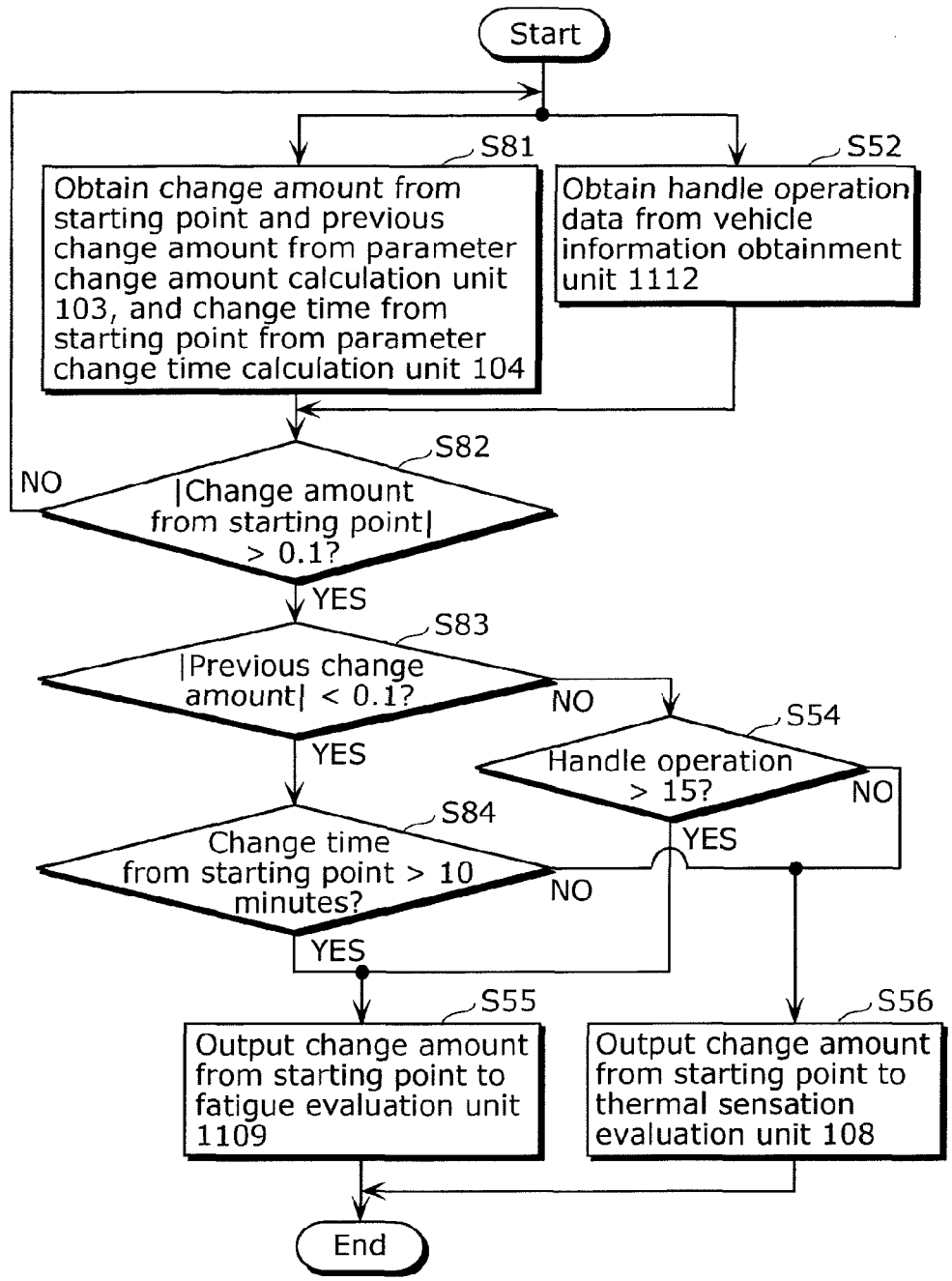
FIG. 42 is a flowchart of processing performed by the change factor determination unit according to Embodiment 5 of the present invention.

Next, a detailed description is given of the processing (S71 in FIG. 41) that the change factor determination unit 1205 performs to determine the factor of the change in the pulse wave amplitude. FIG. 42 is a flowchart of the processing performed by the change factor determination unit 1205 according to Embodiment 5 of the present invention. The change factor determination unit 1205 determines the factor of the change in the pulse wave amplitude using the data table shown in FIG. 13 and the data table shown in FIG. 36. The processing shown in FIG. 42 is described below based on the contents of the data table shown in FIG. 13 and FIG. 36. This processing is a combination of the processing executed by the change factor determination unit 105 according to Embodiment 1 shown in FIG. 12 and the processing executed by the change factor determination unit 1105 according to Embodiment 4 shown in FIG. 35.

First, the change factor determination unit 1205 obtains the change amount from the starting point and the previous change amount from the parameter change amount calculation unit 103, and obtains the change time from the starting point from the parameter change time calculation unit 104 (S81). In addition, the change factor determination unit 1205 obtains the handle operation data from the vehicle information obtainment unit 1112 (S52).

The change factor determination unit 1205 determines whether or not the absolute value of the change amount from the starting point is greater than a predetermined numerical value (0.1) (S82). When the absolute value of the change amount from the starting point is not greater than 0.1 (NO in S82), the change factor determination unit 105 waits until the next change amount from the starting point and the previous change amount are obtained, and repeats the process S81 and the processes from S52.

When the absolute value of the change amount from the starting point is greater than 0.1 (YES in S82), the change factor determination unit 1205 determines whether or not the absolute value of the previous change amount is smaller than the predetermined numerical value (0.1) (S83).

When the absolute value of the previous change amount is smaller than 0.1 (YES in S83), the change factor determination unit 1205 determines whether or not the change time from the starting point is greater than a predetermined value (10 minutes) (S84). When the change time from the starting point is greater than 10 minutes (YES in S84), the change factor determination unit 1205 determines that the factor of the change in the pulse wave amplitude is a fatigue level (a health condition) as shown in FIG. 13, and outputs, to the fatigue evaluation unit 1109, the current change amount from the starting point that is information to be used for evaluating the fatigue level (S55). When the change time from the starting point is not greater than 10 minutes (NO in S84), the change factor determination unit 1205 determines that the factor of the change in the pulse wave amplitude is a change in the thermal sensation, and outputs, to the thermal sensation evaluation unit 108, the current change amount from the starting point that is information to be used for evaluating the thermal sensation (S56).

When the absolute value of the previous change amount is greater than 0.1 (NO in S83), the change factor determination unit 1205 determines whether or not the handle operation data is greater than the predetermined numerical value (15%) (S54). When the absolute value of the handle operation data is greater than 15% (YES in S54), the change factor determination unit 1205 determines that the factor of the change in the pulse wave amplitude is a change in the driver's fatigue level as shown in FIG. 36, and outputs, to the fatigue evaluation unit 1109, the current change amount from the starting point that is information to be used for evaluating the fatigue level (S55). When the absolute value of the handle operation data is not greater than 15% (NO in S54), the change factor determination unit 1205 determines that the factor of the change in the pulse wave amplitude is a change in the driver's thermal sensation as shown in FIG. 36, and outputs, to the thermal sensation evaluation unit 108, the current change amount from the starting point that is information to be used for evaluating the thermal sensation (S56).

As described above, with the device control device according to Embodiment 5, when a user's pulse wave changes, it is possible to determine the factor of the change in the pulse wave taking into account the time required for the change in addition to the change amount in the pulse wave. Further, with the device control device according to Embodiment 5, when a user's pulse wave changes, it is possible to determine the factor of the change in the pulse wave taking into account the handle operation data in addition to the change amount in the pulse wave. In other words, it is possible to discriminate the factor of the change in the pulse wave, that is, determine whether the change is due to a change in the thermal sensation or a change in the fatigue level. In addition, it is also possible to evaluate the user's thermal sensation or fatigue level based on the change factor. This prevents device control based on an erroneous evaluation result in the system for obtaining the user's pulse wave and feeding back information about the pulse wave, and makes it possible to reliably present the user status and perform device control to make the user status better. In a particular situation where the user drives the vehicle, the most appropriate device control can be performed. This allows the user to drive the vehicle more comfortably and safely.

(Variation)

The vital sign measurement unit 101 according to the above-described Embodiments determines whether or not the pulse wave data includes noise based on the variance values of the component ratios. However, it is also good to determine whether or not the pulse wave data includes noise based on whether or not the component ratios fall within a predetermined range. For example, as shown in FIG. 9, the ratio (component ratio) of the maximum value and the minimum value of the velocity plethysmogram changes significantly in Segments A and B affected by body movements, but changes slightly in Segment C affected by change in the thermal sensation. Accordingly, the component ratio in Segment C falls within the predetermined range.

Figure 43:
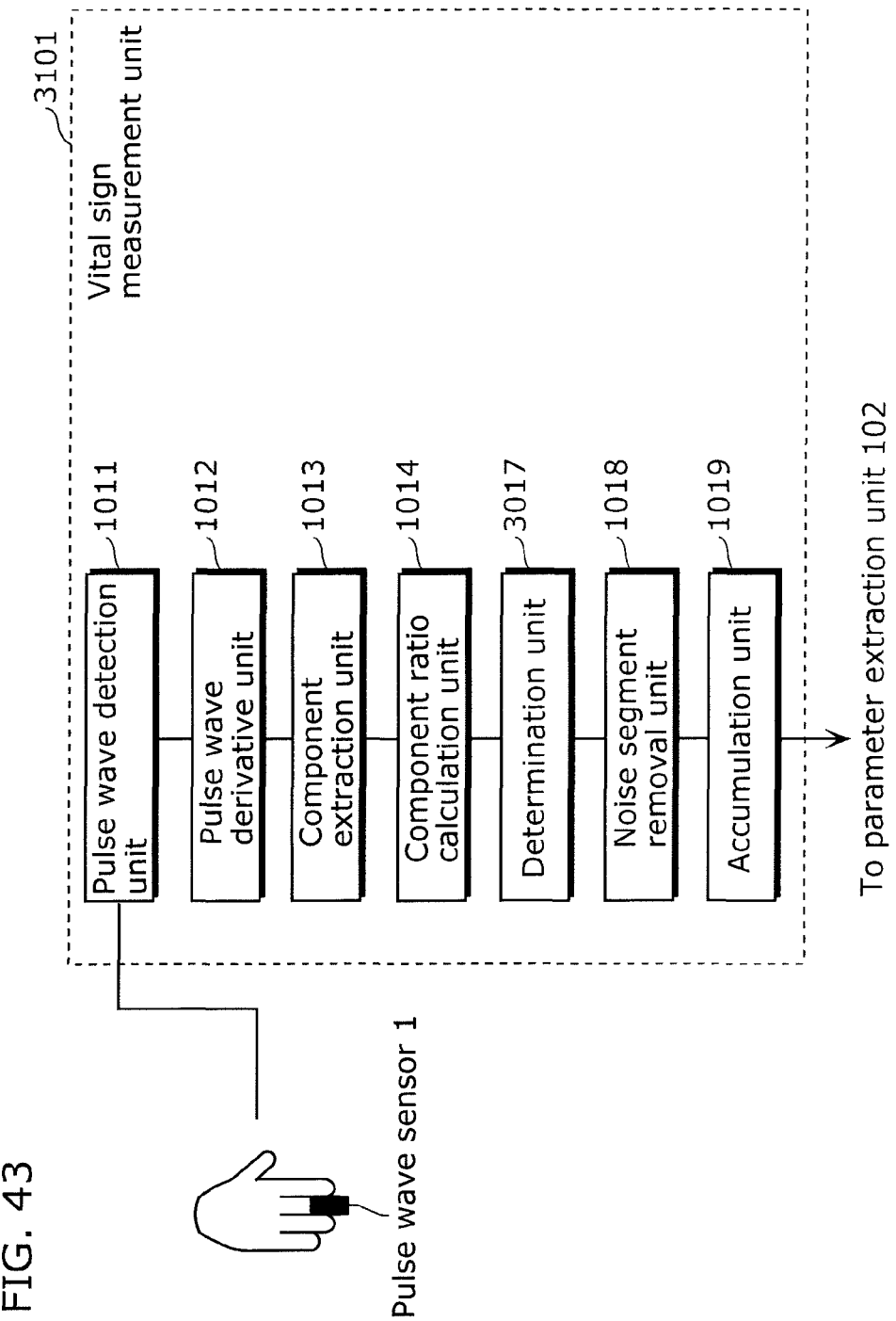
FIG. 43 is a block diagram showing the structure of a vital sign measurement unit.

FIG. 43 is a block diagram showing another structure of the vital signal measurement unit. It is assumed that the vital sign measurement unit 3101 is connected to the pulse wave sensor 1.

The vital sign measurement unit 3101 includes a pulse wave detection unit 1011, a pulse wave derivative unit 1012, a component extraction unit 1013, a component ratio calculation unit 1014, a determination unit 3017, a noise segment removal unit 1018, and an accumulation unit 1019. Unlike the vital sign measurement unit 101 shown in FIG. 8, the vital sign measurement unit 3101 does not include the component ratio storage unit 1015 and the variance value calculation unit 1016, and includes a determination unit 1017 instead of the determination unit 3017. For this reason, the same processing units as in the vital sign measurement unit 101 are not repeatedly described in detail here. The determination unit 1017 determines whether or not the pulse wave includes noise based on the component ratio value calculated by the component ratio calculation unit 1014.

Figure 44:
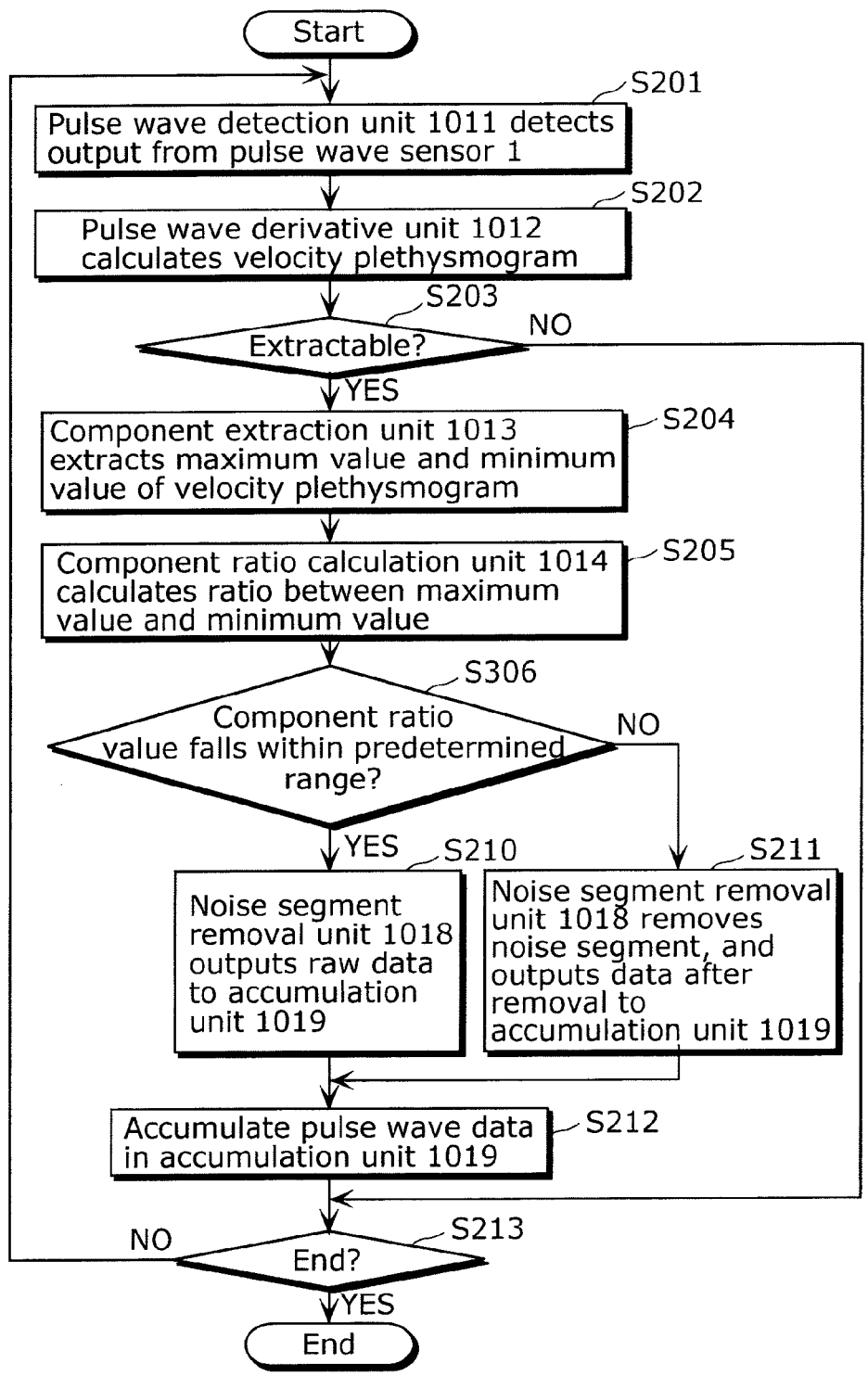
FIG. 44 is a flowchart of processing performed by the vital sign measurement unit according to Embodiment 5 of the present invention.

FIG. 44 is a flowchart of processing performed by the vital sign measurement unit 3101. The same processing as indicated in the flowchart of the processing executed by the vital sign measurement unit 101 shown in FIG. 17 are assigned with the same step numbers, and no detailed descriptions are repeated here.

The vital sign measurement unit 3101 calculates the component ratios by executing the processes S201 to S205.

The determination unit 3017 determines whether or not the calculated component ratios fall within the predetermined component ratio (for example, a range from −0.1 to −0.4) (S306). Here, in the case where the variance values fall within the range predetermined for variance values (YES in S306), the determination unit 3017 determines that the detected pulse wave does not include noise, and the noise segment removal unit 1018 outputs the data indicating the pulse wave to the accumulation unit 1019 without performing noise removal (S210).

In contrast, in the case where the variance values do no fall within the range predetermined for variance values (NO in S306), the determination unit 3017 determines that the detected pulse wave includes noise, and the noise segment removal unit 1018 removes the pulse wave portion corresponding to the noise segment and outputs the data indicating the pulse wave which has been subjected to the noise removal to the accumulation unit 1019 (S211).

The accumulation unit 1019 accumulates the pulse wave data outputted by the noise segment removal unit 1018 (S212).

The vital sign measurement unit 101 checks whether or not a condition for terminating the current processing is satisfied (S213). In the case where the termination condition is satisfied (YES in S213), the vital sign measurement unit 101 terminates the processing. In the case where the termination condition is not satisfied (NO in S213), the pulse wave detection unit 1011 continues the pulse wave detection process (S201).

As described above, this variance makes it possible to discriminate a change in the pulse wave made by a change in the thermal sensation from noise caused due to the influence of body movements, by calculating the component ratios that are the ratios of the maximum values and the minimum values in predetermined time ranges of the velocity plethysmogram, and determining whether or not the component ratios fall within the predetermined component ratio range.

The above-described Embodiments and the Variation thereof according to the present invention are not intended to limit the present invention.

For example, in the case of the data table used by the change factor determination unit 105 shown in FIG. 13 in Embodiments 1 and 5, the threshold value for the change amount from the starting point and the previous change amount is 0.1, and the threshold value for the change time from the change point is 10 minutes. However, threshold values are not limited to those, and other predetermined numerical values may be used. In addition, as for the threshold value for the change amount from the starting point and the previous change amount, it is also good to use, instead of the predetermined numerical value, a numerical value (such as the value corresponding to 10% of the following average value) calculated based on the average value in a certain segment in the time-series data of the user's pulse wave amplitude.

In Embodiment 2, in the case of the data table used by the change factor determination unit 506 shown in FIG. 26, the threshold value for the change amount from the starting point is 0.1 and the threshold value for the temperature change amount from the starting point is 3 degrees Celsius. However, threshold values are not limited to these and other predetermined numerical values may be used. In addition, as for the threshold value for the change amount from the starting point, it is also good to use, instead of the predetermined numerical value, a numerical value (such as the value corresponding to 10% of the following average value) calculated based on the average value in a certain segment in the time-series data of the user's pulse wave amplitude.

In Embodiment 3, in the case of the data table used by the change factor determination unit 905 shown in FIG. 31, the threshold value for the change amount from the starting point is 0.1 and the threshold value for the integration value of the change amounts each from the previous point is 1. However, threshold values are not limited to these, and other predetermined numerical values may be used. In addition, as for the threshold value for the change amount from the starting point, it is also good to use, instead of the predetermined numerical value, a numerical value (such as the value corresponding to 10% of the following average value) calculated based on the average value in a certain segment in the time-series data of the user's pulse wave amplitude.

In Embodiments 4 and 5, in the case of the data table used by the change factor determination unit 1105 shown in FIG. 36, the threshold value for the change amount from the starting point is 0.1 and the threshold value for the handle operation data is 15%. However, threshold values are not limited to these, and other predetermined numerical values may be used. In addition, as for the threshold value for the change amount from the starting point, it is also good to use, instead of the predetermined numerical value, a numerical value (such as the value corresponding to 10% of the following average value) calculated based on the average value in a certain segment in the time-series data of the user's pulse wave amplitude.

The parameter extraction unit 102 extracts the pulse wave amplitude as parameter values in the above-described Embodiments. However, the parameter extraction unit 102 may extract, as parameter values, vital signs which are possibly used for evaluating a user's thermal sensation and health condition. Examples of such vital sighs include: (i) the number of heartbeats and the number of pulses; (ii) waveform components (a, b, c, d, and e) of an accelerated plethysmogram obtained by performing second-order derivative on the pulse waveform and the waveform component ratios (b/a, c/a, d/a, and e/a); (iii) the ratio obtained using LF/HF and HF that are results of frequency analysis on the pulse wave intervals; and (iv) the Maximum Lyapunov exponents that are the result of chaotic analysis on the pulse waveform. Here, a, b, c, d, and e respectively denotes the amplitude values of Wave a, Wave b, Wave c, Wave d, and Wave e shown in FIG. 22.

In addition, the device control that is performed by either the device control unit 107 or the thermal sensation related device control unit 1114 may display the user's thermal sensation on a display device or output an alert according to the user's thermal sensation status. In addition, the device control that is performed by either the device control unit 107 or the fatigue related device control unit 1113 may display the user's health condition or fatigue level on the display device or output an alert according to the user's health condition or fatigue level status. In addition, the device control for making better the user's thermal sensation or the user's health condition may be the one that provides: thermal stimulation using warm or cool wind etc.; air flow stimulation using cool or warm wind etc.; physical stimulation using massage etc.; or physical stimulation using oxygen or negative ions etc. For example, the control details determined in the case where it is evaluated that the thermal sensation is shifted to "hot" may include to lower the temperature in the thermal stimulation, and to increase air flow in the air flow stimulation. On the other hand, the control details determined in the case where it is evaluated that the thermal sensation is shifted to "cold" may include to raise the temperature in the thermal stimulation, and to decrease air flow in the air flow stimulation. In the case where it is evaluated that the thermal sensation is shifted to "discomfort", the current control details may be canceled. In the opposite case where it is evaluated that the thermal sensation is shifted to "comfort", the current control details may be continued. In addition, in the case where it is evaluated that the health condition is shifted to "bad" with an increase in fatigue level, it is also good to provide the user with physical stimulation by a massage or by negative ions or the like.

In addition, in the extraction of a pulse wave amplitude, the parameter extraction unit 102 extracts the pulse wave amplitude for each element wave of the pulse wave and outputs the pulse wave amplitude after each extraction. However, the parameter extraction unit 102 may output the average value of the pulse wave amplitudes of the plural element waves of the pulse wave.

In addition, specific time points are predetermined for the starting time point in the time-series data of the pulse wave amplitude used by the parameter change amount calculation unit 103, the parameter change time calculation unit 104, and the parameter change amount integration unit 904 and the unit 505 for calculating a temperature change amount from a starting point. However, it is also good to update the starting time point to a current time point for each predetermined time range (such as 1 minute), or to determine, as the starting time point, the time point preceding the current time point by the predetermined time range (such as 10 minutes).

In addition, in Embodiments 1 to 3, the status evaluation unit 106 includes the thermal sensation evaluation unit 108 and the health condition evaluation unit 109. However, it is also good that the health condition evaluation unit 109 classifies the evaluated health conditions in further detail, and includes a fatigue level evaluation unit, a stress evaluation unit, a sleepiness evaluation unit and the like.

In addition, the vital sign measurement units 101 and 1101 in the above-described Embodiments may use standard deviation values instead of the variance values of component ratios.

The vital sign measurement units 101 and 1101 in the above-described Embodiments determine whether or not the pulse wave includes noise based on the variance values. However, it is also good to provide each of the vital sign measurement unit with a storage device for storing the variance values and a processing unit for calculating the difference value of current two variance values, and determine mixture of noise depending on whether or not the difference value falls within a predetermined range.

In addition, the vital sign measurement unit 3101 in the above-described Variation determines whether or not the pulse wave includes noise based on the component ratio values. However, it is also good to provide each of the vital sign measurement unit with a storage device for storing the component ratio values and a processing unit for calculating the difference value of current two component ratio values, and determine mixture of noise depending on whether or not the difference value falls within a predetermined range.

In addition, the pulse wave sensor 1 is assumed to be a transparent optical sensor in the above-described Embodiments, but the pulse wave sensor 1 may be a reflection sensor or a piezoelectric sensor. In addition, it is also good that a pulse may be measured at the root of a finger or a palm.

In addition, the range (T2 in FIG. 18) in which a minimum value is extracted by the component extraction unit 1013 is temporally backward of the point (U(n) in FIG. 18) at which a maximum values is extracted, but it is also good to extract the minimum value from the whole range (T1 in FIG. 18).

In addition, each of the component ratios that is calculated by the component ratio calculation unit 1014 is the value obtained by dividing the minimum value by the maximum value, but it is also good that each of the component ratios that is calculated by the component ratio calculation unit 1014 is the value obtained by dividing the maximum value by the minimum value.

Here, it is also good to make a notification that a pulse wave includes noise. In addition, when the pulse wave does not include noise, it is also good to make a notification that the pulse wave has already been detected using sound, light or the like, or to display the pulse waveform.

In addition, the pulse wave sensor 1 is provided on the handle of a vehicle in Embodiments 4 and 5, and measures a pulse wave of the driver while the driver is grasping the handle. This is not intended to limit the present invention. For example, it is also good to provide the pulse wave sensor 1 on a shift lever or an arm rest that is possibly touched by the driver or a rider, and causes the pulse wave sensor 1 to measure the pulse wave of the driver or the rider when touched.

In addition, in the above-described Embodiments, a predetermined device is controlled according to the evaluation result by either the health condition evaluation unit 109 or the fatigue evaluation unit 1109. However, an implementation of simply recording health conditions and fatigue levels on a recorder is possible, and an implementation of transmitting health conditions and fatigue levels to a server via a network is also possible. It is also good to transmit these to the server only when the current fatigue level is greater than a predetermined threshold value.

In addition, the above Embodiments describe device control focusing on the applications to vehicles, but the device control may be used for other applications. For example, in the environments where current temperatures change, it is also good to measure the fatigue levels of a user who operates a personal computer in an office with an air conditioner, the fatigue levels of a user who operates a register device in a shop with a cooking space, and perform device control according to the measurement results.

Each of the devices shown in the above-described Embodiments is configured with computers, but all or part of the structural elements that constitute the devices may be configured with integrated circuits represented by system LSIs (Large Scale Integration). A system LSI is a single-chip super-multi-functional LSI configured to include plural structural means integrated thereon. More specifically, the super-multi-functional LSI is a computer system configured to include a microprocessor, a ROM, a RAM, and the like. The RAM stores a computer program. When the microprocessor operates according to the computer program, the system LSI implements the functions.

The Embodiments disclosed above are exemplary in all respects, and thus are not intended to limit the present invention. The scope of the present invention is defined by the CLAIMS not by the DESCRIPTION, and all possible modifications having equivalents to those in the CLAIMS and within the scope of the CLAIMS are intended to be included in the present invention.

INDUSTRIAL APPLICABILITY

The device control device according to the present invention can reliably evaluate a user status by discriminating the factor of a change in a vital sign that is a material for evaluating the user status when evaluating the user status based on the vital sign, and performs device control. Therefore, the device control device is useful as a device control device that controls an on-vehicle device based on the vital sign.

The device control device according to the present invention can reliably evaluate a user status by discriminating the factor of a change in a vital sign that is a material for evaluating the user status when evaluating the user status based on the vital sign, and performs device control. Therefore, the device control device is useful as a device control device that controls an on-vehicle device based on the vital sign.

The invention claimed is:

1. A device control device for controlling an on-vehicle device, said device control device comprising:
   a vital sign measurement unit configured to measure, in time series, time-series pulse wave data from a pulse wave obtained from a user of a pulse wave sensor;
   a parameter extraction unit configured to extract time-series parameter values for evaluating current statuses of the user based on the time-series pulse wave data measured by said vital sign measurement unit;
   a determination unit configured to determine whether a factor of a change in the time-series pulse wave data is a change in a health condition of the user or a change in an environment temperature around the user, based on the time-series parameter values extracted by said parameter extraction unit; and
   a control unit configured to control the on-vehicle device based on a result of the determination made by said determination unit,
   wherein said vital sign measurement unit includes:
      a pulse wave detection unit configured to detect, in the time series, the time-series pulse wave data from the pulse wave obtained from the user;
      a pulse wave derivative unit configured to calculate time-series velocity plethysmogram data by temporally deriving the time-series pulse wave data detected by said pulse wave detection unit;
      a component extraction unit configured to extract a maximum value and a minimum value of the time-series velocity plethysmogram data within a current first time range of the time-series velocity plethysmogram data, while shifting the current first time range in a time axis direction so as to repeat the extraction of the maximum value and the minimum value for multiple current first time ranges of the time-series velocity plethysmogram data;
      a component ratio calculation unit configured to calculate a component ratio for each current first time range, which is a ratio of the maximum value and the minimum value extracted for each current first time range by said component extraction unit;
      a noise segment determination unit configured to determine, as a noise segment, a segment of the time-series pulse wave data in which the component ratios calculated by said component ratio calculation unit are temporally inconstant; and
      a noise segment removal unit configured to remove a portion of the time-series pulse wave data included in the noise segment, and
   wherein said determination unit includes:
      a parameter change amount calculation unit configured to calculate, for each of the time-series parameter values extracted by said parameter extraction unit, a change amount from a starting point, which is a change amount between one of the time-series parameter values extracted by said parameter extraction unit at a predetermined starting time point and a current parameter value of the time-series parameter values;
      a parameter change time calculation unit configured to calculate, for each of the time-series parameter values extracted by said parameter extraction unit, a change time from a starting time point to a current time point at which the current parameter value is extracted; and
      a change factor determination unit configured to: make a first determination that a factor of a change in a vital sign is the change in the health condition of the user when (i) the change amount from the starting point calculated by said parameter change amount calculation unit is greater than a threshold value for the change amount from the starting point and (ii) a time required for the change time calculated by said parameter change time calculation unit is greater than a threshold value for the time required for the change time; and make a second determination that the factor of the change in the vital sign is the change in the environment temperature around the user when (i) the change amount from the starting point calculated by said parameter change amount calculation unit is greater than the threshold value for the change amount from the starting point and (ii) the time required for the change time calculated by said parameter change time calculation unit is not greater than the threshold value for the time required for the change time, said first or second determination being made for each time-series parameter value extracted by said parameter extraction unit.

2. A device control device for controlling an on-vehicle device, said device control device comprising:
   a vital sign measurement unit configured to measure, in time series, time-series pulse wave data from a pulse wave obtained from a user of a pulse wave sensor;
   a parameter extraction unit configured to extract time-series parameter values for evaluating current statuses of the user based on the time-series pulse wave data measured by said vital sign measurement unit;
   a determination unit configured to determine whether a factor of a change in the time-series pulse wave data is a change in a health condition of the user or a change in an environment temperature around the user, based on the time-series parameter values extracted by said parameter extraction unit; and a control unit configured to control the on-vehicle device based on a result of the determination made by said determination unit, wherein said vital sign measurement unit includes:

a pulse wave detection unit configured to detect, in the time series, the time-series pulse wave data from the pulse wave obtained from the user;

a pulse wave derivative unit configured to calculate time-series velocity plethysmogram data by temporally deriving the time-series pulse wave data detected by said pulse wave detection unit;

a component extraction unit configured to extract a maximum value and a minimum value of the time-series velocity plethysmogram data within a current first time range of the time-series velocity plethysmogram data, while shifting the current first time range in a time axis direction so as to repeat the extraction of the maximum value and the minimum value for multiple current first time ranges of the time-series velocity plethysmogram data;

a component ratio calculation unit configured to calculate a component ratio for each current first time range, which is a ratio of the maximum value and the minimum value extracted for each current first time range by said component extraction unit;

a noise segment determination unit configured to determine, as a noise segment, a segment of the time-series pulse wave data in which the component ratios calculated by said component ratio calculation unit are temporally inconstant; and a noise segment removal unit configured to remove a portion of the time-series pulse wave data included in the noise segment, and wherein said determination unit includes:

a parameter change amount calculation unit configured to calculate, for each of the time-series parameter values extracted by said parameter extraction unit, a change amount from a starting point, which is a change amount between one of the time-series parameter values extracted by said parameter extraction unit at a predetermined starting time point and a current parameter value of the time-series parameter values;

an environment temperature measurement unit configured to measure, in time series, environment temperatures around the user;

a unit for calculating a temperature change amount from a starting point, which is a change amount between an environment temperature, of the measured environment temperatures, at the starting point and a current environment temperature measured by said environment temperature measurement unit; and a change factor determination unit configured to: determine that a factor of a change in a vital sign is the change in the health condition of the user when (i) the change amount from the starting point calculated by said parameter change amount calculation unit is greater than a predetermined threshold value for the change amount from the starting point and (ii) the temperature change amount from the starting point calculated by said unit for calculating the temperature change amount is not greater than a predetermined threshold value for the temperature change amount from the starting point; and determine that the factor of the change in the vital sign is a change in the environment temperature around the user when (i) the change amount from the starting point calculated by said parameter change amount calculation unit is greater than the predetermined threshold value for the change amount from the starting point and (ii) the temperature change amount from the starting point calculated by said unit for calculating the temperature change amount is greater than the predetermined threshold value for the temperature change amount from the starting point.

3. A device control device for controlling an on-vehicle device, said device control device comprising:

a vital sign measurement unit configured to measure, in time series, time-series pulse wave data from a pulse wave obtained from a user of a pulse wave sensor;

a parameter extraction unit configured to extract time-series parameter values for evaluating current statuses of the user based on the time-series pulse wave data measured by said vital sign measurement unit;

a determination unit configured to determine whether a factor of a change in the time-series pulse wave data is a change in a health condition of the user or a change in an environment temperature around the user, based on the time-series parameter values extracted by said parameter extraction unit; and a control unit configured to control the on-vehicle device based on a result of the determination made by said determination unit, wherein said vital sign measurement unit includes:

a pulse wave detection unit configured to detect, in the time series, the time-series pulse wave data from the pulse wave obtained from the user;

a pulse wave derivative unit configured to calculate time-series velocity plethysmogram data by temporally deriving the time-series pulse wave data detected by said pulse wave detection unit;

a component extraction unit configured to extract a maximum value and a minimum value of the time-series velocity plethysmogram data within a current first time range of the time-series velocity plethysmogram data, while shifting the current first time range in a time axis direction so as to repeat the extraction of the maximum value and the minimum value for multiple current first time ranges of the time-series velocity plethysmogram data;

a component ratio calculation unit configured to calculate a component ratio for each current first time range, which is a ratio of the maximum value and the minimum value extracted for each current first time range by said component extraction unit;

a noise segment determination unit configured to determine, as a noise segment, a segment of the time-series pulse wave data in which the component ratios calculated by said component ratio calculation unit are temporally inconstant; and a noise segment removal unit configured to remove a portion of the time-series pulse wave data included in the noise segment, and wherein said determination unit includes:

a parameter change amount calculation unit configured to calculate, for each of the time-series parameter values extracted by said parameter extraction unit, a change amount from a starting point, which is a change amount between one of the time-series parameter values extracted by said parameter extraction unit at a predetermined starting time point and a current parameter value of the time-series parameter values;

a parameter change amount integration unit configured to calculate, for each of the time-series parameter values extracted by said parameter extraction unit, an integration value of change amounts from a previous point, the integration value being obtained by integrating the change amount of each of the time-series parameter values extracted by said parameter extraction unit in a period from the starting time point to a time point at which the current parameter value is extracted; and a change factor determination unit configured to: determine that a factor of a change in a vital sign is the change in the health condition of the user when (i) the change amount from the starting point calculated by said parameter change amount calculation unit is greater than a predetermined threshold value for the change amount from the starting point and (ii) the integration value of the time-series parameter values up to the current parameter value extracted by said parameter extraction unit is greater than a predetermined threshold value for the integration value; and determine that the factor of the change in the vital sign is the change in the environment temperature around the user when (i) the change amount from the starting point calculated by said parameter change amount calculation unit is greater than the predetermined threshold value for the change amount from the starting point and (ii) the integration value of the time-series parameter values up to the current parameter value extracted by said parameter extraction unit is not greater than the predetermined threshold value for the integration value.

4. A device control device for controlling an on-vehicle device, said device control device comprising:

a vital sign measurement unit configured to measure, in time series, time-series pulse wave data from a pulse wave obtained from a user of a pulse wave sensor;

a parameter extraction unit configured to extract time-series parameter values for evaluating current statuses of the user based on the time-series pulse wave data measured by said vital sign measurement unit;

a determination unit configured to determine whether a factor of a change in the time-series pulse wave data is a change in a health condition of the user or a change in an environment temperature around the user, based on the time-series parameter values extracted by said parameter extraction unit; and a control unit configured to control the on-vehicle device based on a result of the determination made by said determination unit, wherein said vital sign measurement unit includes:

a pulse wave detection unit configured to detect, in the time series, the time-series pulse wave data from the pulse wave obtained from the user;

a pulse wave derivative unit configured to calculate time-series velocity plethysmogram data by temporally deriving the time-series pulse wave data detected by said pulse wave detection unit;

a component extraction unit configured to extract a maximum value and a minimum value of the time-series velocity plethysmogram data within a current first time range of the time-series velocity plethysmogram data, while shifting the current first time range in a time axis direction so as to repeat the extraction of the maximum value and the minimum value for multiple current first time ranges of the time-series velocity plethysmogram data;

a component ratio calculation unit configured to calculate a component ratio for each current first time range, which is a ratio of the maximum value and the minimum value extracted for each current first time range by said component extraction unit;

a noise segment determination unit configured to determine, as a noise segment, a segment of the time-series pulse wave data in which the component ratios calculated by said component ratio calculation unit are temporally inconstant; and a noise segment removal unit configured to remove a portion of the time-series pulse wave data included in the noise segment, wherein the device control device further comprises a vehicle information obtainment unit configured to obtain information about a status of a vehicle driven by the user, and wherein said determination unit includes:

a parameter change amount calculation unit configured to calculate, for each of the time-series parameter values extracted by said parameter extraction unit, a change amount from a starting point, which is a change amount between one of the time-series parameter values extracted by said parameter extraction unit at a predetermined starting time point and a current parameter value of the time-series parameter values; and a change factor determination unit configured to determine whether the factor of the change in the time-series pulse wave data is the change in the health condition of the user or the change in the environment temperature around the user, based on the change amount from the starting point calculated by said parameter change amount calculation unit and the information about the status of the vehicle obtained by said vehicle information obtainment unit.

5. A device control device for controlling an on-vehicle device, said device control device comprising:

a vital sign measurement unit configured to measure, in time series, time-series pulse wave data from a pulse wave obtained from a user of a pulse wave sensor;

a parameter extraction unit configured to extract time-series parameter values for evaluating current statuses of the user based on the time-series pulse wave data measured by said vital sign measurement unit;

a determination unit configured to determine whether a factor of a change in the time-series pulse wave data is a change in a health condition of the user or a change in an environment temperature around the user, based on the time-series parameter values extracted by said parameter extraction unit; and a control unit configured to control the on-vehicle device based on a result of the determination made by said determination unit, wherein said vital sign measurement unit includes:

a pulse wave detection unit configured to detect, in the time series, the time-series pulse wave data from the pulse wave obtained from the user;

a pulse wave derivative unit configured to calculate time-series velocity plethysmogram data by temporally deriving the time-series pulse wave data detected by said pulse wave detection unit;

a component extraction unit configured to extract a maximum value and a minimum value of the time-series velocity plethysmogram data within a current first time range of the time-series velocity plethysmogram data, while shifting the current first time range in a time axis direction so as to repeat the extraction of the maximum value and the minimum value for multiple current first time ranges of the time-series velocity plethysmogram data;

a component ratio calculation unit configured to calculate a component ratio for each current first time range, which is a ratio of the maximum value and the minimum value extracted for each current first time range by said component extraction unit;

a noise segment determination unit configured to determine, as a noise segment, a segment of the time-series pulse wave data in which the component ratios calculated by said component ratio calculation unit are temporally inconstant; and a noise segment removal unit configured to remove a portion of the time-series pulse wave data included in the noise segment, wherein the device control device further comprises a vehicle information obtainment unit configured to obtain information about a status of a vehicle driven by the user, and wherein said determination unit includes:

a parameter change amount calculation unit configured to calculate, for each of the time-series parameter values extracted by said parameter extraction unit, a change amount from a starting point, which is a change amount between one of the time-series parameter values extracted by said parameter extraction unit at a predetermined starting time point and a current parameter value of the time-series parameter values;

a parameter change time calculation unit configured to calculate, for each of the time-series parameter values extracted by said parameter extraction unit, a time required for a change which is time from the starting time point to a time point at which the current parameter value is extracted; and a change factor determination unit configured to determine whether the factor of the change in the time-series pulse wave data is the change in the health condition of the user or the change in the environment temperature around the user, based on the change amount from the starting point calculated by said parameter change amount calculation unit, the time required for the change calculated by said parameter change time calculating unit, and the information about the status of the vehicle obtained by said vehicle information obtainment unit.

* * * * *